(12) United States Patent
Lo et al.

(10) Patent No.: US 10,759,994 B2
(45) Date of Patent: Sep. 1, 2020

(54) LUMINOGENIC TRANSITION METAL-BASED PYRIDYL COMPLEX AND ITS USE

(71) Applicant: City University of Hong Kong, Kowloon (HK)

(72) Inventors: Kam Wing Kenneth Lo, Kowloon (HK); Hua Wei Liu, Sha Tin (HK); Cho Cheung Lee, Kowloon (HK); Siu Ming Tang, New Territories (HK)

(73) Assignee: City University of Hong Kong, Kowloon (HK)

( * ) Notice: Subject to any disclaimer, the term of this patent is extended or adjusted under 35 U.S.C. 154(b) by 357 days.

(21) Appl. No.: 15/359,736

(22) Filed: Nov. 23, 2016

(65) Prior Publication Data
US 2018/0142144 A1    May 24, 2018

(51) Int. Cl.
| | | |
|---|---|---|
| A61B 5/00 | (2006.01) | |
| A61B 8/00 | (2006.01) | |
| A61B 10/00 | (2006.01) | |
| C09K 11/06 | (2006.01) | |
| C09B 57/10 | (2006.01) | |
| G01N 33/58 | (2006.01) | |
| G01N 1/30 | (2006.01) | |
| A61K 49/00 | (2006.01) | |
| C09B 55/00 | (2006.01) | |

(52) U.S. Cl.
CPC .......... *C09K 11/06* (2013.01); *A61K 49/0015* (2013.01); *C09B 55/003* (2013.01); *C09B 57/10* (2013.01); *G01N 1/30* (2013.01); *G01N 33/582* (2013.01); *A61K 49/0013* (2013.01); *C09K 2211/185* (2013.01); *G01N 2001/302* (2013.01)

(58) Field of Classification Search
None
See application file for complete search history.

(56) References Cited

U.S. PATENT DOCUMENTS

2005/0059638 A1* 3/2005 Kelly .................... C07C 291/02
514/114

OTHER PUBLICATIONS

Gerardi et al. (Analyt. Chinn. Acta 1999, 378, 1-41).*
Gorman et al. (Analyst 2006, 131, 616-639).*
Peek et al. (Int. J. Peptide Protein Res. 1991, 38, 114-123).*

* cited by examiner

*Primary Examiner* — Michael G. Hartley
*Assistant Examiner* — Melissa J Perreira
(74) *Attorney, Agent, or Firm* — Renner Kenner Greive Bobak Taylor & Weber

(57) ABSTRACT

The present invention provides a luminogenic, in particular a phosphorogenic transition metal-based pyridyl complex containing a nitrone moiety, which nitrone moiety acts as a bioorthogonal functional group and an emission quencher, and can undergo cycloaddition reaction with a complementary bioorthogonal functional group coupled to a substrate. The transition metal is can be selected from iridium or ruthenium. Also disclosed is a method for preparing the transition metal-based pyridyl complex and a pharmaceutical composition comprising it. Still further provided is a method for bioorthogonal labeling of a biomolecule, a method for staining of a cell structure, a method for in vivo imaging of an organism, and a kit for in vivo imaging of an organism. The luminogenic properties and high reactivity of the complexes are highly advantageous for bioorthogonal labeling and imaging of biomolecules in their native biological environments at much lower costs than those of the existing commercial products.

18 Claims, 8 Drawing Sheets
(3 of 8 Drawing Sheet(s) Filed in Color)

LUMINOGENIC TRANSITION METAL-BASED PYRIDYL COMPLEX AND ITS USE

TECHNICAL FIELD

The present invention relates to a luminogenic, in particular a phosphorogenic transition metal-based pyridyl complex comprising a nitrone moiety that acts as both a bioorthogonal functional group and an emission quencher. The nitrone moiety can undergo cycloaddition reaction with a complementary bioorthogonal functional group coupled to a substrate. The transition metal is especially preferably but not exclusively selected from iridium or ruthenium. The present invention further provides a method for preparing the transition metal-based pyridyl complex and a pharmaceutical composition comprising it. Still further provided are a method for bioorthogonal labeling of a biomolecule, a method for staining of a cell structure such as the cell membrane, a method for in vivo imaging of an organism, and a kit for in vivo imaging of an organism.

BACKGROUND OF THE INVENTION

Bioorthogonal labeling involves the metabolic or genetic incorporation of a biomolecule of interest containing a functional group (also called chemical reporter) into live cells and organisms, and subsequent labeling with a bioorthogonal probe that carries the specific reaction partner, i.e., that has certain functional group for reaction with the abiotic functional group of the biomolecule. Recently, there has been a rapidly emerging interest in exploiting bioorthogonal probes, in particular those which can display emission turn-on after the labeling, i.e., which remain essentially non-emissive as long as the appended bioorthogonal group is intact but show emission turn-on upon the specific labeling. Their use could eliminate the need for stringent washouts to remove unreacted probes, improve the signal-to-noise ratio, and offer the opportunity to monitor biological processes in real time.

Although there are a number of fluorescent bioorthogonal probes available in the market, all of them are organic dyes. They show strong fluorescence but their applications are limited by several key factors such as high photobleaching rates, substantial self-quenching, high pH dependence, and short-lived fluorescence that is not compatible with fluorescence-lifetime imaging microscopy (FLIM). There are a small number of organic bioorthogonal probes that show fluorogenic labeling properties, i.e., fluorescence will be turned on after the bioorthogonal labeling. However, the design of these probes is based on the use of an azide unit, which quenches the fluorescence of the compounds before their reactions with alkynes. The largest limitation of these fluorogenic probes is that the azide unit is susceptible to reduction by thiols, which commonly exist in living systems (e.g. the intracellular concentration of glutathione in human cells usually ranges from 0.5 to 10 mM). This limits the applications of these azide-containing fluorogenic probes because the emission could be turned on in the absence of the genuine chemical reporter, i.e., in the absence of the abiotic functional group.

Since the concept of bioorthogonal chemistry appeared in the literature less than twenty years ago, a number of chemical reporters and fluorescent bioorthogonal probes have been designed and produced. However, most of the probes developed so far are organic dyes that are already highly fluorescent before the specific labeling, and hence stringent washouts are required after the staining. The use of probes that show emission turn-on after the bioorthogonal labeling provided so far is limited for several reasons as mentioned above. Thus, there remains a strong need for bioorthogonal probes that show emission turn-on only after the specific labeling, which are further photostable, do not suffer from self-quenching, and allow for a sufficient enhancement of emission after the labeling reaction which emission has a long lifetime, e.g. which is compatible with FLIM and, for example, suitable for detection of cell structures and measurement of metabolic activities in the native biological environments, for disease diagnosis, and for identification of therapeutics.

SUMMARY OF THE INVENTION

The first aspect of the present invention relates to a luminogenic, in particular a phosphorogenic transition metal-based pyridyl complex containing a nitrone moiety that acts as both a bioorthogonal functional group and an emission quencher. The nitrone moiety can undergo cycloaddition reaction with a complementary bioorthogonal functional group coupled to a substrate.

The nitrone moiety is preferably coupled to a pyridine, in particular a polypyridyl ligand in the transition metal-based pyridyl complex. The substrate is in particular a biomolecule and the complementary bioorthogonal functional group coupled to the biomolecule in particular contains a strained alkyne moiety, which may further include a linker to be coupled to the biomolecule, namely a group linking the strained alkyne to the biomolecule. The nitrone moiety of the transition metal-based pyridyl complex of the present invention preferably comprises a structure of Formula (I):

Formula (I)

$R_1$ is particularly an optionally substituted polypyridyl ligand such as a 2,2'-bipyridine substituted with a methyl group and in particular $R_1$ has a structure of Formula (II):

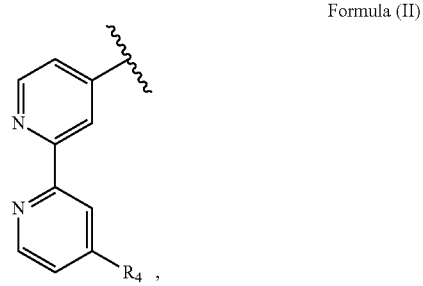

Formula (II)

with $R_4$ being an alkyl group, in particular a methyl group. I.e., the nitrone moiety is particularly covalently bound to a pyridine, in particular a polypyridyl ligand. $R_2$ is particularly a hydrogen atom. $R_3$ is an alkyl or an aryl group, in particular a methyl or a phenyl group.

In particular, the transition metal-based pyridyl complex is formed by components comprising a transition metal ion, a polypyridyl ligand having the structure of Formula (III):

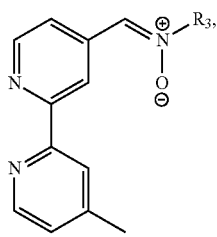

Formula (III)

wherein R₃ is as described above, and two identical pyridyl ligands selected from the structures of Formula (IV) to (X):

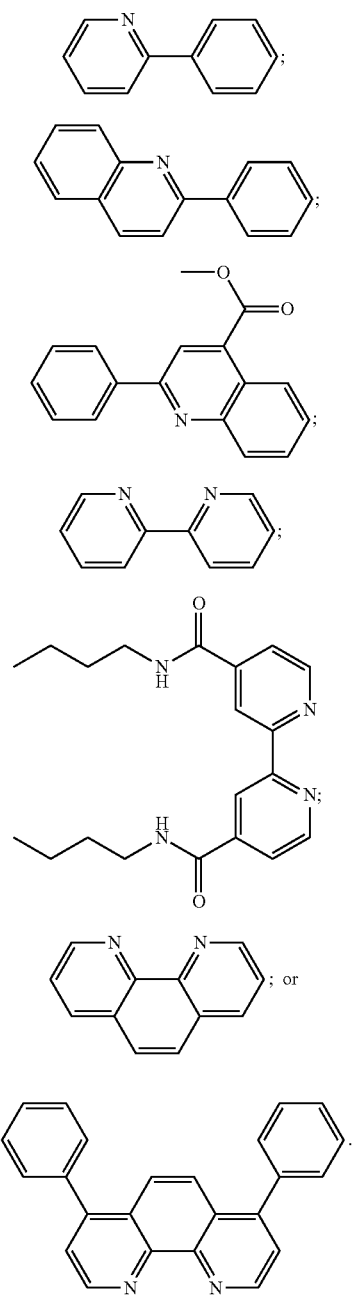

Formula (IV)

Formula (V)

Formula (VI)

Formula (VII)

Formula (VIII)

Formula (IX); or

Formula (X)

The transition metal is particularly selected from iridium or ruthenium, in particular iridium(III) and ruthenium(II).

The present invention further refers to a method for preparing the transition metal-based pyridyl complex of the present invention. The present invention also provides a pharmaceutical composition with the luminogenic transition metal-based pyridyl complex described above and one or more pharmaceutically tolerable excipients such as one or more of a pharmaceutically tolerable carrier, salt, buffer, solvent, diluent, or filler.

The present invention in another aspect provides a method for bioorthogonal labeling of a biomolecule with a luminogenic transition metal-based pyridyl complex as described above. Said method comprises:

(i) introducing a biomolecule with a complementary bioorthogonal functional group coupled to said biomolecule into a living system; and (ii) introducing the luminogenic transition metal-based pyridyl complex as described above which may also be, for example, in form of a salt and/or solvate into the living system.

The complementary bioorthogonal functional group coupled to the biomolecule used in step (i) is preferably a strained alkyne moiety, in particular an optionally substituted cycloalkyne, further preferred a bicyclo[6.1.0]nonyne, in particular the complementary bioorthogonal functional group comprises a structure of Formula (XVII):

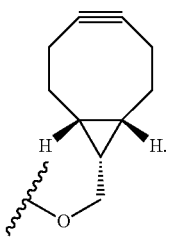

Formula (XVII)

The method may further comprise a step (iii) of imaging the living system with luminescence, in particular phosphorescence detection such as with confocal microscopy, in particular laser scanning confocal microscopy (LSCM).

Further provided with the present invention is a method for staining of a cell structure comprising:

(i) introducing N-[(1R,8S,9s)-bicyclo[6.1.0]non-4-yn-9-ylmethyloxycarbonyl]-1-aminodecane (BCN-C10) of Formula (XIX) into a cell population:

Formula (XIX)

and (ii) introducing the luminogenic transition metal-based pyridyl complex as described above into the cell population.

The cell structure can be the cell membrane or the cytosol, in particular it is the cell membrane.

The present invention provides in another aspect a method for in vivo imaging of an organism comprising:

(i) administering an effective amount of a biomolecule with a complementary bioorthogonal functional group coupled to the biomolecule to said organism;

(ii) administering an effective amount of a luminogenic transition metal-based pyridyl complex as described above which may also be in form of a salt and/or solvate to said organism; and (iii) imaging the organism in particular comprising luminescence, wherein a signal indicates the presence of a labeled biomolecule.

The complementary bioorthogonal functional group coupled to the biomolecule used in step (i) is preferably a strained alkyne moiety, in particular an optionally substituted cycloalkyne, further preferred a bicyclo[6.1.0]nonyne, in particular the complementary bioorthogonal functional group comprises a structure of Formula (XVII):

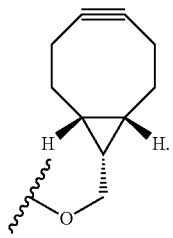

Formula (XVII)

Step (iii) of imaging the organism can comprise phosphorescence detection such as with confocal microscopy, in particular LSCM. The present invention further refers to a kit for in vivo imaging of an organism comprising:

(i) an effective amount of a biomolecule with a complementary bioorthogonal functional group coupled to the biomolecule;

(ii) an effective amount of a luminogenic transition metal-based pyridyl complex as described above such as in form of a salt and/or solvate; and (iii) optionally pharmaceutically tolerable excipients.

The biomolecule is particularly a targeting biomolecule. The pharmaceutically tolerable excipients in particular include one or more of a pharmaceutically tolerable carrier, salt, buffer, solvent, diluent, or filler.

The inventors particularly found for the first time that a nitrone is particularly suitable for phosphorogenic bioorthogonal labeling as it acts as both a bioorthogonal functional group and an emission quencher. Firstly, the nitrone moiety proved to undergo strain-promoted alkyne-nitrone cycloaddition (SPANC) with a strained alkyne moiety coupled to a biomolecule to form an N-alkylated isoxazoline. Secondly, the C═N isomerization proved to provide a facile non-radiative deactivation pathway for an initially luminescent transition metal-based pyridyl complex. When the isomerization of the C═N group of the nitrone moiety was inhibited, the transition metal-based pyridyl complex proved to resume its emission behavior. The inventors, thus, found that incorporating a nitrone moiety into luminescent, in particular phosphorescent transition metal-based pyridyl complexes such as phosphorescent iridium(III) and ruthenium(II) pyridyl complexes represents a highly promising approach for providing luminogenic, in particular phosphorogenic bioorthogonal probes for biomolecules coupled to or modified with a strained alkyne, i.e., to detect and visualize such biomolecules in their native settings (e.g. live cells and organisms such as animals) via bioorthogonal labeling.

In contrast to fluorescent organic dyes, phosphorescent transition metal-based pyridyl complexes are highly photostable, which allows continuous tracking and monitoring of biomolecules and metabolic processes in stained cells and organisms. Also, since phosphorescence originates from a triplet excited state and is associated with a large Stokes' shift and long emission lifetime, the use of transition metal-based pyridyl complexes is not associated with problems such as self-quenching and short emission lifetimes. Additionally, their long emission lifetimes can also facilitate the detection and imaging of live cells by FLIM, which offers much enhanced sensitivity and lower limits of detection. Also, the involvement of transition metals such as iridium or ruthenium enables the cellular uptake to be readily quantitated by ICP-MS, which is not applicable to organic dyes. Furthermore, unlike organic azide dyes, transition metal-based pyridyl complexes containing a nitrone moiety are stable and remain intact even in the presence of thiols.

The inventors could, for example, show that a new class of iridium(III) and ruthenium(II) polypyridyl complexes containing a nitrone moiety are non-emissive or weakly emissive while exhibiting advantageously large emission enhancement upon the SPANC reaction with strained alkynes such as with bicyclo[6.1.0]nonyne (BCN)-modified biomolecules. The revealed phosphorogenic properties and high reactivity, namely increased SPANC reaction kinetics, of these iridium(III) and ruthenium(II) polypyridyl complexes are highly advantageous for bioorthogonal labeling and imaging of biomolecules such as BCN-modified biomolecules in their native biological environments at much lower costs than those of existing commercial products. The ruthenium(II) polypyridyl complexes further proved to be able to achieve specific cell membrane and/or cytosol staining upon specific labeling of BCN-modified decane (BCN-C10) in live cells and, are, thus particularly suitable to be used for staining the cell membrane or cytosol of live cells.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows SDS-PAGE patterns of unmodified BSA and BCN-BSA incubated with complex 1a. FIG. 1B shows SDS-PAGE patterns of unmodified BSA and BCN-BSA incubated with complex 2a. FIG. 1C shows SDS-PAGE patterns of unmodified BSA and BCN-BSA incubated with complex 3a.

DETAILED DESCRIPTION OF THE INVENTION

Figure 1A:
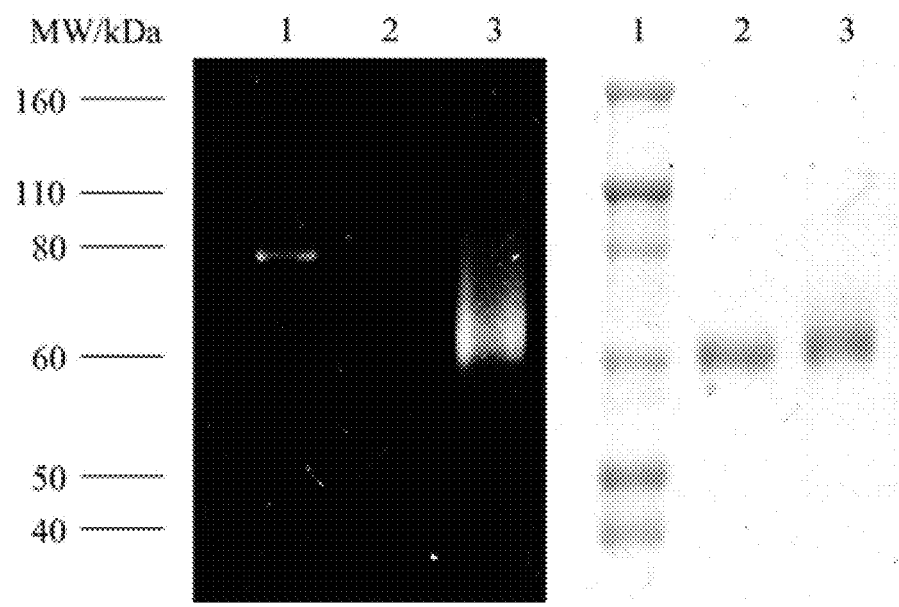
FIGS. 1A, 1B, and 1C show SDS-PAGE patterns of unmodified BSA and bicyclo[6.1.0]nonyne (BCN)-BSA (2.50 μM) incubated with complexes 1a, 2a and 3a (25 μM) in potassium phosphate buffer (50 mM, pH 7.4)/DMSO (9:1, v/v) at 25° C. (298 K). Left: UV transillumination; right: Coomassie Blue staining. Lane 1: protein ladder; lane 2: complex with unmodified BSA; lane 3: complex with BCN-BSA.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. As used herein, the forms "a", "an", and "the" are intended to include the singular and plural forms unless the context clearly indicates otherwise.

The present invention provides a luminogenic transition metal-based pyridyl complex containing a nitrone moiety. The nitrone moiety can undergo cycloaddition reaction with a complementary bioorthogonal functional group coupled to a substrate.

The term "bioorthogonal" generally describes chemical reactants and chemical reactions of these reactants which are compatible with living systems such as cells or an organism and can proceed under physiological conditions, i.e., in aqueous media at physiological pH and temperature and lead to stable reaction products under these conditions. Namely, the term describes any chemical reaction that can occur inside of living systems without interfering with native biochemical processes. "Bioorthogonal functional groups" are functional groups of or coupled to reactants, in the present invention the transition metal-based pyridyl complex and the biomolecule, able to react to form covalent bonds. The bioorthogonal functional group of the transition metal-based pyridyl complex is, thus, a functional group able to react, namely to undergo cycloaddition reaction, under physiological conditions with a corresponding functional group, herein referred to as "complementary bioorthogonal functional group" that can be coupled to biomolecules. Said complementary bioorthogonal functional group must not alter the structure of the biomolecule dramatically to avoid affecting its bioactivity.

The term "luminescent" generally means that a material or a compound is capable of emitting light for any reason other than a rise in its temperature, i.e., is capable of exhibiting luminescence such as fluorescence or phosphorescence. The light emitted comprises radiation outside the visible region. The term "luminogenic" as used herein denotes a transition metal-based pyridyl complex that comprises a luminophore group capable of absorbing light energy and emitting all or part of this energy and that also comprises an emission quencher group which is a group able to at least partially mask the luminescence of the luminophore group. The emission quantum yield of the transition metal-based pyridyl complex of the present invention is particularly less than 0.05 in dichloromethane ($CH_2Cl_2$), acetonitrile ($CH_3CN$), or potassium phosphate buffer (about 50 mM, pH about 7.4) containing 30% methanol (MeOH), 20% MeOH, or 10% DMSO at about 25° C. (about 298 K), in particular less than 0.04 such as less than 0.02 or even lower. Namely, the luminescence of the transition metal-based pyridyl complex of the present invention is significantly reduced compared to common transition metal-based pyridyl complexes due to the presence of the emission quencher group. I.e., the transition metal-based pyridyl complex is not luminescent or is only weakly luminescent but can be converted such that it exhibits increased luminescence, in particular significantly increased luminescence, after the cycloaddition reaction between the bioorthogonal functional group of the luminogenic transition metal-based pyridyl complex and the complementary bioorthogonal functional group coupled to a substrate. The substrate is in particular a biomolecule.

In particular after the cycloaddition reaction of the bioorthogonal functional group of the luminogenic transition metal-based pyridyl complex with the complementary bioorthogonal functional group, the emission quencher group is converted to a non-quenching structure such as an isoxazoline structure, enabling the luminophore group to emit light. In the luminogenic transition metal-based pyridyl complex of the present invention, the luminophore group is the transition metal-based pyridyl complex and the emission quencher group comprises the nitrone moiety. Namely, it is assumed that when the isomerization of the C═N group in the nitrone moiety is inhibited, the transition metal-based pyridyl complex resumes its emission behavior.

I.e., the nitrone moiety functions as both a bioorthogonal functional group and an emission quencher. For example, the nitrone moiety undergoes a cycloaddition reaction with a complementary bioorthogonal functional group coupled to the biomolecule leads to an increase, in particular significant increase in the luminescence, in particular phosphorescence, with an emission enhancement ($I/I_0$) ratio of at least 7, in particular at least 8, further preferred at least 10, and still further preferred of more than 10, wherein I and $I_0$ are the emission intensities of the transition metal-based pyridyl complex of the present invention in the presence and absence, respectively, of the biomolecule coupled with the complementary bioorthogonal functional group under the same conditions such as in aerated potassium phosphate buffer (about 50 mM, pH about 7.4) containing 10% v/v MeOH or 1% v/v DMSO at about 25° C. (about 298 K) with about 10 µM of the transition metal-based pyridyl complex. The concentration of the biomolecule depends on the specific biomolecule and may be, for example, about 2 µM to about 20 µM.

The transition metal-based pyridyl complex is particularly phosphorogenic, i.e., capable of exhibiting phosphorescence. "Phosphorescence" as used herein describes a material in which the luminescence persists significantly after the excitation source is removed in contrast to fluorescence. Namely, a phosphorescent material does not immediately re-emit the radiation it absorbs in contrast to fluorescence. The phosphorescence can be in any region of the electromagnetic spectrum but is particularly in the visible region such as in the yellow to red region of the visible range and in particular at wavelengths of between about 500 nm and about 700 nm, further preferred in the red to near-infrared region.

The term "transition metal-based pyridyl complex", as used herein refers to a complex formed between a transition metal in particular transition metal ion as coordination center and one or more, in particular three pyridyl ligands coordinated therewith which transition metal-based pyridyl complex optionally further comprises a counterion. The transition metal-based pyridyl complex further contains a nitrone moiety which acts as a bioorthogonal functional group, in particular a nitrone moiety directly linked to a pyridyl ligand. The transition metal-based pyridyl complex does preferably not comprise any non-pyridyl ligands.

The term "pyridyl ligand" as used herein means a ligand having at least one pyridine ring, i.e., a pyridyl ligand comprises one or more pyridine rings. A pyridyl ligand of the transition metal-based pyridyl complex in particular comprises a pyridine ring covalently linked to one or more other rings such as one or more other pyridine rings and/or phenyl rings, which may together form a larger ring system. For the terms "polypyridyl ligand" and "cyclometalating ligand", they refer to a pyridyl ligand comprising a pyridine ring covalently linked to one or more pyridine rings (i.e., polypyridyl ligand), and a pyridine ring covalently linked to one or more phenyl rings (i.e., cyclometalating ligand), respectively. The pyridine ring and preferred additional rings may be substituted. The term "substituted" means that one or more hydrogen atoms are replaced by certain substituent(s) provided that this results in the formation of a stable moiety.

For example, substituents may be selected from alkyl groups, alkoxy groups, ester groups (—COOR), and/or amide groups (—CONHR), wherein R means particularly an alkyl group. The term "alkyl" as used herein, refers to saturated, straight-chain or branched hydrocarbon radicals derived from a hydrocarbon moiety containing between 1 and 20 carbon atoms by removal of a single hydrogen atom. In embodiments of the present invention, the alkyl group contains 1 to 5 carbon atoms. The term "alkoxy group" means a group of the formula —OR, wherein R is an alkyl group.

Preferred pyridyl ligands comprise a pyridine ring covalently linked to one or more other pyridine rings and/or aryl rings such as phenyl rings which ring components are optionally substituted, wherein one of the pyridyl ligands of the transition metal-based pyridyl complex contains a nitrone moiety particularly directly linked to said pyridyl ligand. The term "aryl" as used herein, refers to an aromatic mono- or polycyclic ring system particularly having 3 to 8 ring atoms, of which all the ring atoms are carbon atoms, and which may be substituted and include phenyl, biphenyl, naphthyl, and the like which may be optionally substituted. If the term "aryl" such as "phenyl" is used herein without mentioning an optional substituent, this means that the aryl is unsubstituted.

More preferred the pyridyl ligands are selected from optionally substituted phenylpyridine, phenylquinoline, bipyridine, phenanthroline, and/or diphenylphenanthroline, in particular from optionally substituted 2-phenylpyridine, 2-phenylquinoline, 2,2'-bipyridine, 1,10-phenanthroline, and/or 4,7-diphenyl-1,10-phenanthroline, wherein one pyridyl ligand has the bioorthogonal functional group. The pyridyl ligands of the present invention preferably are polydentate ligands, i.e., two or more atoms of each ligand are coordinated to the transition metal. As used herein the term "polydentate ligand" refers to ligands which may be bidentate, tridentate, tetradentate, etc. In particular embodiments of the present invention, the pyridyl ligands are selected from polypyridyl ligands, i.e., they comprise two or more pyridine rings optionally covalently linked to one or more aryl rings such as phenyl rings which ring components are optionally substituted, wherein one polypyridyl ligand has the bioorthogonal functional group. Polypyridyl ligands particularly include optionally substituted 2,2'-bipyridine, 1,10-phenanthroline, and/or 4,7-diphenyl-1,10-phenanthroline.

Typically complexation of the pyridyl ligands to the transition metal, in particular transition metal ion, in the transition metal-based pyridyl complex of the present invention occurs though a nitrogen atom and/or a carbon atom such as a $sp^2$ hybridized carbon atom, in particular through the nitrogen atom of each pyridine ring of a polypyridyl ligand or the nitrogen atom of a pyridine ring and a carbon atom such as a $sp^2$ hybridized carbon atom of a phenyl ring of a cyclometalating ligand.

A nitrone moiety is a functional group known to one of skill in the art and is an N-oxide of an imine. The general structure is $R_1R_2C=NR_3{}^+O^-$, where $R_3$ is not a hydrogen atom. The bioorthogonal functional group of the transition metal-based pyridyl complex of the present invention preferably comprises a structure of Formula (I):

Formula (I)

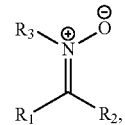

$R_1$ is a polypyridyl ligand, in particular an optionally substituted polypyridyl ligand, more preferably an optionally substituted bipyridine, further preferred a 2,2'-bipyridine substituted with an alkyl group, in particular a methyl group, and further preferred having a structure of Formula (II):

Formula (II)

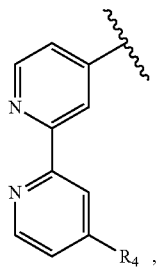

with $R_4$ being an alkyl group, in particular a methyl group or an ethyl group, more preferably $R_4$ a methyl group. I.e., the bioorthogonal functional group is preferably directly bound to a pyridyl ligand, in particular a polypyridyl ligand. $R_2$ is particularly a hydrogen atom. $R_3$ is an alkyl or an aryl group, in particular a methyl or a phenyl group.

Most preferably, the transition metal-based pyridyl complex is formed by components comprising a transition metal ion, a polypyridyl ligand having the structure of Formula (III):

Formula (III)

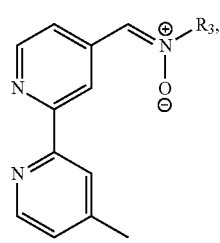

wherein $R_3$ is as described above, and two identical pyridyl ligands selected from the structures of:

Formula (IV)

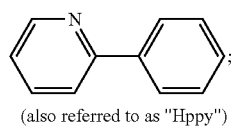

(also referred to as "Hppy")

Formula (V)

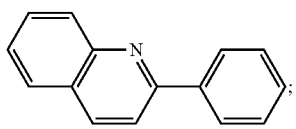

(also referred to as "Hpq")

Formula (VI)

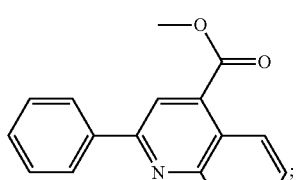

(also referred to as "Hpqe")

Formula (VII)

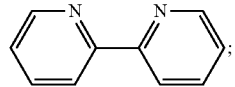

(also referred to as "bpy")

Formula (VIII)

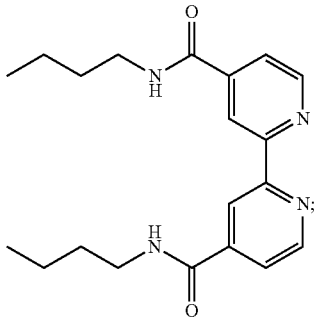

(also referred to as "bpyC4")

Formula (IX)

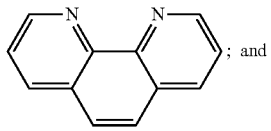

; and (also referred to as "phen")

Formula (X)

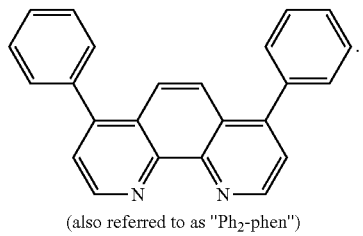

(also referred to as "Ph$_2$-phen")

More preferably, the transition metal-based pyridyl complex is formed by components comprising a transition metal ion, a polypyridyl ligand having the structure of Formula (III) wherein $R_3$ is as described above, and two identical pyridyl ligands selected from the structures of Formula (IV) to (X), in particular all three pyridyl ligands are polydentate, in particular bidentate ligands. I.e., in an embodiment, the transition metal-based pyridyl complex is formed by components comprising a transition metal ion, a polypyridyl ligand having the structure of Formula (III) wherein $R_3$ is as described above, and two identical cyclometalating ligands of the structure of Formula (IV), (V), or (VI). In another embodiment, the transition metal-based pyridyl complex is formed by components comprising a transition metal ion, a polypyridyl ligand having the structure of Formula (III) wherein $R_3$ is as described above, and two identical polypyridyl ligands of the structure of Formula (VII), (VIII), (IX), or (X).

In especially preferred embodiments of the present invention, the transition metal-based pyridyl complex is formed by components comprising a transition metal ion, a polypyridyl ligand having the structure of Formula (III) wherein $R_3$ is as described above, and two identical polypyridyl ligands selected from the structures of Formula (VII) to (X), in particular all three polypyridyl ligands are polydentate, in particular bidentate ligands:

Formula (VII)

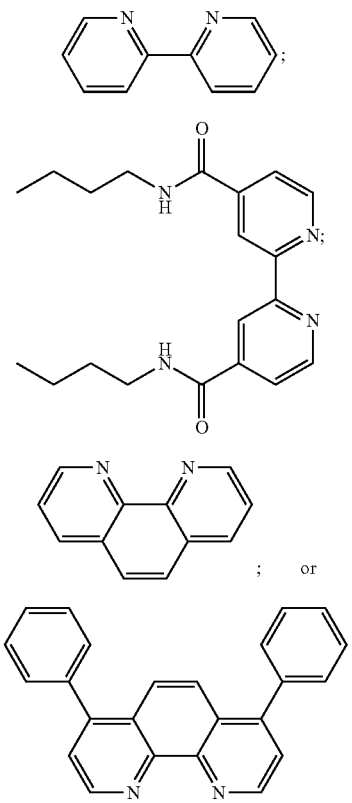

Formula (VIII)

Formula (IX)

; or

Formula (X)

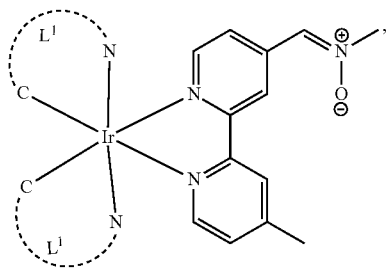

The transition metal is preferably selected from a transition metal of the group 8, 9, or 10 in the periodic table of the chemical elements according to the current IUPAC numbering, i.e., corresponding to group VIIIa/VIII of the old IUPAC numbering. The transition metal is most preferably iridium or ruthenium, in particular iridium(III) and ruthenium(II).

The transition metal-based pyridyl complex in embodiments of the present invention comprises a structure of Formula (XI), in particular of Formula (XII) including any salts and solvates thereof:

Formula (XI)

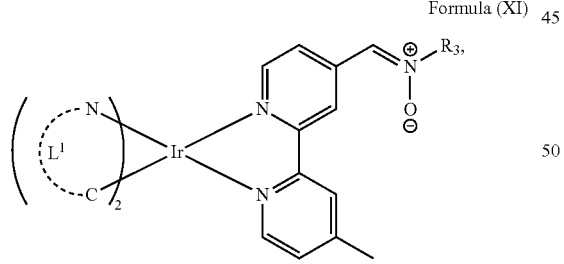

in particular

Formula (XII)

with $R_3$ being as defined above and $L^1$ being a pyridyl ligand in particular a cyclometalating ligand particularly selected from a structure of:

Formula (IV)

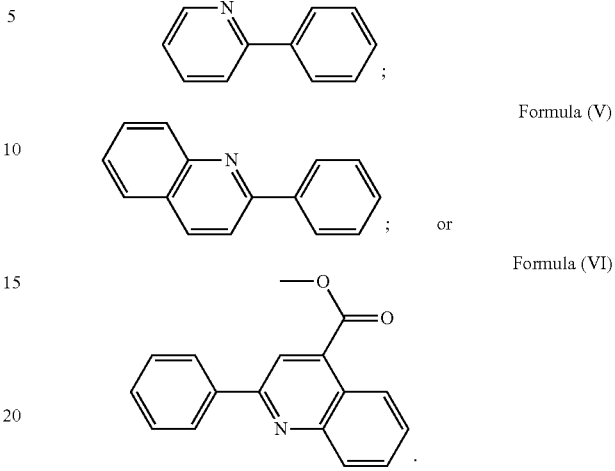

Formula (V)

; or

Formula (VI)

In another preferred embodiment of the present invention, the transition metal-based pyridyl complex comprises a structure of Formula (XIII), in particular of Formula (XIV) or Formula (XV) including any salts or solvates thereof:

Formula (XIII)

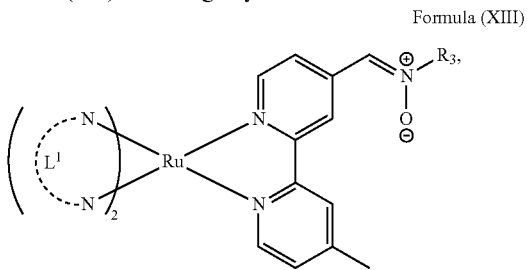

in particular

Formula (XIV)

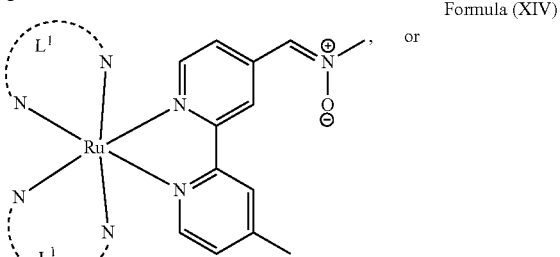

or

Formula (XV)

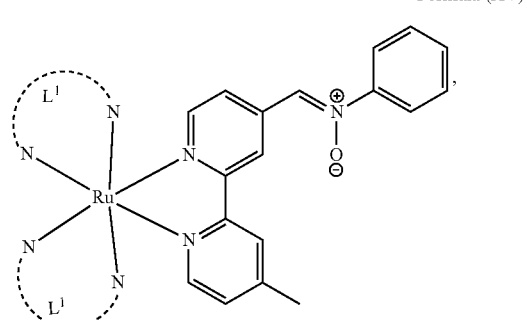

with $R_3$ being as defined above and $L^1$ being a pyridyl ligand in particular a polypyridyl ligand selected from a structure of:

Formula (VII)

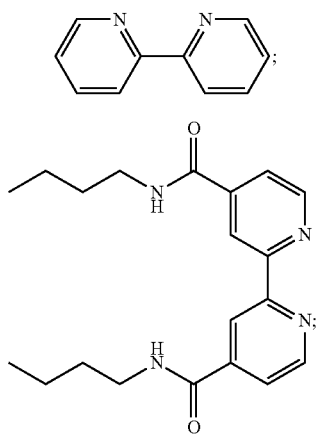

Formula (VIII)

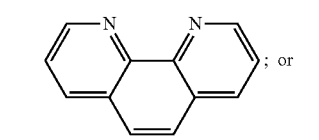

Formula (IX)

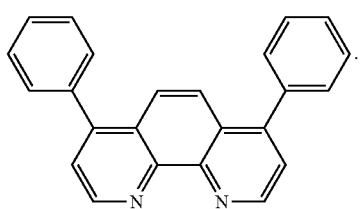

Formula (X)

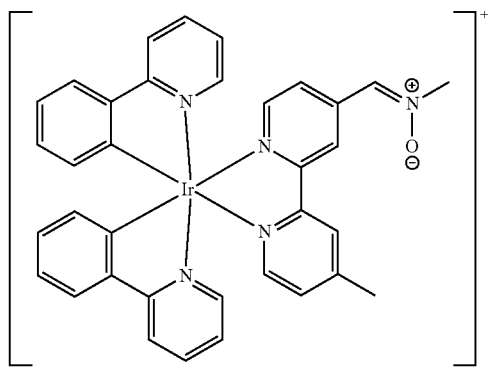

Particular transition metal-based pyridyl complexes comprise a structure of Formula (XII) with $L^1$ being a pyridyl ligand in particular a cyclometalating ligand selected from a structure of Formula (IV), (V), or (VI), or a structure of Formula (XIV) with $L^1$ being a pyridyl ligand in particular a polypyridyl ligand selected from a structure of Formula (VII), (VIII), (IX), or (X), or a structure of Formula (XV) with $L^1$ being a pyridyl ligand in particular a polypyridyl ligand selected from a structure of Formula (VII). In further preferred embodiments, the transition metal-based pyridyl complex comprises a structure of Formula (XIV) with $L^1$ being a pyridyl ligand in particular a polypyridyl ligand selected from a structure of Formula (VII), (VIII), (IX), or (X) or a structure of Formula (XV) with $L^1$ being a pyridyl ligand in particular a polypyridyl ligand selected from a structure of Formula (VII).

Most preferably, the transition metal-based pyridyl complex comprises a structure selected from:

Formula (XIIa)

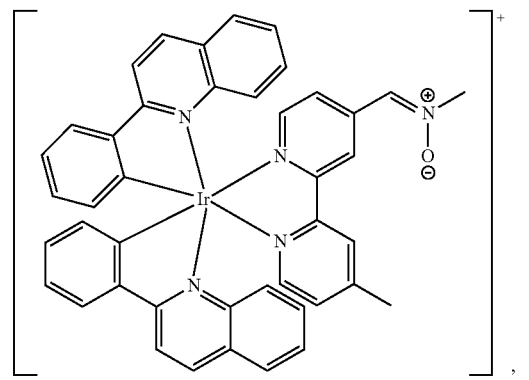

(also referenced as "complex 1a" herein)

Formula (XIIb)

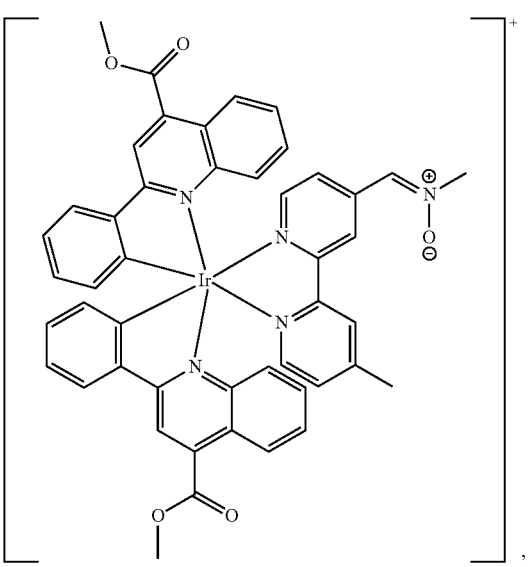

(also referenced as "complex 2a" herein)

Formula (XIIc)

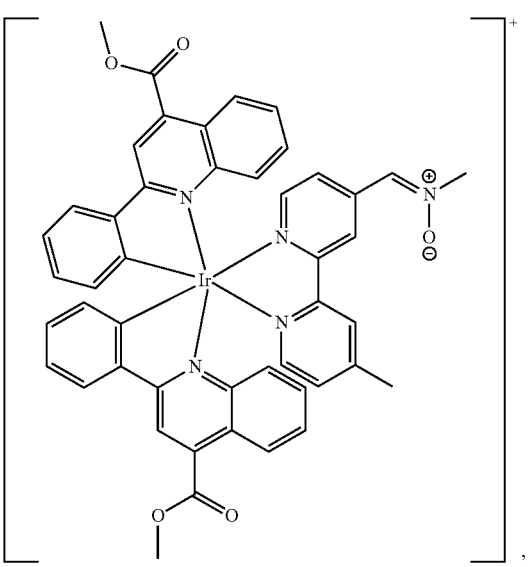

(also referenced as "complex 3a" herein)

Formula (XIVa)

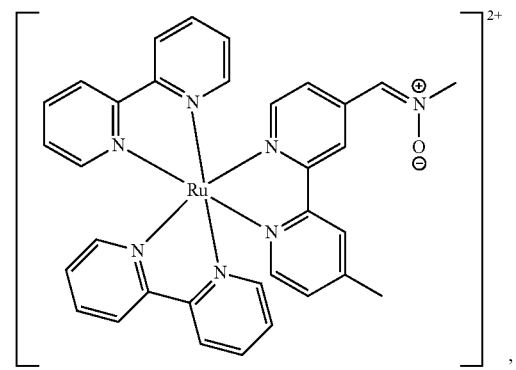

(also referenced as "complex 1b" herein)

Formula (XIVb)

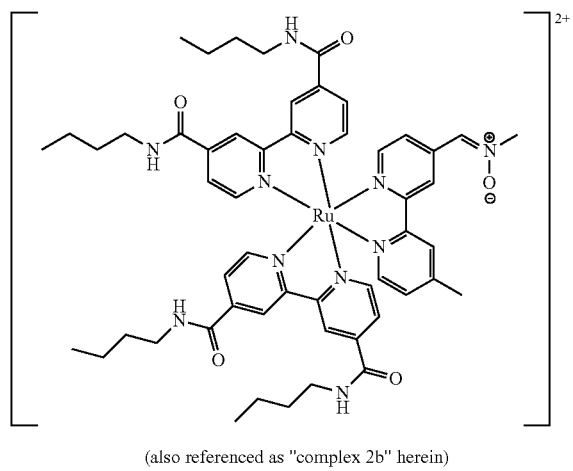

(also referenced as "complex 2b" herein)

Formula (XIVc)

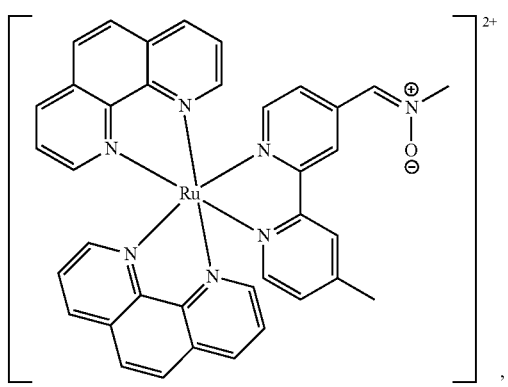

(also referenced as "complex 3b" herein)

Formula (XIVd)

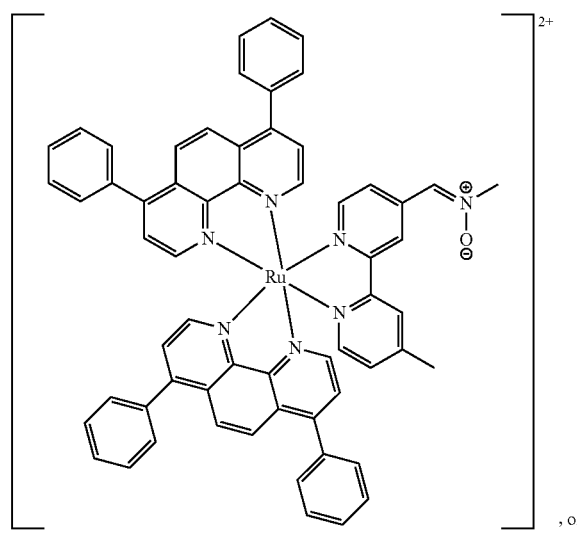

(also referenced as "complex 4b" herein)

Formula (XVa)

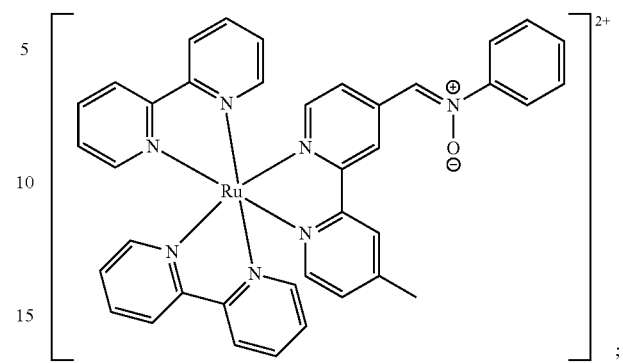

(also referenced as "complex 5b" herein);

including any salts or solvates thereof.

In particular embodiments of the present invention, the transition metal-based pyridyl complex comprises a structure selected from:

Formula (XIVa)

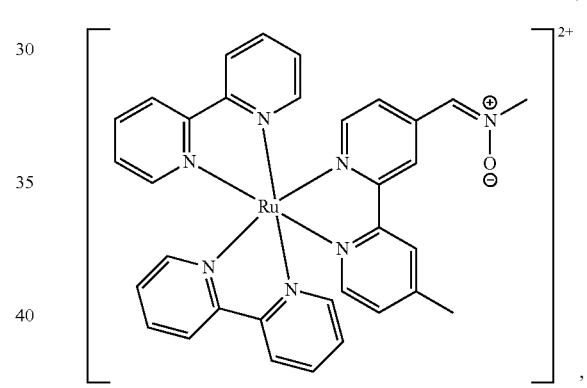

Formula (XIVb)

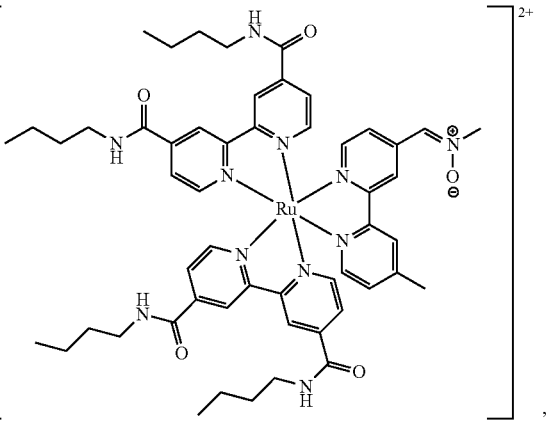

-continued

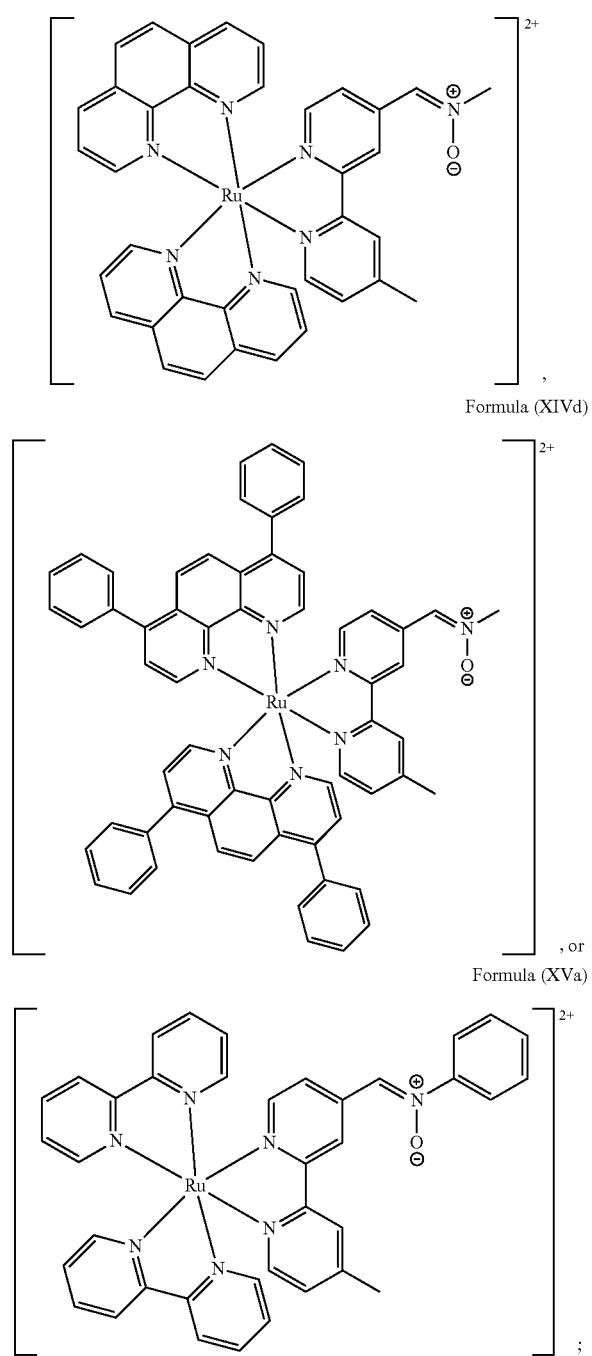

Formula (XIVc)

Formula (XIVd)

, or

Formula (XVa)

;

including any salts or solvates thereof.

In particular, the transition metal-based pyridyl complex essentially consists of a structure as described above and a counterion.

The transition metal-based pyridyl complex may be present in form of a salt, i.e., suitable counterions may be present. A counterion might affect the solubility or other physical or chemical properties of the transition metal-based pyridyl complex, wherein the exact nature of the counterion is not critical as long as it is pharmaceutically acceptable and/or not significantly toxic in the amounts used. Counterions can particularly be anions which are unlikely to bind directly to the transition metal ion, i.e., non-coordinating anions, including chloride (Cl$^-$), hexafluorophosphate (PF$_6^-$), perchlorate (ClO$_4^-$), or tetrafluoroborate (BF$_4^-$). As used herein, the term "solvate" refers to a complex of variable stoichiometry formed by a solute, i.e. the transition metal-based pyridyl complex, and a solvent. If the solvent is water, the solvate formed is a hydrate.

The transition metal-based pyridyl complex of the present invention comprises a structure of Formula (XII) or (XIV) given above, i.e., of:

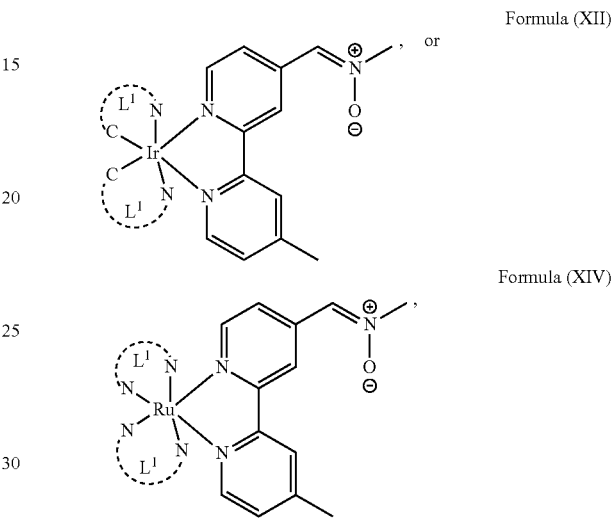

Formula (XII) , or

Formula (XIV) , may be prepared, for example, comprising steps of:
(i) providing a mixture of a pyridyl ligand of Formula (III)

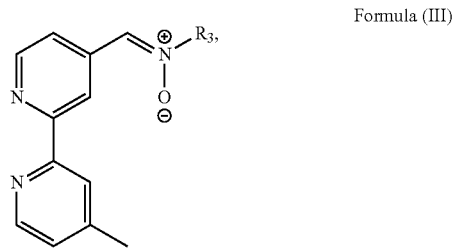

Formula (III)

and a complex comprising the transition metal and the pyridyl ligand (L$^1$) in a solvent; preferably L$^1$ is a pyridyl ligand selected from the group consisting of structures of Formula (IV) to (X), in particular L$^1$ is a cyclometalating ligand selected from a structure of Formula (IV), (V), or (VI) or L$^1$ is a polypyridyl ligand selected from a structure of Formula (VII), (VIII), (IX), or (X);
(ii) optionally adding a salt comprising the counterion; and
(iii) optionally isolating the transition metal-based pyridyl complex.

"Isolating" the transition metal-based pyridyl complex means a step of separating this complex from unreacted reactants and/or side products from the reaction mixture.

I.e., the present invention further refers to a method for preparing the transition metal-based pyridyl complex of the present invention.

The complex used in step (i) preferably comprises a structure of [Ir$_2$(L$^1$)$_4$X$_2$] with L$^1$ being a pyridyl ligand of Formula (IV) to (VI) or comprises a structure of [Ru(L¹)₂X₂] with L¹ being a pyridyl ligand of Formula (VII) to (X). "X" as used in the above complexes is a halide, in particular it is a chloride.

The mixture is preferably stirred under an inert atmosphere such as of N₂ in the dark for at least about 12 h, in particular for about 18 h. The mixture may be heated to reflux for about 12 h, in particular for about 24 h. The solvent particularly comprises a halogenated hydrocarbon and/or an aliphatic alcohol.

"Aliphatic alcohol" means an aliphatic hydrocarbon, preferably a branched or straight-chain alkane with at least one hydrogen atom being substituted with a hydroxyl group, preferably one hydrogen atom is substituted with a hydroxyl group, referenced as monohydric aliphatic alcohol. More preferably, the aliphatic alcohol is a monohydric aliphatic alcohol, still more preferably a monohydric alcohol with 1 to 2 carbon atoms, i.e., selected from MeOH, ethanol (EtOH), or mixtures thereof. The term "halogenated hydrocarbon" as used herein refers to a hydrocarbon, preferably an alkane with at least one hydrogen atom substituted with a halogen atom. Preferably, the hydrocarbon has 1 to 2 carbon atoms and two or more halogen atoms such as chlorine atoms including CHCl₃ and CH₂Cl₂. The solvent preferably essentially consists of CH₂Cl₂ and MeOH or aqueous EtOH such as 10% aqueous EtOH.

Optionally, the volume of the reaction mixture is reduced such as under reduced pressure and/or the mixture is filtered.

Step (ii) particularly comprises adding KPF₆ as a solid or a saturated aqueous solution.

Step (iii) may comprise steps of removing the solvent from the mixture such as under reduced pressure and purifying the residue by column chromatography on silica gel such as by using an eluent comprising a halogenated hydrocarbon and an aliphatic alcohol, in particular CH₂Cl₂ and MeOH. Alternatively or additionally, the purified residue may be recrystallized such as from a mixture comprising and preferably essentially consisting of dichloromethane/diethyl ether (CH₂Cl₂/Et₂O) or dichloromethane/acetonitrile/diethyl ether (CH₂Cl₂/CH₃CN/Et₂O).

The transition metal-based pyridyl complex of the present invention comprises a structure of Formula (XV), i.e., of:

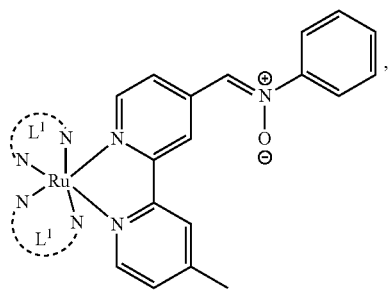

Formula (XV)

may be prepared, for example, comprising steps of:

(i) providing a mixture of a complex comprising a structure of Formula (XVI) and N-phenyl hydroxylamine in a solvent; and

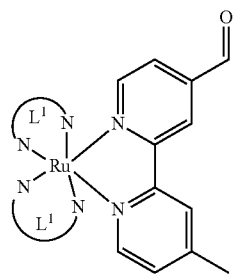

Formula (XVI)

(ii) isolating the transition metal-based pyridyl complex.

L¹ is particularly a pyridyl ligand in particular a polypyridyl ligand of Formula (VII). The solvent is particularly a halogenated hydrocarbon, preferably CH₂Cl₂. Preferably, step (i) is carried out by mixing the complex of Formula (XVI) and the N-phenyl hydroxylamine in the solvent and stirring the mixture at room temperature, i.e., at about 25±2° C. for at least about 48 h, in particular for 72 h.

Step (ii) particularly means separating the precipitate, washing the precipitate with a halogenated hydrocarbon and a dialkyl ether, in particular with CH₂Cl₂ and Et₂O and recrystallization from a mixture of a ketone and a dialkyl ether, in particular from acetone/diethyl ether ((CH₃)₂CO/Et₂O).

N-Phenyl hydroxylamine can be prepared by preparing a mixture of nitrobenzene, ammonium chloride (NH₄Cl), and zinc dust and stirring the mixture in water at room temperature, i.e., about 25±2° C. for at least about 2 h, in particular for about 4 h. The mixture can be filtered and extracted with a halogenated hydrocarbon, in particular with CH₂Cl₂. The solvent is particularly removed from the mixture and the residue is recrystallized from the mixture comprising a halogenated hydrocarbon and a dialkyl ether, in particular from CH₂Cl₂/Et₂O.

The term "biomolecule" refers to a molecule which is biologically active, i.e., a biologically active molecule particularly including biomolecules produced by a living organism or recombinant molecules produced by bacteria, viruses, plants, and animals. Biomolecules include, for example, polypeptides or proteins such as antibodies, receptor ligands, nucleic acids, and the like. The term "biologically active" describes molecule that has an effect on the organism such as on metabolic or signaling pathways, in particular has a specific function in an organism, for example, an antigen-binding activity, a receptor-binding activity, or an enzymatic activity. The biomolecule can be a targeting biomolecule. "Targeting biomolecules" are biomolecules specifically binding to a target such as the cell membrane or transmembrane proteins and/or receptors which are particularly indicative of a disease or pathological condition such as antibodies, fragments thereof, or other binding polypeptides. The biomolecule in embodiments can be selected from an antibody or fragment thereof, which can be obtained using known techniques or may be commercially available. The term biomolecules as used herein also includes biologically active compounds such as n-decylamine although the term particularly refers to biomolecules which are produced in living organisms or corresponding recombinant biomolecules.

The complementary bioorthogonal functional group coupled to the biomolecule is a strained alkyne moiety. "Coupled" means covalently linked to the biomolecule optionally via a linker, namely a group linking the strained alkyne moiety to the biomolecule. Suitable linker groups are known to one of skill in the art.

The term "alkyne" refers to a hydrocarbon having at least one carbon-carbon triple bond, wherein the term "strained alkyne" indicates that strain is present in the alkyne, in particular angle strain arising from the deformation of the —C≡C— bond angle. Strain is present in a structure if the energy is enhanced because of unfavorable bond lengths or bond angles relative to a standard. The alkyne is particularly strained by being part of a ring, for example a cycloalkyne ring with less than 10 carbon atoms, in particular with 8 or 9 carbon atoms, i.e., a cyclooctyne, a cyclononyne, or derivate thereof, namely comprising heteroatoms as ring members and/or being fused or coupled to aryl rings. The strained alkyne moiety particularly is a cyclooctyne and may be optionally substituted. The strained alkyne is particularly selected from an optionally substituted cyclooctyne, dibenzocyclooctyne, azadibenzocyclooctyne, or bicyclononyne such as bicyclo[6.1.0]nonyne. Substituents might include, for example, fluorine atoms, hydroxyl groups, and alkoxy groups. Cyclooctynes commonly applied include, for example, dibenzocyclooctyne (DIBO) and biarylazacyclooctynone (BARAC) known to one of skill in the art. In particular, the strained alkyne moiety comprises a bicyclo[6.1.0]nonyne, in particular it has a structure of Formula (XVII):

Formula (XVII)

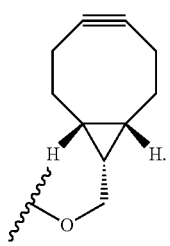

A person of skill in the art is aware of methods and means for coupling strained alkynes to biomolecules, for example, by coupling it to primary amino groups of polypeptides such as by means of chemical groups that will allow coupling of the strained alkyne moiety to the biomolecule such as isocyanates, isothiocyanates, N-hydroxysuccinimide (NHS) esters, sulfonyl chlorides, and the like. In particular, (1R, 8S,9s)-bicyclo[6.1.0]non-4-yn-9-ylmethyl N-succinimidyl carbonate of Formula (XVIII) can be used for coupling the strained alkyne moiety to the biomolecule Formula (XVIII)

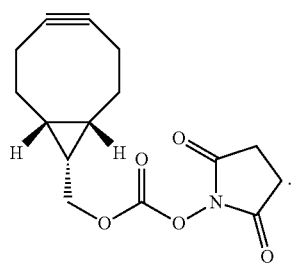

A "cycloaddition" is known to one of skill in the art as a reaction in which unsaturated molecules combine to form rings, i.e., it refers to a chemical reaction in which two or more 1-electron systems (e.g. unsaturated molecules or unsaturated parts of the same molecule) combine to form a cyclic product in which there is a net reduction of the bond multiplicity. The cycloaddition reaction between the nitrone moiety and the strained alkyne moiety is a strain-promoted alkyne-nitrone cycloaddition (SPANC) in particular leading to an N-substituted isoxazoline wherein the substituent is $R_3$ as referenced above. I.e., the cycloaddition reaction particularly follows the following Scheme 1:

Scheme 1

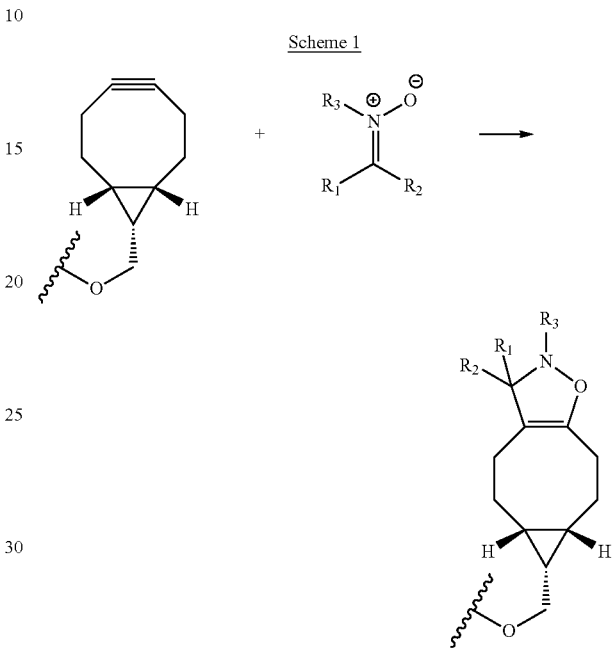

The present invention also provides a pharmaceutical composition with the luminogenic transition metal-based pyridyl complex as described above and one or more pharmaceutically tolerable excipients such as one or more of a pharmaceutically tolerable carrier, salt, buffer, solvent, diluent, or filler. Pharmaceutically tolerable excipients are those excipients which can be administered to an organism without significantly toxicity and which do not react with the transition metal-based pyridyl complex.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition according to the invention can be present in solid, semisolid, or liquid form to be administered by an oral or parenteral route to an organism such as a human.

The present invention in another aspect provides a method for bioorthogonal labeling of a biomolecule with a luminogenic transition metal-based pyridyl complex as described above. Said method comprises:

(i) introducing a biomolecule with a complementary bioorthogonal functional group coupled to the biomolecule into a living system; and (ii) introducing the luminogenic transition metal-based pyridyl complex as described above which may also be in form of a salt and/or solvate into the living system, i.e., such that a bioorthogonal reaction occurs between the nitrone moiety of the transition metal-based pyridyl complex and the complementary bioorthogonal functional group coupled to the biomolecule, namely the strained alkyne moiety.

The term "living system" encompasses an organism and a cell or a cell population isolated from an organism. An "organism" includes an animal or human, in particular a mammal such as a human. The expression "introducing into the living system" such as introducing into a cell or a cell population includes contacting a cell or a cell population with the biomolecule coupled with the complementary bioorthogonal functional group in step (i) and the transition metal-based pyridyl complex in step (ii), in particular incubating the cell or cell population with these compounds in steps (i) and (ii). If the living system is an organism, introducing the biomolecule coupled with the complementary bioorthogonal functional group in step (i) and the transition metal-based pyridyl complex in step (ii) includes administering the biomolecule with the complementary bioorthogonal functional group coupled to the biomolecule and the transition metal-based pyridyl complex to the organism such as via an oral or parenteral route. "Incubation" means applying conditions which support the cellular uptake of the biomolecule or its binding to cellular structures in the case of the biomolecule or the biomolecule coupled with the complementary bioorthogonal functional group, and conditions which support the bioorthogonal labeling in the case of the transition metal-based pyridyl complex, i.e., which support the cycloaddition reaction between the nitrone moiety of the transition metal-based pyridyl complex and the complementary bioorthogonal functional group coupled to the biomolecule.

The expression "bioorthogonal labeling" in general means that the biomolecule is recognized by a compound and that the labeled biomolecule is then capable of producing a signal that is detectable by visual or instrumental means. As used herein, it means that the biomolecule is recognized by the transition metal-based pyridyl complex accompanied by an increased luminescence of the labeled biomolecule. Namely, the luminogenic transition metal-based pyridyl complex of the present invention with its nitrone moiety undergoes cycloaddition reaction with the complementary bioorthogonal functional group coupled to the biomolecule leading to an increase, in particular a significant increase in the luminescence, in particular phosphorescence, such as an emission enhancement $(I/I_0)$ ratio of at least 7, in particular at least 8, further preferred at least 10, and still further preferred of more than 10, wherein I and $I_0$ are the emission intensities of the transition metal-based pyridyl complex of the present invention in the presence and absence, respectively, of the biomolecule under the same conditions such as in aerated potassium phosphate buffer (about 50 mM, pH about 7.4) containing 10% (v/v) MeOH or 1% (v/v) DMSO at about 25±2° C. (about 298 K) with about 10 μM of the transition metal-based pyridyl complex. The concentration of the biomolecule may be, for example, between about 2 μM and about 20 μM.

For example, the living system is a cell population and the cells are contacted with the biomolecule in step (i) and incubated for at least about 15 min, in particular for at least about 30 min and at about 37° C. The cell population is then contacted with the transition metal-based pyridyl complex of the present invention and incubated such as for at least about 30 min, in particular for at least about 1 h such as about 12 h at about 37° C.

The concentration of the luminogenic transition metal-based pyridyl complex can be, for example, between about 1 μM and 100 μM such as about 5 μM to about 40 μM. The concentration of the biomolecule used in step (i) depends on the specific biomolecule and may be, for example, about 2 μM to about 500 μM.

The method may further comprise a step (iii) of imaging the living system in particular with luminescence, preferably phosphorescence detection with ex vivo or in vivo imaging methods including fluorescence microscopy such as confocal microscopy, in particular laser scanning confocal microscopy (LSCM).

The complementary bioorthogonal functional group coupled to the biomolecule used in step (i) is preferably a strained alkyne moiety, in particular an optionally substituted cycloalkyne such as a bicyclo[6.1.0]nonyne, in particular the complementary bioorthogonal functional group comprises a structure of Formula (XVII):

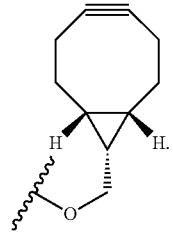

Formula (XVII)

The biomolecule is preferably a targeting biomolecule. The biomolecule is preferably a polypeptide, in particular a targeting polypeptide.

The transition metal-based pyridyl complex used in step (ii) preferably comprises a structure of Formula (XI), in particular of Formula (XII):

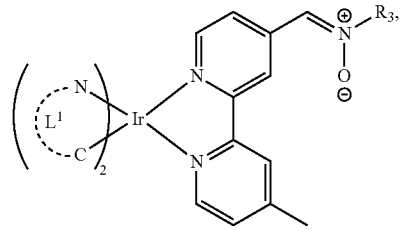

Formula (XI)

in particular

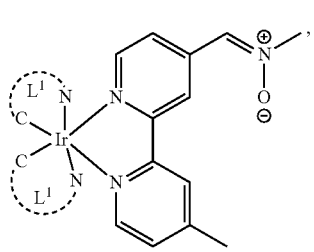

Formula (XII)

with $R_3$ being as defined above and $L^1$ being a pyridyl ligand in particular a cyclometalating ligand particularly selected from a structure of:

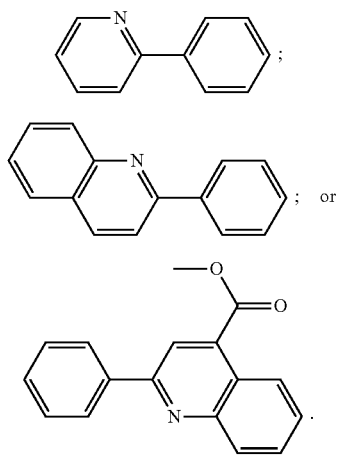
Formula (IV);

Formula (V); or

Formula (VI).

In another preferred embodiment, the transition metal-based pyridyl complex used in step (ii) comprises a structure of Formula (XIII), in particular of Formula (XIV) or Formula (XV):

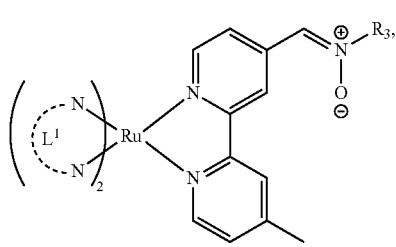
Formula (XIII)

in particular

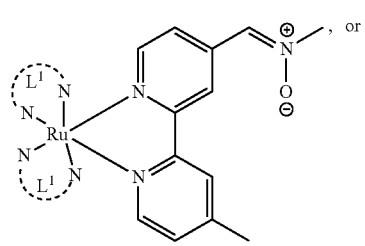
Formula (XIV), or

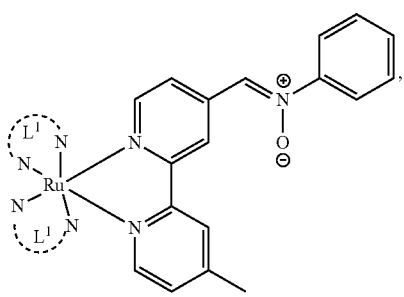
Formula (XV), with $R_3$ being as defined above and $L^1$ being a pyridyl ligand in particular a polypyridyl ligand selected from a structure of:

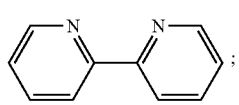
Formula (VII);

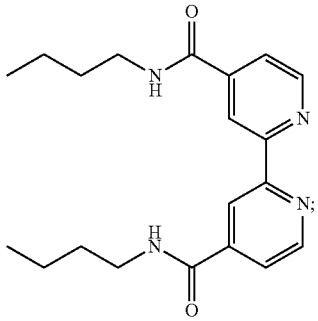
Formula (VIII);

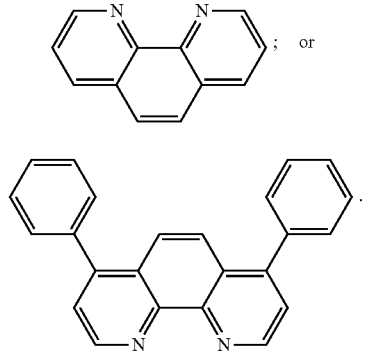
Formula (IX); or

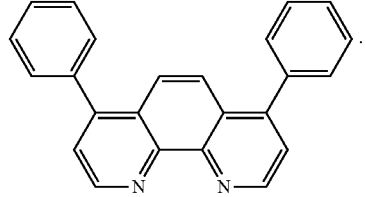
Formula (X).

Particular transition metal-based pyridyl complexes used in step (ii) comprises a structure of Formula (XII) with $L^1$ being a pyridyl ligand in particular a cyclometalating ligand selected from a structure of Formula (IV), (V), or (VI), or a structure of Formula (XIV) with $L^1$ being a pyridyl ligand in particular a polypyridyl ligand selected from a structure of Formula (VII), (VIII), (IX), or (X), or a structure of Formula (XV) with $L^1$ being a pyridyl ligand in particular a polypyridyl ligand selected from a structure of Formula (VII). In further preferred embodiments, the transition metal-based pyridyl complex comprises a structure of Formula (XIV) with $L^1$ being a pyridyl ligand in particular a polypyridyl ligand selected from a structure of Formula (VII), (VIII), (IX), or (X) or a structure of Formula (XV) with $L^1$ being a pyridyl ligand in particular a polypyridyl ligand selected from a structure of Formula (VII).

Most preferably, the transition metal-based pyridyl complex comprises a structure selected from the group consisting of:

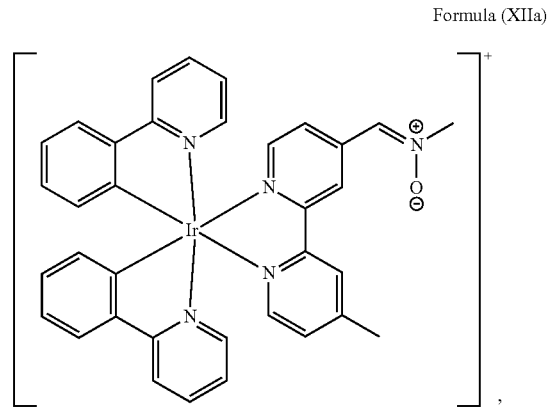
Formula (XIIa)

(also referenced as "complex 1a" herein)

-continued
Formula (XIIb)
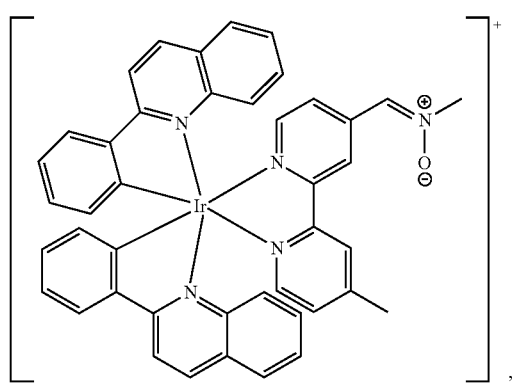
(also referenced as "complex 2a" herein)
Formula (XIIc)
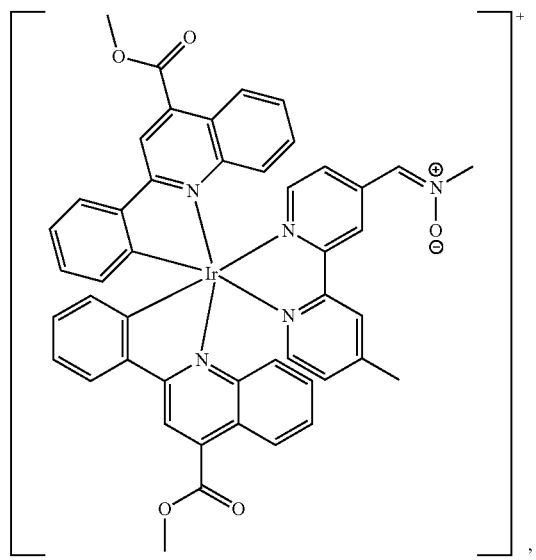
(also referenced as "complex 3a" herein)
Formula (XIVa)
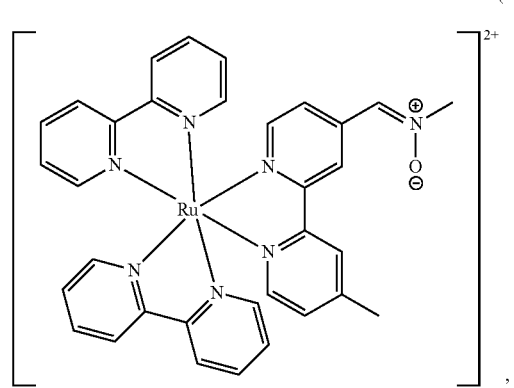
(also referenced as "complex 1b" herein)
Formula (XIVb)
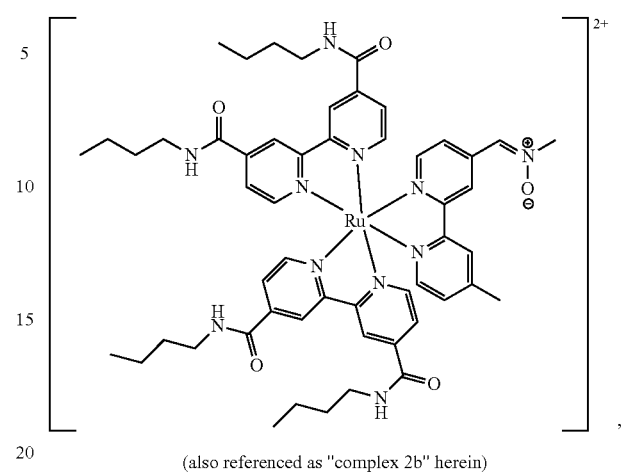
(also referenced as "complex 2b" herein)
Formula (XIVc)
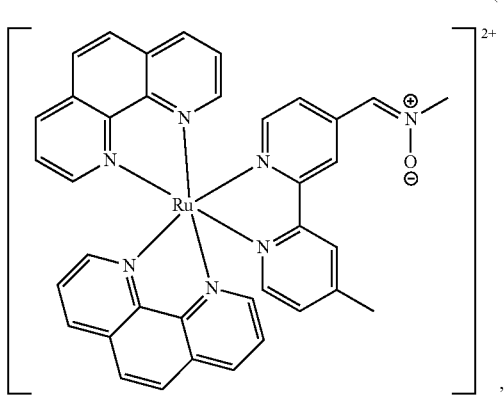
(also referenced as "complex 3b" herein)
Formula (XIVd)
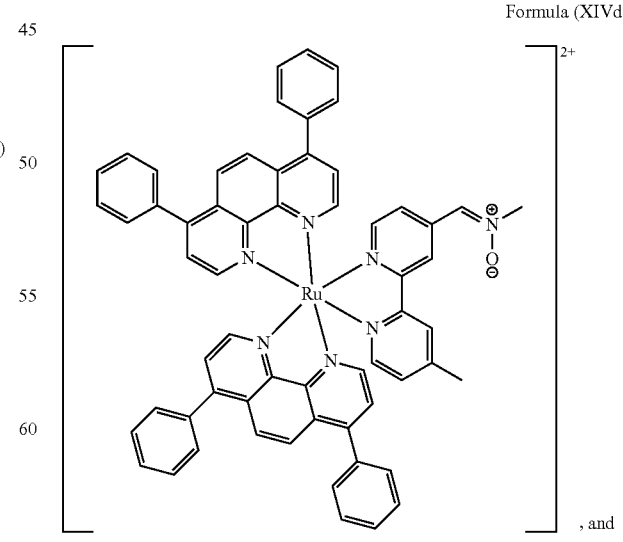
(also referenced as "complex 4b" herein)
, and Formula (XVa)

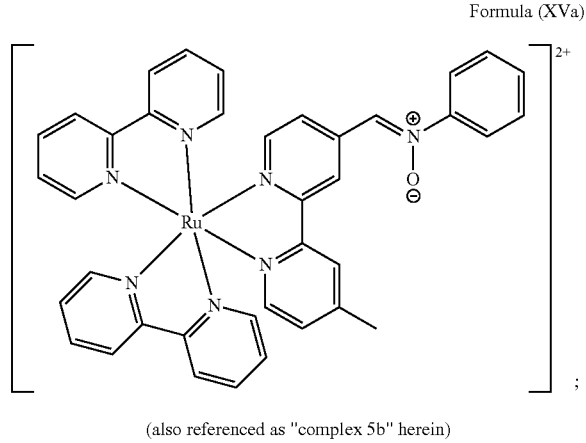

(also referenced as "complex 5b" herein)

including any salts or solvates thereof.

In particular, the transition metal-based pyridyl complex essentially consists of a structure as described above and a counterion.

Further provided with the present invention is a method for staining of a cell structure comprising:

(i) introducing N-[(1R,8S,9s)-bicyclo[6.1.0]non-4-yn-9-ylmethyloxycarbonyl]-1-aminodecane (BCN-C10) of Formula (XIX) into a cell population:

Formula (XIX)

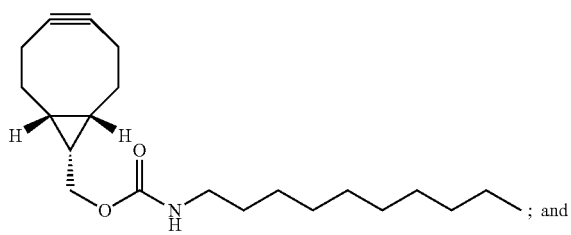

; and and (ii) introducing the luminogenic transition metal-based pyridyl complex as described above which may be in form of a salt and/or solvate into the cell population, i.e., such that a bioorthogonal reaction occurs between the nitrone moiety of the transition metal-based pyridyl complex and the strained alkyne moiety of the compound of Formula (XIX).

Steps (i) and (ii) particularly comprises incubating the cell population after contacting the cell population with the biomolecule in step (i), in particular, such that the biomolecule can be taken up by the cells or can bind to cellular structures and in step (ii) with the transition metal-based pyridyl complex, in particular, such that the bioorthogonal reaction can occur between the nitrone moiety of the transition metal-based pyridyl complex and the complementary bioorthogonal functional group coupled to the biomolecule, i.e., the strained alkyne moiety of the compound of Formula (XIX).

The cell structure can be the cell membrane or the cytosol, in particular it is the cell membrane. More preferably, the cell structure is the cell membrane and the luminogenic transition metal-based pyridyl complex comprises a structure selected from:

Formula (XIVb)

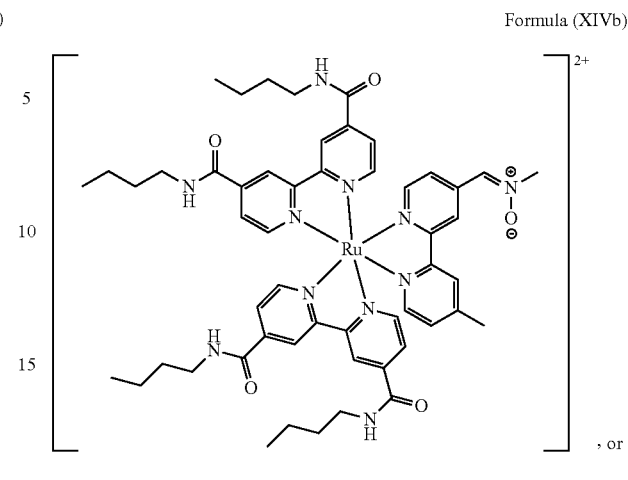

(also referenced as "complex 2b" herein)

, or

Formula (XVa)

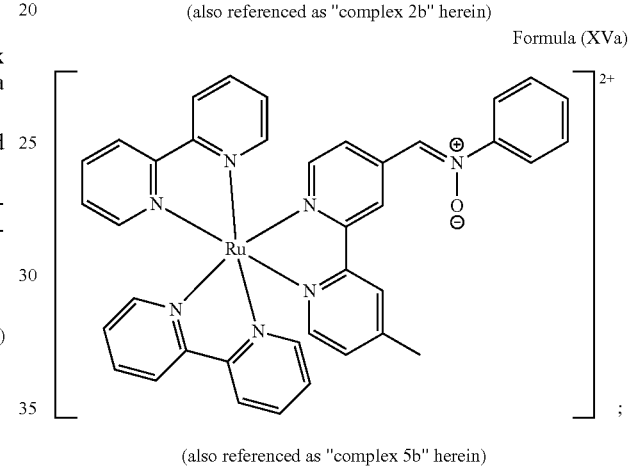

(also referenced as "complex 5b" herein)

including any salts and solvates thereof.

The method may further comprise a step (iii) of imaging the cell population in particular with luminescence, preferably phosphorescence detection such as with fluorescence microscopy such as confocal microscopy, in particular LSCM.

BCN-C10 can be prepared, for example, by preparing a mixture of n-decylamine, BCN—NHS of Formula (XVIII), and triethyl amine ($Et_3N$) in a solvent which is particularly a halogenated hydrocarbon, more preferably it is $CH_2Cl_2$ and stirring the mixture at room temperature, i.e., at about 25±2° C., under an inert atmosphere such as of $N_2$ in the dark for about 18 h. The reaction is preferably quenched with water and the mixture is then extracted with a halogenated hydrocarbon, more preferably with $CH_2Cl_2$. The solvent is then preferably removed from the mixture such as under reduced pressure. The residue is preferably purified by column chromatography on silica gel using an aliphatic alkane, in particular n-hexane as the eluent.

The present invention provides in another aspect a method for in vivo imaging of an organism comprising:

(i) administering an effective amount of a biomolecule with a complementary bioorthogonal functional group coupled to the biomolecule to the organism;

(ii) administering an effective amount of a luminogenic transition metal-based pyridyl complex as described above which may also be in form of a salt and/or solvate to said organism, i.e., such that the bioorthogonal reaction occurs between the nitrone moiety of the transition metal-based pyridyl complex and the complementary bioorthogonal functional group coupled to the biomolecule, namely the strained alkyne moiety; and (iii) imaging the organism, wherein a signal indicates the presence of a labeled biomolecule.

The term "effective amount" means an amount of the biomolecule and the luminogenic transition metal-based pyridyl complex sufficient to obtain signals in step (iii) for imaging the organism. The organism is preferably an animal or human, in particular a mammal such as a human.

In particular, the biomolecule in step (i) is a targeting biomolecule that is able to bind to a receptor, having enzyme activity, or able to bind to the cell membrane. The signal, i.e., the presence of the labeled biomolecule may indicate a disease or pathological condition of the organism such as inflammation, cancer, heart disease, atherosclerosis, angiogenesis, or intravascular thrombus formation.

The complementary bioorthogonal functional group coupled to the biomolecule used in step (i) is preferably a strained alkyne moiety, in particular an optionally substituted cycloalkyne such as a bicyclo[6.1.0]nonyne, in particular the complementary bioorthogonal functional group comprises a structure of Formula (XVII):

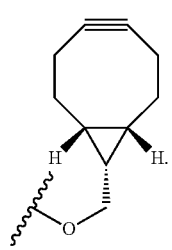

Formula (XVII)

The transition metal-based pyridyl complex used in step (ii) preferably comprises a structure of Formula (XI), in particular of Formula (XII):

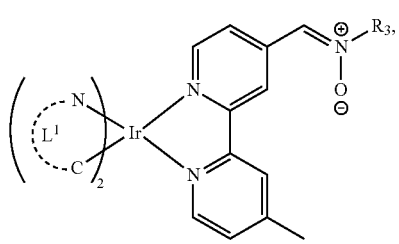

Formula (XI)

in particular

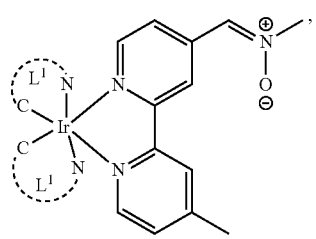

Formula (XII)

with $R_3$ being as defined above and $L^1$ being a pyridyl ligand in particular a cyclometalating ligand particularly selected from a structure of:

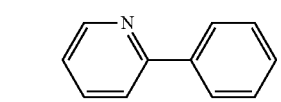

Formula (IV)

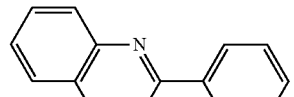

Formula (V)

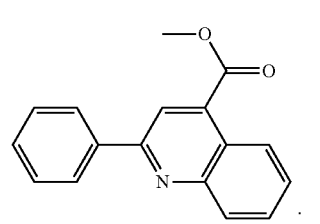

; or

Formula (VI)

.

In another preferred embodiment, the transition metal-based pyridyl complex used in step (ii) comprises a structure of Formula (XIII), in particular of Formula (XIV) or Formula (XV):

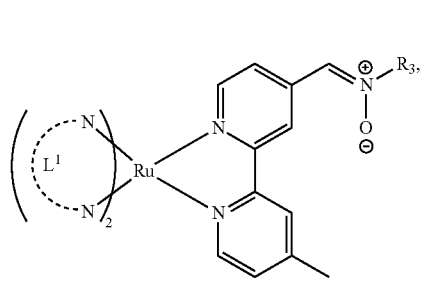

Formula (XIII)

in particular

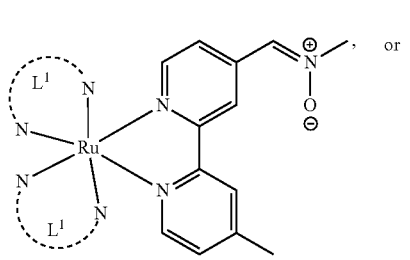

Formula (XIV)

, or

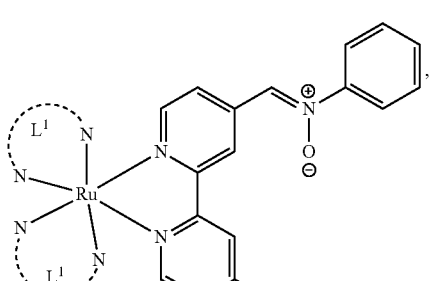

Formula (XV)

, with $R_3$ being as defined above and $L^1$ being a pyridyl ligand in particular a polypyridyl ligand particularly selected from a structure of:

Formula (VII)

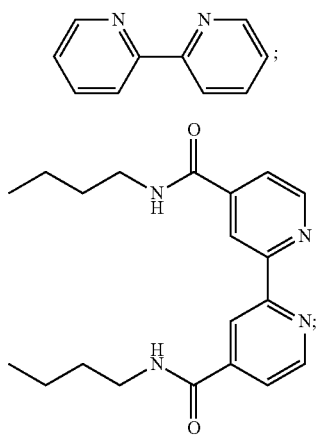

Formula (VIII)

Formula (IX)

; or

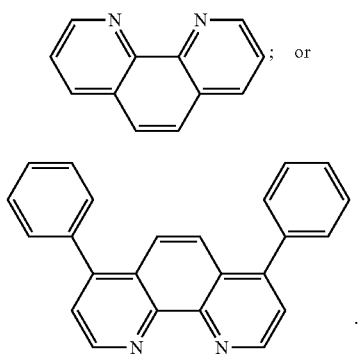

Formula (X)

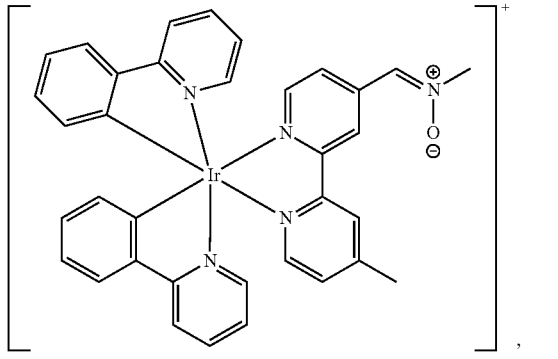

Particular transition metal-based pyridyl complexes used in step (ii) comprises a structure of Formula (XII) with $L^1$ being a pyridyl ligand in particular a cyclometalating ligand selected from a structure of Formula (IV), (V), or (VI), or a structure of Formula (XIV) with $L^1$ being a pyridyl ligand in particular a polypyridyl ligand selected from a structure of Formula (VII), (VIII), (IX), or (X), or a structure of Formula (XV) with $L^1$ being a pyridyl ligand selected from a structure of Formula (VII). In further preferred embodiments, the transition metal-based pyridyl complex comprises a structure of Formula (XIV) with $L^1$ by a pyridyl ligand in particular a polypyridyl ligand selected from a structure of Formula (VII), (VIII), (IX), or (X) or a structure of Formula (XV) with $L^1$ being a pyridyl ligand selected from a structure of Formula (VII).

Most preferably, the transition metal-based pyridyl complex comprises a structure selected from the group consisting of:

Formula (XIIa)

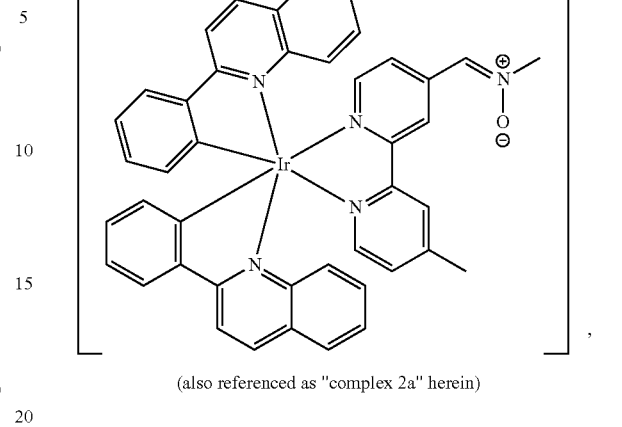

(also referenced as "complex 1a" herein)

Formula (XIIb)

(also referenced as "complex 2a" herein)

Formula (XIIc)

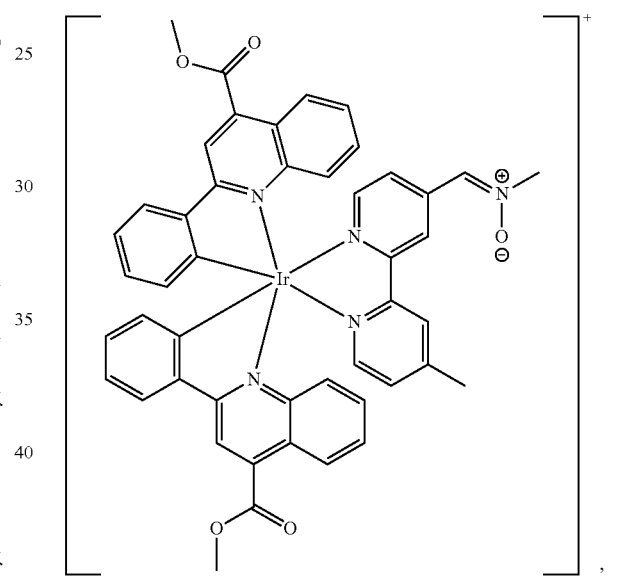

(also referenced as "complex 3a" herein)

Formula (XIVa)

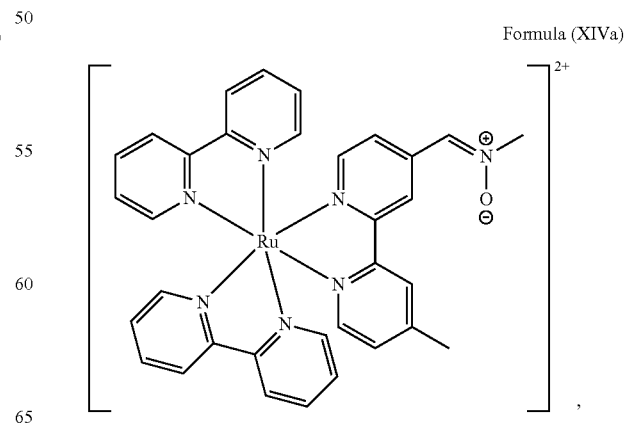

(also referenced as "complex 1b" herein)

Formula (XIVb)

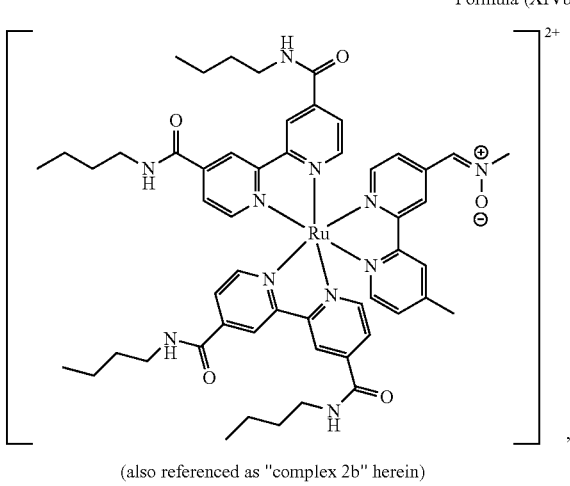

(also referenced as "complex 2b" herein)

Formula (XIVc)

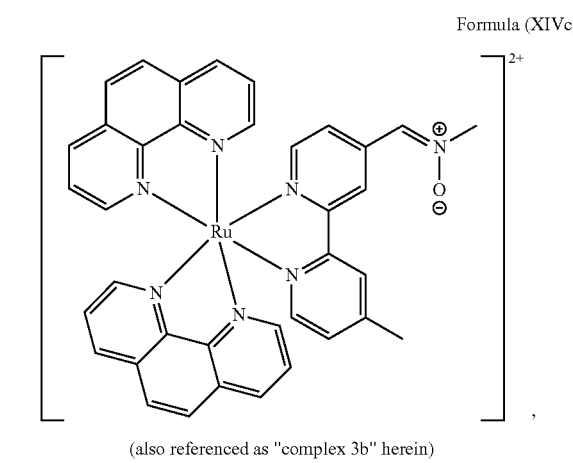

(also referenced as "complex 3b" herein)

Formula (XIVd)

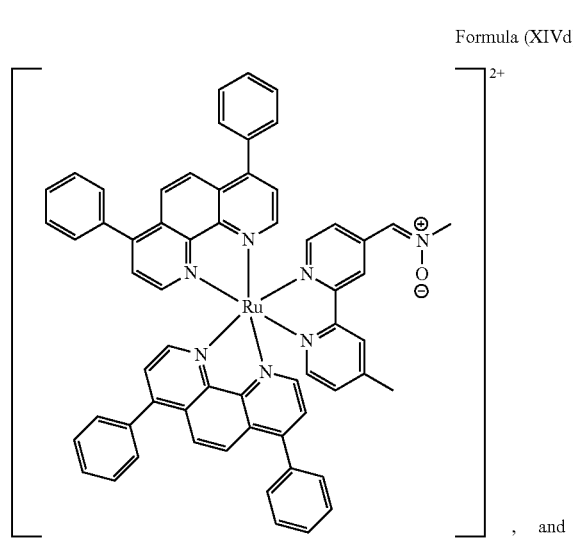

(also referenced as "complex 4b" herein)

Formula (XVa)

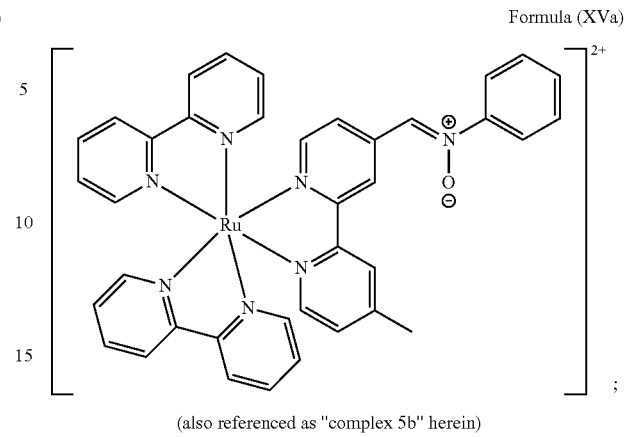

(also referenced as "complex 5b" herein)

including any salts or solvates thereof.

In particular, the transition metal-based pyridyl complex essentially consists of a structure as described above and a counterion.

Step (iii) of imaging the organism particularly comprises luminescence, in particular phosphorescence detection which methods are known to one of skill in the art including ex vivo or in vivo imaging methods like fluorescence microscopy such as confocal microscopy, in particular LSCM. Imaging the organism may include imaging an organ, a tissue, a part of the organism, or whole body imaging.

The present invention further refers to a kit for in vivo imaging of an organism comprising:

(i) an effective amount of a biomolecule with a complementary bioorthogonal functional group coupled to the biomolecule;

(ii) an effective amount of a luminogenic transition metal-based pyridyl complex as described above such as in form of a salt and/or solvate; and (iii) optionally pharmaceutically tolerable excipients.

The biomolecule is particularly a targeting biomolecule. The pharmaceutically tolerable excipients particularly include one or more of a pharmaceutically tolerable carrier, salt, buffer, solvent, diluent, or filler. The biomolecule and the luminogenic transition metal-based pyridyl complex according to the invention can be present in solid, semisolid, or liquid form to be administered by an oral or parenteral route to an organism such as a human.

In particular, the biomolecule in the kit is a targeting biomolecule able to bind to a receptor, having enzyme activity, or able to bind to the cell membrane. The signal, i.e., the presence of a labeled biomolecule may indicate a disease or pathological condition of the organism such as inflammation, cancer, heart disease, atherosclerosis, angiogenesis, or intravascular thrombus formation.

The complementary bioorthogonal functional group coupled to the biomolecule is preferably a strained alkyne moiety, in particular an optionally substituted cycloalkyne such as a bicyclo[6.1.0]nonyne, in particular the complementary bioorthogonal functional group comprises a structure of Formula (XVII):

Formula (XVII)

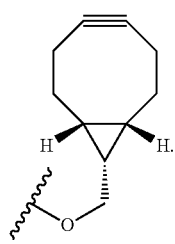

The transition metal-based pyridyl complex in the kit preferably comprises a structure of Formula (XI), in particular of Formula (XII):

Formula (XI)

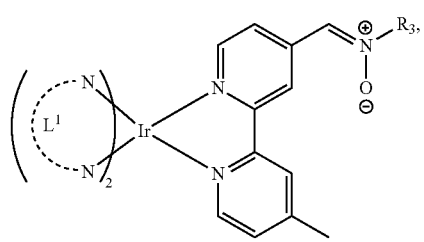

in particular

Formula (XII)

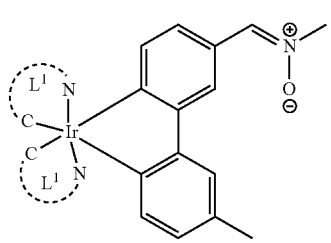

with $R_3$ being as defined above and $L^1$ being a pyridyl ligand in particular a cyclometalating ligand particularly selected from a structure of:

Formula (IV)

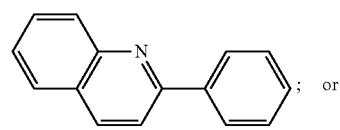

Formula (V)

; or

Formula (VI)

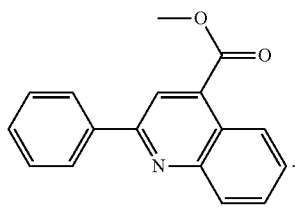

In another preferred embodiment, the transition metal-based pyridyl complex comprises a structure of Formula (XIII), in particular of Formula (XIV) or Formula (XV):

Formula (XIII)

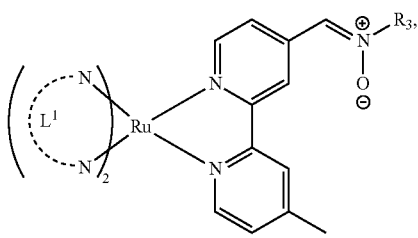

in particular

Formula (XIV)

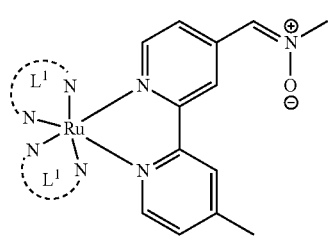

, or

Formula (XV)

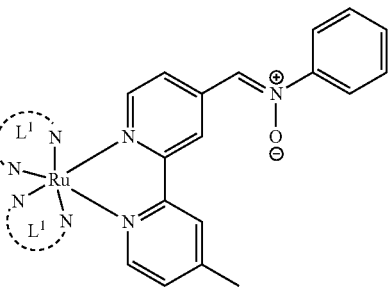

with $R_3$ being as defined above and $L^1$ being a pyridyl ligand in particular a polypyridyl ligand particularly selected from a structure of:

Formula (VII)

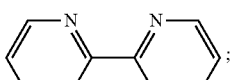

Formula (VIII)

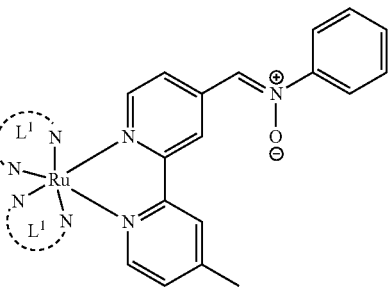

Formula (IX)

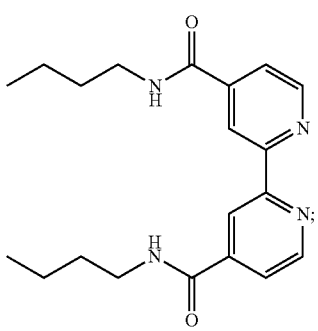

; or

Formula (X)

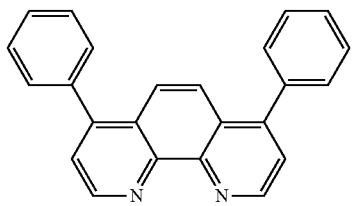

Particular transition metal-based pyridyl complexes in the kit comprise a structure of Formula (XII) with $L^1$ being a pyridyl ligand in particular a cyclometalating ligand selected from a structure of Formula (IV), (V), or (VI), or a structure of Formula (XIV) with $L^1$ being a pyridyl ligand in particular a polypyridyl ligand selected from a structure of Formula (VII), (VIII), (IX), or (X), or a structure of Formula (XV) with $L^1$ being a pyridyl ligand in particular a polypyridyl ligand selected from a structure of Formula (VII). In further preferred embodiments, the transition metal-based pyridyl complex comprises a structure of Formula (XIV) with $L^1$ being a pyridyl ligand in particular a polypyridyl ligand selected from a structure of Formula (VII), (VIII), (IX), or (X) or a structure of Formula (XV) with $L^1$ being a pyridyl ligand in particular a polypyridyl ligand selected from a structure of Formula (VII).

Most preferably, the transition metal-based pyridyl complex comprises a structure selected from the group consisting of:

Formula (XIIa)

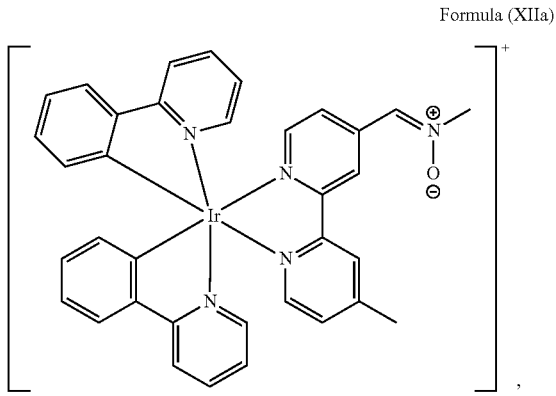

(also referenced as "complex 1a" herein)

Formula (XIIb)

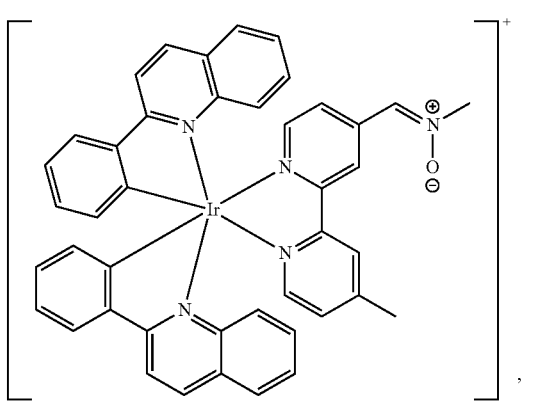

(also referenced as "complex 2a" herein)

Formula (XIIc)

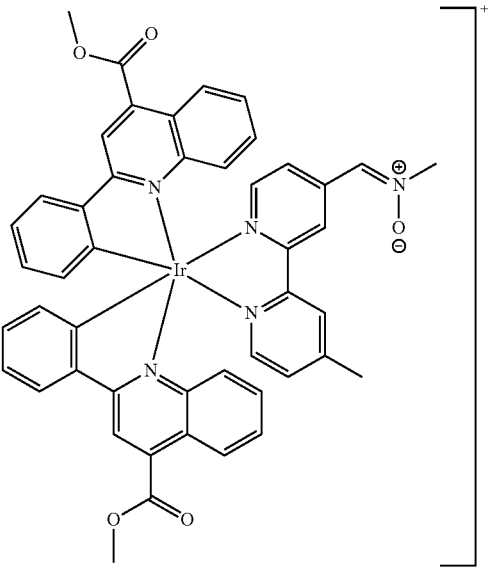

(also referenced as "complex 3a" herein)

Formula (XIVa)

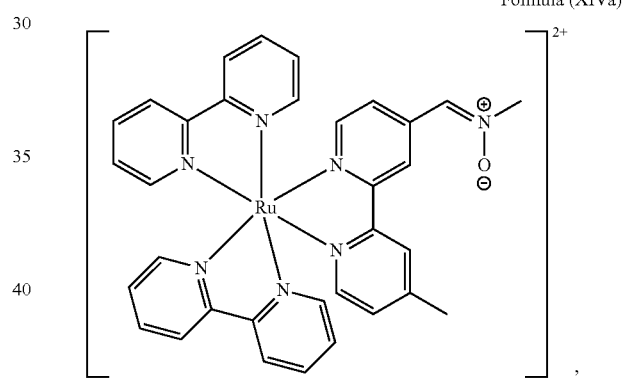

(also referenced as "complex 1b" herein)

Formula (XIVb)

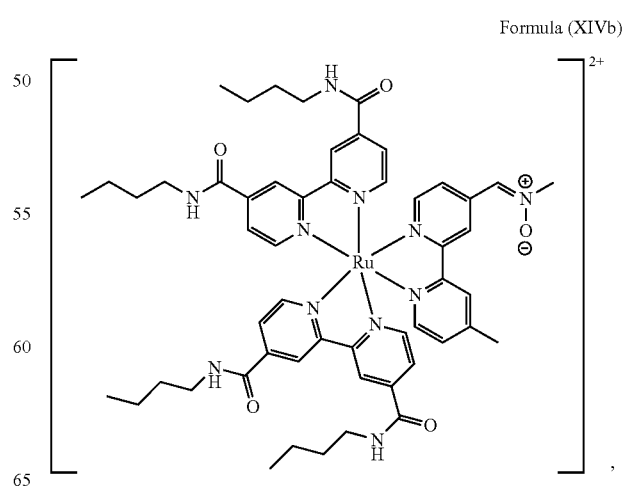

(also referenced as "complex 2b" herein)

-continued

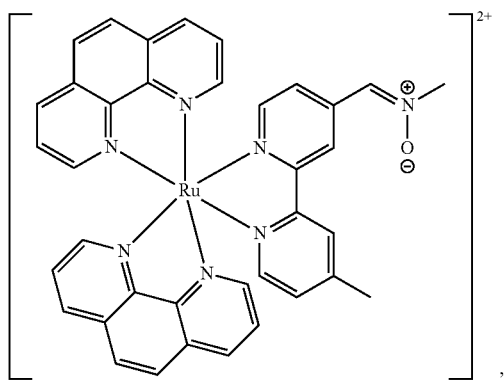

(also referenced as "complex 3b" herein)

Formula (XIVc)

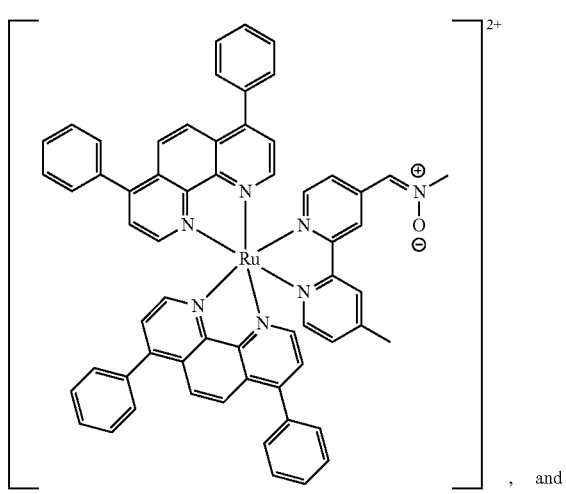

(also referenced as "complex 4b" herein)

Formula (XIVd)

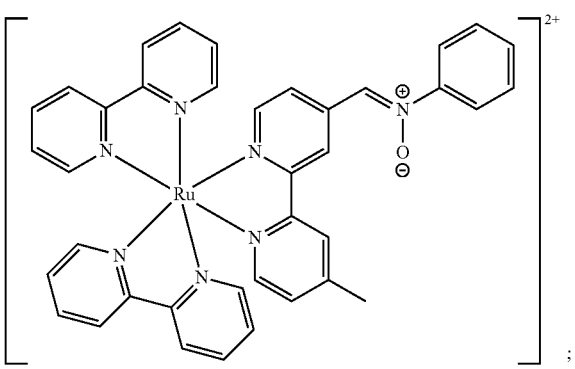

(also referenced as "complex 5b" herein)

Formula (XVa)

including any salts or solvates thereof.

In particular, the transition metal-based pyridyl complex essentially consists of a structure as described above and a counterion.

EXAMPLES

Materials and Reagents Used

All solvents were of analytical reagent grade and purified according to standard procedures. N-Methyl hydroxylamine hydrochloride, NaHCO$_3$, MgSO$_4$, nitrobenzene, zinc dust, KPF$_6$, hydrogen peroxide (H$_2$O$_2$), tertt-butyl hydroperoxide ($^t$BuOOH), NaClO, KO$_2$, [(NH$_4$)$_2$Fe(SO$_4$)$_2$].6H$_2$O, NaNO$_2$, NaNO$_3$, cysteine (Cys), glutathione (GSH), n-decylamine, and Et$_3$N were purchased from Acros. 2-Phenylpyridine (Hppy), 2-phenylquinoline (Hpq), 2,2'-bipyridine (bpy), 1,10-phenanthroline (phen), (4,7-diphenyl-1,10-phenanthroline (Ph$_2$-phen), (1R,8S,9s)-bicyclo[6.1.0]non-4-yn-9-ylmethanol (BCN—OH), (1R,8S,9s)-bicyclo[6.1.0]non-4-yn-9-ylmethyl-N-succinimidyl carbonate (BCN—NHS) and 3-(4,5-dimethylthiazol-2-yl)-2,5-diphenyltetrazolium bromide (MTT) were purchased from Sigma-Aldrich. Bovine serum albumin (BSA) was purchased from Calbiochem and used as received. All these chemicals were used without further purification. Methyl 2-phenyl-4-quinolinecarboxylate (Hpqe) (Peek, B. M. et al., Int. J. Pept. Protein Res. 1991, 38, 114), the iridium(III) dimers [Ir$_2$(N^C)$_4$Cl$_2$] (HN^C=Hppy, Hpq, and Hpqe) (Smith, R. A. et al., Dalton Trans. 2013, 42, 10347), 4-carboxylaldehyde-4'-methyl-2,2'-bipyridine (bpy-CHO) (Lo, K. K.-W. et al., Inorg. Chem. 2003, 42, 6886, Peek, B. M. et al., Int. J. Peptide Protein Res. 2009, 38, 114), 4,4'-bis(n-butylaminocarbonyl)-2,2'-bipyridine (bpyC4) (Zhang, K. Y. and Lo, K. K.-W., Inorg. Chem. 2009, 48, 6011), cis-[Ru(N^N)$_2$Cl$_2$].2H$_2$O (N^N=bpy, bpyC4, phen, and Ph$_2$-phen) (Sullivan, B. P. et al., Inorg. Chem. 1978, 17, 3334), and [Ru(bpy)$_2$(bpy-CHO)](PF$_6$)$_2$ (Li, M.-J. Et al., J. Inorg. Biochem., 2011, 105, 420) were prepared according to literature procedures. PD-10 size-exclusion columns were purchased from GE Healthcare. YM-50 microcon filters were purchased from Millipore. All buffer components were of biological grade and used as received. Autoclaved Milli-Q water was used for the preparation of the aqueous solutions. Chinese hamster ovary (CHO)-K1 and HeLa cells were obtained from American Type Culture Collection. Novex® sharp pre-stained protein standard, F-12 nutrient mixture, Dulbecco's modified Eagle's medium (DMEM), phosphate-buffered saline (PBS), fetal bovine serum (FBS), trypsin-EDTA, penicillin/streptomycin, and Cell-Mask Deep Red Plasma Membrane Stain were purchased from Invitrogen. The growth medium for cell culture of the CHO-K1 cells contained F-12 nutrient mixture with 10% FBS and 1% penicillin/streptomycin, and that for cell culture of the HeLa cells contained DMEM with 10% FBS and 1% penicillin/streptomycin.

Instrumentation and Methods Applied $^1$H and $^{13}$C NMR spectra were recorded on Bruker 300, 400, and 600 MHz AVANCE III spectrometers at 298 K using deuterated solvents. Chemical shifts (δ, ppm) were reported relative to tetramethylsilane (TMS). Positive-ion electrospray ionization (ESI) mass spectra were recorded on a Perkin Elmer Sciex API 365 mass spectrometer at 298 K. IR spectra of the samples in KBr pellets were recorded in the range of 4000-400 cm$^{-1}$ using a Perkin Elmer FTIR-1600 spectrophotometer. Elemental analyses were carried out on an Elementar Analysensysteme GmbH Vario MICRO elemental analyzer.

Electronic absorption spectra were recorded on an Agilent 8453 diode array spectrophotometer. Steady-state emission spectra were recorded on a HORIBA JOBIN YVON Fluorolog TCSPC spectrofluorometer. Unless specified otherwise, all solutions for photophysical studies were degassed with no fewer than four successive freeze-pump-thaw cycles and stored in a 10-cm$^3$ round bottomed flask equipped with a side-arm 1-cm fluorescence cuvette and sealed from the atmosphere by a Rotaflo HP6/6 quick-release Teflon stopper. Luminescence quantum yields were measured by the optically dilute method (Demas, J. N. and Crosby, G. A., J. Phys.

Chem. 1971, 75, 991) using an aerated aqueous solution of [Ru(bpy)$_3$]Cl$_2$ ($\phi_{em}$=0.028, $\lambda_{ex}$=455 nm) as the standard solution (Wallace, L. and Rillema, D. P., Inorg. Chem., 1993, 32, 3836). The concentrations of the standard and sample solutions were adjusted until the absorbance at 455 nm was 0.1. The emission lifetimes were measured on a HORIBA JOBIN YVON Fluorolog TCSPC spectrofluorometer in the Fast MCS lifetime mode with a NanoLED N-375 as the excitation source.

N-[(1R,8S,9s)-Bicyclo[6.1.0]non-4-yn-9-ylmethyl-oxycarbonyl]-1-aminodecane (BCN-C10) of Formula (XIX)

This compound has been prepared as follows:

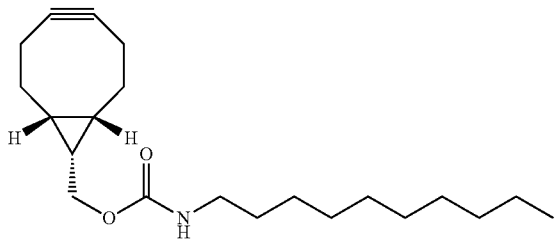 [SMILES: CCCCCCCCCCNC(=O)OC[C@@H]1[C@@H]2CCC#CCC[C@@H]21]

To a solution of n-decylamine (10 µL, 0.05 mmol) in CH$_2$Cl$_2$ (5 mL) were added Et$_3$N (16 µL, 0.11 mmol) and BCN—NHS (15 mg, 0.05 mmol), and the mixture was stirred at room temperature under an inert atmosphere of N$_2$ in the dark for 18 h. The reaction was then quenched with H$_2$O (10 mL). The product was extracted with CH$_2$Cl$_2$ (10 mL×3) and the combined organic extract was dried over MgSO$_4$, filtered, and the solvent was removed under reduced pressure. The residue was purified by column chromatography on silica gel using n-hexane as the eluent. The solvent was removed under reduced pressure and the product was subsequently isolated as yellowish oil. Yield: 16 mg (87%). $^1$H NMR (400 MHz, CDCl$_3$, 298 K, TMS): δ 4.67 (s, 1H), 4.16 (d, J=8.0 Hz, 2H), 3.18 (d, J=6.4 Hz, 2H), 2.34-2.21 (m, 6H), 1.68-1.59 (m, 2H), 1.52-1.45 (m, 1H), 1.44-1.37 (m, 16H), 0.99-0.94 (m, 2H), 0.89 (t, J=6.8 Hz, 3H). $^{13}$C NMR (100 MHz, CDCl$_3$, 298 K, TMS): δ 156.7, 98.8, 62.6, 41.1, 31.9, 30.0, 29.5, 29.3, 29.1, 26.8, 22.7, 21.4, 20.1, 17.8, 14.1. Positive-ion ESI-MS ion cluster at m/z 334 [M+H]$^+$.

4-((Methyl(oxido)imino)methyl)-4'-methyl-2,2'-bipyridine (bpy-nitrone-Me) of Formula (III) with R$_3$ being a methyl group This compound has been prepared as follows: A mixture of bpy-CHO (214 mg, 1.08 mmol), N-methyl hydroxylamine hydrochloride (182 mg, 2.16 mmol), and NaHCO$_3$ (545 mg, 6.48 mmol) in CH$_2$Cl$_2$/H$_2$O (8 mL) (1:1, v/v) was stirred under an inert atmosphere of N$_2$ in the dark for 18 h. The mixture was extracted with CH$_2$Cl$_2$ (50 mL×3) and the combined organic extract was dried over MgSO$_4$, filtered, and the solvent was removed under reduced pressure. The product was subsequently isolated as a white solid. Yield: 204 mg (83%). $^1$H NMR (300 MHz, acetone-d$_6$, 298 K, TMS): δ 9.02 (s, 1H; H3 of bpy), 8.73 (d, J=3.9 Hz, 1H; H6 of bpy), 8.54 (d, J=3.6 Hz, 1H; H6' of bpy), 8.36-8.33 (m, 2H; H5 and H3' of bpy), 7.98 (s, 1H; CH=N of nitrone moiety of bpy-nitrone-Me), 7.27 (d, J=3.6 Hz, 1H; H5' of bpy), 3.96 (s, 3H; CH$_3$ of nitrone moiety of bpy-nitrone-Me), 2.47 (s, 3H; CH$_3$ of pyridyl ring of bpy-nitrone-Me). $^{13}$C NMR (150 MHz, acetone-d$_6$, 298 K, TMS): δ 156.7, 155.7, 149.6, 149.0, 147.9, 138.8, 132.3, 124.7, 121.3, 120.4, 118.4, 54.5, 20.2. IR (KBr) ṽ/cm$^{-1}$: 1590 (C=N), 1179 (N-0). MS (ESI, positive-ion mode): m/z: 228 [M+H]$^+$.

N-Phenyl Hydroxylamine

This compound was prepared as follows: A mixture of nitrobenzene (1 g, 8.13 mmol), NH$_4$Cl (500 mg, 9.35 mmol), and zinc dust (1.18 g, 17.89 mmol) was stirred in H$_2$O (15 mL) at room temperature for 4 h. The solution was filtered and extracted with CH$_2$Cl$_2$ (50 mL×3). The combined organic phase was dried over MgSO$_4$, filtered, and the solvent was removed under reduced pressure to give a yellow solid. Subsequent recrystallization from CH$_2$Cl$_2$/Et$_2$O afforded the product as a pale yellow solid. Yield: 530 mg (60%). $^1$H NMR (300 MHz, CDCl$_3$, 298 K): δ 7.32 (t, J=8.4 Hz, 2H; H3 and H5), 7.08-6.98 (m, 3H; H2, H4, and H6), 6.90-6.70 (m, 2H; OH and NH). MS (ESI, positive ion mode): km/z: 110 [M+H]$^+$.

Example 1A

Preparation of Phosphorogenic Transition Metal-Based Polypyridyl Complexes of the Present Invention Eight phosphorogenic transition metal-based polypyridyl complexes have been prepared, namely iridium(III)-based polypyridyl complexes [Ir(N^C)$_2$(bpy-nitrone-Me)](PF$_6$) with HN^C=Hppy (complex 1a), Hpq (complex 2a), Hpqe (complex 3a) (bpy-nitrone-Me=4-((methyl(oxido)imino)methyl)-4'-methyl-2,2'-bipyrdine) and ruthenium(II)-based polypyridyl complexes [Ru(N^N)$_2$(bpy-nitrone-Me)](PF$_6$)$_2$ with N^N=bpy (complex 1b), bpyC4 (complex 2b), phen (complex 3b), Ph$_2$-phen (complex 4b) and [Ru(bpy)$_2$(bpy-nitrone-Ph)](PF$_6$)$_2$ (complex 5b) (bpy-nitrone-Ph=4-((phenyl(oxido)imino)methyl)-4'-methyl-2,2'-bipyridine).

Preparation of [Ir(ppy)$_2$(bpy-nitrone-Me)](PF$_6$) (Complex 1a) Having a Structure of Formula (XIIa)

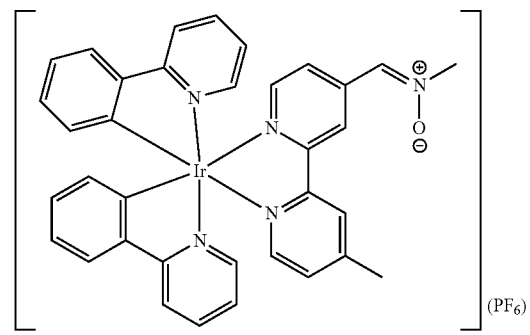

A mixture of [Ir$_2$(ppy)$_4$Cl$_2$] (91 mg, 0.08 mmol) and bpy-nitrone-Me (38 mg, 0.16 mmol) in CH$_2$Cl$_2$/MeOH (20 mL) (1:1, v/v) was stirred under an inert atmosphere of N$_2$ in the dark for 18 h. The mixture was further stirred for 2 h after addition of solid KPF$_6$ (31 mg, 0.16 mmol). The solvent was removed under reduced pressure and the crude product was purified by column chromatography on silica gel using CH$_2$Cl$_2$/MeOH (100:1, v/v) as the eluent. The solvent was removed under reduced pressure to give an orange solid. Subsequent recrystallization of the solid from CH$_2$Cl$_2$/Et$_2$O afforded the complex as orange crystals. Yield: 89 mg (61%). $^1$H NMR (300 MHz, acetone-d$_6$, 298 K, TMS): δ 9.60 (s, 1H; H3 of bpy), 8.61 (s, 1H; H3' of bpy), 8.25 (d, J=8.4 Hz, 2H; H3 of pyridyl ring of ppy), 8.19 (d, J=6.0 Hz, 1H; H6 of bpy), 8.14 (s, 1H, CH=N of nitrone moiety of bpy-nitrone-Me), 8.08 (d, J=6.0 Hz, 1H; H5 of bpy), 8.00-7.84 (m, 7H; H4 and H6 of pyridyl ring and H3 of phenyl ring of ppy and H6' of bpy), 7.57 (d, J=5.1 Hz, 1H; H5' of bpy), 7.17 (t, J=6.6 Hz, 2H; H5 of pyridyl ring of ppy), 7.04 (t, J=7.5 Hz, 2H; H4 of phenyl ring of ppy), 6.92 (t, J=7.5 Hz, 2H; H5 of phenyl ring of ppy), 6.35 (d, J=6.3 Hz, 2H; H6 of phenyl ring of ppy), 4.02 (s, 3H; CH$_3$ of nitrone moiety of bpy-nitrone-Me), 2.64 (s, 3H; CH$_3$ of pyridyl ring of bpy-nitrone-Me). $^{13}$C NMR (150 MHz, acetone-d$_6$, 298 K, TMS): δ 167.9, 167.8, 156.5, 155.6, 152.1, 150.7, 150.6, 150.4, 149.9, 149.2, 149.1, 144.1, 144.0, 140.3, 138.6, 131.6, 131.1, 130.3, 129.3, 125.3, 125.0, 124.9, 123.5, 122.4, 120.8, 119.9, 119.8, 55.1, 20.5. IR (KBr) $\tilde{v}$/cm$^{-1}$: 1606 (C=N), 1178 (N—O), 844 (PF$_6$). MS (ESI, positive-ion mode): m/z: 728 [M-PF$_6^-$]$^+$. Anal. calcd (%) for IrC$_{35}$H$_{29}$N$_5$OPF$_6$·2H$_2$O: C, 46.25, H, 3.66, N, 7.71; found: C, 46.49, H, 3.97, N, 7.95.

Preparation of [Ir(pq)$_2$(bpy-nitrone-Me)](PF$_6$) (Complex 2a) Having a Structure of Formula (XIIb)

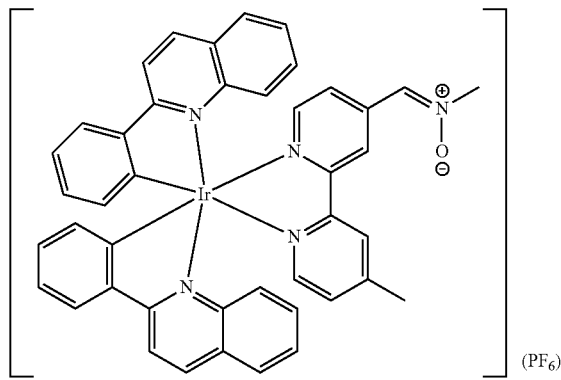

The synthetic procedure was similar to that for the preparation of complex 1a, except that [Ir$_2$(pq)$_4$Cl$_2$] (66 mg, 0.05 mmol) was used instead of [Ir$_2$(ppy)$_4$Cl$_2$]. Subsequent recrystallization of the solid from CH$_2$Cl$_2$/Et$_2$O afforded the complex as orange crystals. Yield: 52 mg (51%). $^1$H NMR (300 MHz, acetone-d$_6$, 298 K, TMS): δ 9.13 (s, 1H; H3 of bpy), 8.54 (d, J=6.9 Hz, 4H; H3 and H4 of quinoline ring of pq), 8.34 (d, J=6.0 Hz, 1H; H3' of bpy), 8.27-8.25 (m, 3H; H8 of quinoline ring of pq and H6 of bpy), 8.20-8.18 (m, 2H; H5 and H6' of bpy), 7.98-7.92 (m, 3H; H5 of quinolone ring of pq and CH=N of nitrone moiety of bpy-nitrone-Me), 7.58-7.43 (m, 5H; H6 of quinoline ring and H3 of phenyl ring of pq and H5' of bpy), 7.21-7.13 (m, 4H; H7 of quinoline ring and H4 of phenyl ring of pq), 6.84 (t, J=7.2 Hz, 2H; H5 of phenyl ring of pq), 6.57 (m, 2H; H6 of phenyl ring of pq), 3.94 (s, 3H; CH$_3$ of nitrone moiety of bpy-nitrone-Me), 2.52 (s, 3H; CH$_3$ of pyridyl ring of bpy-nitrone-Me). $^{13}$C NMR (150 MHz, acetone-d$_6$, 298 K, TMS): δ 170.4, 156.2, 155.3, 152.2, 151.2, 151.0, 148.1, 147.6, 147.4, 146.1, 146.0, 140.3, 140.2, 134.4, 134.3, 131.0, 130.9, 130.6, 129.3, 129.0, 128.0, 127.9, 127.4, 126.8, 126.7, 125.0, 124.8, 124.6, 124.5, 122.8, 120.1, 118.0, 55.1, 20.3. IR (KBr) $\tilde{v}$/cm$^{-1}$: 1606 (C=N), 1178 (N—O), 845 (PF$_6^-$). MS (ESI, positive-ion mode): m/z: 828 [M-PF$_6$]$^+$. Anal. calcd (%) for IrC$_{43}$H$_{33}$N$_6$OPF$_6$·2.5H$_2$O: C, 50.73, H, 3.76, N, 6.88; found: C, 50.62, H, 3.87, N, 7.19.

Preparation of [Ir(pqe)$_2$(bpy-nitrone-Me)](PF$_6$) (Complex 3a) Having a Structure of Formula (XIIc)

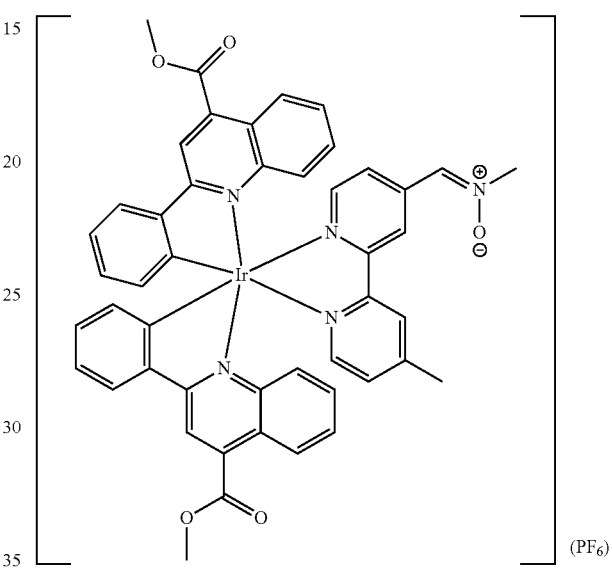

The synthetic procedure was similar to that for the preparation of complex 1a, except that [Ir$_2$(pqe)$_4$Cl$_2$] (99 mg, 0.07 mmol) was used instead of [Ir$_2$(ppy)$_4$Cl$_2$]. Subsequent recrystallization of the solid from CH$_2$Cl$_2$/CH$_3$CN/Et$_2$O afforded the complex as red crystals. Yield: 80 mg (56%). $^1$H NMR (300 MHz, acetone-d$_6$, 298 K, TMS): δ 9.10 (s, 1H; H3 of bpy), 8.88 (d, J=3.3 Hz, 2H; H3 of quinoline ring of pqe), 8.54-8.51 (m, 2H; H5 of quinoline ring of pqe), 8.35-8.31 (m, 4H; H8 of quinoline ring of pqe and H6 and H3' of bpy), 8.21-8.19 (m, 2H; H5 and H6' of bpy), 7.98 (s, 1H; CH=N of nitrone moiety of bpy-nitrone-Me), 7.69-7.53 (m, 5H; H6 of quinoline ring and H3 of phenyl ring of pqe and H5' of bpy), 7.26-7.18 (m, 4H; H7 of quinoline ring and H4 of phenyl ring of pqe), 6.89 (t, J=8.0 Hz, 2H; H5 of phenyl ring of pqe), 6.66-6.62 (m, 2H; H6 of phenyl ring of pqe), 4.14 (s, 3H; CO$_2$CH$_3$ of pqe), 4.13 (s, 3H; CO$_2$CH$_3$ of pqe), 3.94 (s, 3H; CH$_3$ of nitrone moiety of bpy-nitrone-Me), 2.51 (s, 3H; CH3 of pyridyl ring of bpy-nitrone-Me). $^{13}$C NMR (150 MHz, acetone-d$_6$, 298 K, TMS): δ 170.2, 165.3, 156.0, 155.1, 152.5, 151.3, 151.2, 148.2, 148.1, 147.4, 145.6, 145.5, 140.5, 139.2, 139.1, 134.6, 131.2, 131.1, 130.9, 129.3, 127.9, 127.8, 126.7, 125.5, 125.4, 124.7, 124.3, 123.2, 120.2, 118.9, 118.8, 55.1, 52.7, 20.3. IR (KBr) $\tilde{v}$/cm$^{-1}$: 1731 (C=O), 1600 (C=N), 1178 (N—O), 843 (PF$_6$). MS (ESI, positive-ion mode): m/z: 944 [M-PF$_6$]$^+$. Anal. calcd (%) for IrC$_{47}$H$_{37}$N$_5$O$_6$PF$_6$·CH$_3$CN·3.5H$_2$O: C, 49.33, H, 3.97, N, 7.04; found: C, 49.33, H, 4.23, N, 6.92.

Preparation of [Ru(bpy)₂(bpy-nitrone-Me)](PF₆)₂ (Complex 1b) Having a Structure of Formula (XIVa)

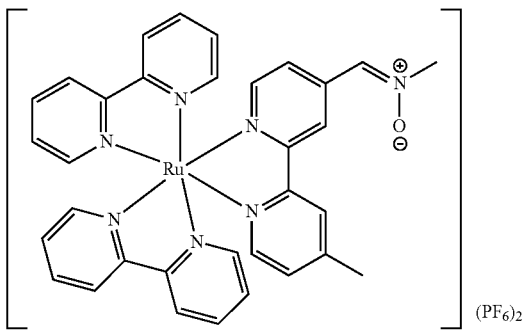

A mixture of cis-[Ru(bpy)₂Cl₂]·2H₂O (50 mg, 0.09 mmol) and bpy-nitrone-Me (25 mg, 0.12 mol) in 10% aqueous EtOH (10 mL) was heated at reflux for 24 h. The volume of the mixture was reduced to about 1 mL under reduced pressure and the solution was then filtered. A saturated aqueous solution of KPF₆ was added to the solution to precipitate a red solid. Subsequent recrystallization from CH₂Cl₂/Et₂O afforded complex 1 b as red crystals. Yield: 61 mg (68%). ¹H NMR (300 MHz, acetone-d₆, 298 K): δ 9.49 (s, 1H; H3 of bpy-nitrone-Me), 8.84 (d, J=8.1 Hz, 4H; H3 and H3' of bpy), 8.61 (s, 1H; H3' of bpy-nitrone-Me), 8.28-8.04 (m, 11H; H4, H4', H6, and H6' of bpy and H5, H6, and CH=N of nitrone moiety of bpy-nitrone-Me), 7.89 (d, J=5.7 Hz, 1H; H6' of bpy-nitrone-Me), 7.60 (t, J=6.6 Hz, 4H; H5 and H5' of bpy), 7.45 (d, 1H, J=5.7 Hz; H5' of bpy-nitrone-Me), 4.00 (s, 3H; CH₃ of nitrone moiety of bpy-nitrone-Me), 2.62 (s, 3H; CH₃ of pyridyl ring of bpy-nitrone-Me). IR (KBr) ṽ/cm⁻¹: 1618 (C=N), 1190 (N—O), 841 (PF₆⁻). MS (ESI, positive-ion mode): m/z: 787 [M-PF₆⁻]⁺, 321 [M-2×PF₆⁻]²⁺. Anal. calcd (%) for RuC₃₃H₂₉N₇OP₂F₁₂·H₂O: C, 41.78, H, 3.29, N, 10.34; found: C, 41.94, H, 3.21, N, 10.25.

Preparation of [Ru(bpyC4)₂(bpy-nitrone-Me)](PF₆)₂ (Complex 2b) Having a Structure of Formula (XIVb)

The synthetic procedure was similar to that for complex 1 b, except that cis-[Ru(bpyC4)₂Cl₂]·2H₂O (70 mg, 0.08 mmol) was used instead of cis-[Ru(bpy)₂Cl₂]·2H₂O. Subsequent recrystallization from CH₂Cl₂/Et₂O afforded complex 2b as red crystals. Yield: 64 mg (63%). ¹H NMR (300 MHz, acetone-d₆, 298 K): δ 9.48 (s, 1H; H3 of bpy-nitrone-Me), 9.17 (s, 4H; H3 and H3' of bpyC4), 8.63 (s, 1H; H3' of bpy-nitrone-Me), 8.36-8.21 (m, 8H; H6, H6', and CONH of bpyC4), 8.18-8.03 (m, 3H; H5, H6, and CH=N of nitrone moiety of bpy-nitrone-Me), 7.96-7.86 (m, 5H; H5 and H5' of bpyC4 and H6 of bpy-nitrone-Me), 7.44 (d, J=5.1 Hz, 1H; H5' of bpy-nitrone-Me), 4.00 (s, 3H; CH₃ of nitrone moiety of bpy-nitrone-Me), 3.44 (t, J=6.0 Hz, 8H; CH₃CH₂CH₂CH₂ of bpyC4), 2.62 (s, 3H; CH₃ of pyridyl ring of bpy-nitrone-Me), 1.68-1.52 (m, 8H; CH₃CH₂CH₂CH₂ of bpyC4), 1.48-1.32 (m, 8H; CH₃CH₂CH₂CH₂ of bpyC4), 0.95 (t, J=7.4 Hz, 12H; CH₃CH₂CH₂CH₂ of bpyC4). IR (KBr) ṽ/cm⁻¹: 1656 (C=O), 1622 (C=N), 1544 (N—H), 1178 (N—O), 844 (PF₆⁻). MS (ESI, positive-ion mode): m/z: 1183 [M-PF₆]⁺, 519 [M-2×PF₆⁻]²⁺. Anal. calcd (%) for RuC₅₃H₆₅N₁₁O₅P₂F₁₂·2H₂O: C, 46.70, H, 5.10, N, 11.30; found: C, 46.72, H, 4.86, N, 11.23.

Preparation of [Ru(phen)₂(bpy-nitrone-Me)](PF₆)₂ (Complex 3b) Having a Structure of Formula (XIVc)

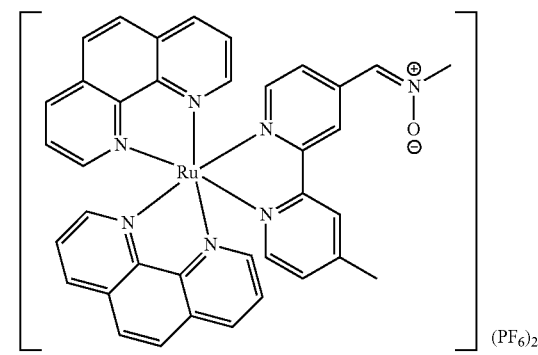

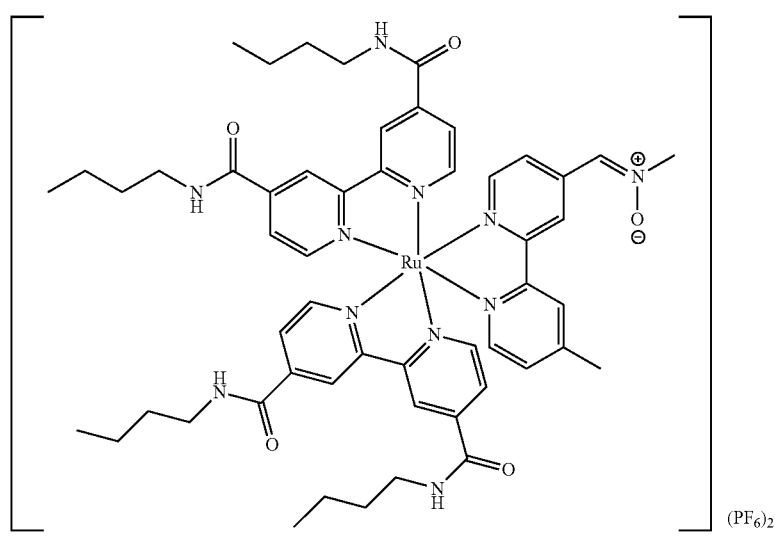

The synthetic procedure was similar to that for complex 1b, except that cis-[Ru-(phen)$_2$Cl$_2$]·2H$_2$O (45 mg, 0.08 mmol) was used instead of cis-[Ru(bpy)$_2$Cl$_2$]·2H$_2$O. Subsequent recrystallization from CH$_2$Cl$_2$/Et$_2$O afforded complex 3b as red crystals. Yield: 62 mg (80%). $^1$H NMR (300 MHz, acetone-d$_6$, 298 K): δ 9.52 (s, 1H; H3 of bpy-nitrone-Me), 8.87 (d, J=8.4 Hz, 2H; H4 of phen), 8.76 (d, J=8.4 Hz, 2H; H7 of phen), 8.66-8.55 (m, 3H; H2 of phen and H3' of bpy-nitrone-Me), 8.47-8.37 (m, 4H; H5 and H6 of phen), 8.28 (d, J=5.4 Hz, 2H; H9 of phen), 8.09 (s, 1H; CH=N of nitrone moiety of bpy-nitrone-Me), 8.06-7.96 (m, 4H; H3 of phen and H6 and H6' of bpy-nitrone-Me), 7.86 (d, J=6.0 Hz, 1H; H5 of bpy-nitrone-Me), 7.79-7.72 (m, 2H; H8 of phen), 7.32 (d, J=4.8 Hz, 1H; H5' of bpy-nitrone-Me), 3.98 (s, 3H; CH$_3$ of nitrone moiety of bpy-nitrone-Me), 2.60 (s, 3H; CH$_3$ of pyridyl ring of bpy-nitrone-Me). IR (KBr) $\tilde{v}$/cm$^{-1}$: 1618 (C=N), 1178 (N—O), 840 (PF$_6^-$). MS (ESI, positive-ion mode): m/z: 837 [M-PF$_6^-$]$^+$, 344 [M-2×PF$_6^-$]$^{2+}$. Anal. calcd (%) for RuC$_{37}$H$_{29}$N$_7$OP$_2$F$_{12}$·2H$_2$O: C, 43.80, H, 3.28, N, 9.66; found: C, 43.77, H, 3.15, N, 9.61.

Preparation of [Ru(Ph$_2$-phen)$_2$(bpy-nitrone-Me)](PF$_6$)$_2$ (Complex 4b) Having a Structure of Formula (XIVd)

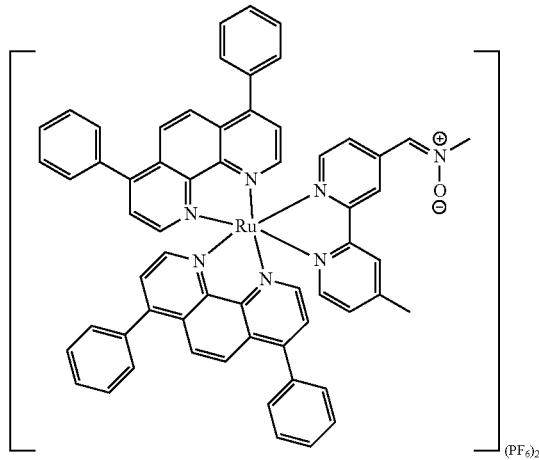

The synthetic procedure was similar to that for complex 1b, except that cis-[Ru(Ph$_2$-phen)$_2$Cl$_2$]·2H$_2$O (40 mg, 0.05 mmol) was used instead of cis-[Ru(bpy)$_2$Cl$_2$]·2H$_2$O. Subsequent recrystallization from CH$_2$Cl$_2$/Et$_2$O afforded complex 4b as red crystals. Yield: 35 mg (60%). $^1$H NMR (300 MHz, acetone-d$_6$, 298 K): δ 9.55 (s, 1H; H3 of bpy-nitrone-Me), 8.79-8.68 (m, 3H; H2 of Ph$_2$-phen and H3' of bpy-nitrone-Me), 8.57-8.50 (m, 2H; H9 of Ph$_2$-phen), 8.40-8.30 (m, 4H; H5 and H6 of Ph$_2$-phen), 8.17-8.09 (m, 2H; H6 and CH=N of nitrone moiety of bpy-nitrone-Me), 8.02 (d, J=5.7 Hz, 1H; H5 of bpy-nitrone-Me), 7.97 (d, J=5.7 Hz, 2H; H3 of Ph$_2$-phen), 7.80-7.60 (m, 23H; H8 and phenyl ring of Ph$_2$-phen and H6' of bpy-nitrone-Me), 7.38 (d, J=5.7 Hz, 1H; H5' of bpy-nitrone-Me), 4.00 (s, 3H; CH$_3$ of nitrone moiety of bpy-nitrone-Me), 2.63 (s, 3H; CH$_3$ of pyridyl ring of bpy-nitrone-Me); IR (KBr) $\tilde{v}$/cm$^{-1}$: 1617 (C=N), 1178 (N—O), 838 (PF$_6^-$); MS (ESI, positive-ion mode): m/z: 1140 [M-PF$_6^-$]$^+$, 497 [M-2×PF$_6^-$]$^{2+}$. Anal. calcd (%) for RuC$_{61}$H$_{45}$N$_7$OP$_2$F$_{12}$·3H$_2$O: C, 54.79, H, 3.84, N, 7.33; found: C, 54.82, H, 3.86, N, 7.30.

Preparation of [Ru(bpy)$_2$(bpy-nitrone-Ph)](PF$_6$)$_2$ (Complex 5b) Having a Structure of Formula (XVa)

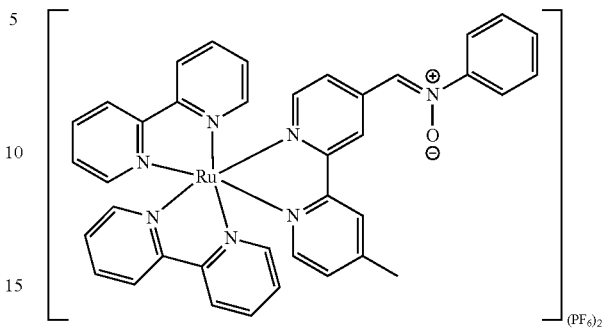

A solution of [Ru(bpy)$_2$(bpy-CHO)](PF$_6$)$_2$ (20 mg, 0.02 mmol) and N-phenylhydroxylamine (4 mg, 0.04 mol) in CH$_2$Cl$_2$ (5 mL) was stirred at room temperature for 72 h to precipitate a red solid. The red solid was collected and washed with CH$_2$Cl$_2$ and Et$_2$O. Subsequent recrystallization from acetone/Et$_2$O afforded complex 5b as red crystals. Yield: 17 mg (77%). $^1$H NMR (300 MHz, acetone-d$_6$, 298 K): δ 9.73 (s, 1H; H3 of bpy-nitrone-Ph), 8.86 (d, J=8.1 Hz, 4H; H3 and H3' of bpy), 8.78 (s, 1H; CH=N of nitrone moiety of bpy-nitrone-Ph), 8.67 (s, 1H; H3' of bpy-nitrone-Ph), 8.38 (d, J=6.3 Hz, 1H; H5 of bpy-nitrone-Ph), 8.30-7.90 (m, 12H; H4, H4', H6, and H6' of bpy and H6, H6', and phenyl ring of bpy-nitrone-Ph), 7.70-7.60 (m, 7H; H5 and H5' of bpy and phenyl ring of bpy-nitrone-Ph), 7.48 (d, J=5.7 Hz, 1H; H5' of bpy-nitrone-Ph), 2.65 (s, 3H; CH$_3$ of bpy-nitrone-Ph); IR (KBr) $\tilde{v}$/cm$^{-1}$: 1618 (C=N), 1088 (N—O), 841 (PF$_6^-$). MS (ESI, positive-ion mode): m/z: 848 [M-PF$_6^-$]$^+$, 352 [M-2×PF$_6^-$]$^{2+}$. Anal. calcd (%) for RuC$_{38}$H$_{31}$N$_7$OP$_2$F$_{12}$·3H$_2$O: C, 43.60, H, 3.56, N, 9.37; found: C, 43.53, H, 3.77, N, 9.40.

The $^1$H NMR spectra revealed only one signal for the CH=N proton, indicating that bpy-nitrone-Me and complexes 1a-5b exist exclusively as the more stable Z-isomers.

Further experimental data regarding the stability of the prepared phosphorogenic transition metal-based pyridyl complexes of the present invention revealed that complexes 1a-5b remained intact in the presence of various reactive oxygen and nitrogen species (RONS) and biological thiols. Incubation of the iridium(III) and ruthenium(II) pyridyl complexes (10 μM) with RONS (100 μM) including H$_2$O$_2$, ClO$^-$, O$_2^-$, $^1$O$_2$, HO·, NO$_2^-$, and NO$_3^-$, and thiols (1 mM) including Cys and GSH in aqueous buffer at 298 K for 24 h did not result in substantial emission enhancement. Mass spectrometric analyses of the reaction mixtures confirmed that the complexes remained intact and no reaction products were isolated.

More specifically, complexes 1a-5b (10 μM) were incubated with various RONS (100 μM) and biological thiols (1 mM) in aerated potassium phosphate buffer (50 mM, pH 7.4)/DMSO (99:1, v/v) at 298 K for 24 h. H$_2$O$_2$ was diluted from a stabilized 30% aqueous solution. ClO$^-$, O$_2^-$, NO$_2^-$, and NO$_3^-$ were delivered from NaClO, KO$_2$, NaNO$_2$, and NaNO$_3$, respectively. $^1$O$_2$ was generated by the reaction of H$_2$O$_2$ with NaClO in a 10:1 ratio, and NaClO concentration represents $^1$O$_2$ concentration. HO· was generated by the reaction of H$_2$O$_2$ with [(NH$_4$)$_2$Fe(SO$_4$)$_2$]·6H$_2$O in a 10:1 ratio, and [(NH$_4$)$_2$Fe(SO$_4$)$_2$]·6H$_2$O concentration represents HO· concentration. To examine the possible reactions of the complexes with RONS and biothiols, the reaction mixture (1 mL) was extracted with $CH_2Cl_2$ (500 µL×3) and the combined organic extract was washed with $H_2O$ (500 µL×3) and subjected to ESI-MS analysis.

Example 1B

Photophysical Properties of the Luminogenic Transition Metal-Based Polypyridyl Complexes Prepared According to Example 1A Upon photoexcitation, the iridium(III) and ruthenium(II) pyridyl complexes displayed extremely weak yellow to red and orange-red emission, respectively. The photophysical data are summarized in Tables 1 and 2, respectively. The very low emission quantum yield of complexes 1a-5b compared with other related iridium(III) and ruthenium(II) systems are expected to be due to quenching by the nitrone moiety.

In particular, the emission quantum yields of the iridium (III) complexes 1a, 2a and 3a ($\phi_{em}$<0.021; Table 1) were much lower than those of common cyclometalated iridium (III) polypyridyl complexes (Li, S. P.-Y. et al., Chem. Eur. J. 2010, 16, 8329; Li, S. P.-Y. et al., Biomaterials 2013, 34, 7519; Lo, K. K.-W. et al., Chem. Commun. 2013, 49, 4271) which is expected to be a consequence of efficient quenching associated with isomerization of the C=N group. Likewise, the ruthenium(II) complexes 1b, 2b, 3b, 4b and 5b showed much lower emission quantum yields ($\phi_{em}$<0.036; Table 2) than common ruthenium(II) polypyridyl complexes (Lo, K. K.-W. and Lee, T. K.-M., Inorg. Chem. 2004, 43, 5275; Lo, K. K.-W. et al., Inorg. Chem. 2008, 47, 200; Tang, T. S.-M. et al., Chem. Eur. J. 2015, 21, 10729). The bpy-nitrone-Me complex 1b was less emissive than its bpy-nitrone-Ph counterpart complex 5b, indicating that N-methyl nitrone quenches the emission of ruthenium(II) complexes more significantly than N-phenyl nitrone.

TABLE 1

Photophysical data of complexes 1a, 2a and 3a.

| Complex | Medium (T/K) | $\lambda_{em}$/nm | $\tau_o$/µs | $\Phi_{em}$ |
|---|---|---|---|---|
| 1a | $CH_2Cl_2$ (298) | 569 | 0.60 | 0.007 |
| | $CH_3CN$ (298) | 571 | 0.41 | 0.002 |
| | Buffer[a] (298) | 579 | 0.12 | 0.0006 |
| | Glass[b] (77) | 526, 618 sh | | |
| 2a | $CH_2Cl_2$ (298) | 553, 593 sh | 1.60 | 0.021 |
| | $CH_3CN$ (298) | 557, 597 sh | 1.85 | 0.017 |
| | Buffer[a] (298) | 557, 595 sh | 2.13 | 0.014 |
| | Glass[b] (77) | 540 (max), 582, 628 sh | | |
| 3a | $CH_2Cl_2$ (298) | 620 | 1.37 | 0.009 |
| | $CH_3CN$ (298) | 642 | 0.69 | 0.004 |
| | Buffer[a] (298) | 652 | 0.03 | 0.0002 |
| | Glass[b] (77) | 594, 644 sh | | |

[a]Potassium phosphate buffer (50 mM, pH 7.4)/MeOH (7:3, v/v).
[b]EtOH/MeOH (4:1, v/v).

TABLE 2

Photophysical data of complexes 1b, 2b, 3b, 4b and 5b.

| Complex | Medium (T/K) | $\lambda_{em}$/nm | $\tau_o$/µs | $\Phi_{em}$ |
|---|---|---|---|---|
| 1b | $CH_2Cl_2$ (298) | 601, 660 sh | 1.20 | 0.006 |
| | MeOH (298) | 609 | 0.94 | 0.006 |
| | Buffer[a] (298) | 611 | 0.64 | 0.004 |
| | Glass[b] (77) | 582 (max), 628, 656 sh | | |
| 2b | $CH_2Cl_2$ (298) | 629, 650 sh | 1.68 | 0.013 |
| | MeOH (298) | 647 | 0.98 | 0.006 |
| | Buffer[a] (298) | 650 | 0.52 | 0.003 |
| | Glass[b] (77) | 617, 660 sh | | |
| 3b | $CH_2Cl_2$ (298) | 598 sh, 651 | 0.86 | 0.004 |
| | MeOH (298) | 599 | 0.81 | 0.005 |
| | Buffer[a] (298) | 602 | 1.03 | 0.006 |
| | Glass[b] (77) | 571 (max), 614, 663 sh | | |
| 4b | $CH_2Cl_2$ (298) | 604, 656 sh | 2.71 | 0.017 |
| | MeOH (298) | 611 | 3.93 | 0.036 |
| | Buffer[a] (298) | 619 | 2.84 | 0.018 |
| | Glass[b] (77) | 596 (max), 652 | | |
| 5b | MeOH (298) | 608 | 0.63 | 0.015 |
| | Buffer[c] (298) | 610 | 0.69 | 0.006 |
| | Glass[b] (77) | 582 (max), 631 | | |

[a]Potassium phosphate buffer (50 mM, pH 7.4)/DMSO (9:1, v/v).
[b]EtOH/MeOH (4:1, v/v).
[c]Potassium phosphate buffer (50 mM, pH 7.4)/MeOH (4:1, v/v).

Example 1C

Reactivity of the Luminogenic Transition Metal-Based Polypyridyl Complexes Prepared According to Example 1A The reactivity of the iridium(III) and ruthenium(II) pyridyl complexes toward a strained alkyne derivative BCN—OH in MeOH at 298 K was studied. The second-order rate constants ($k_2$) of the strain-promoted alkyne-nitrone cycloaddition (SPANC) reaction of complexes 1a-5b are shown in Tables 3 and 4, respectively. The $k_2$ values of the iridium(III) complexes 1a, 2a and 3a and the ruthenium (II) complexes 1b, 2b, 3b, 4b, and 5b were determined to be 0.116-0.238 and 0.078-3.06 $M^{-1}$ $s^{-1}$, respectively, which are about 1.95-76.5 times that of the free ligand bpy-nitrone-Me ($k_2$=0.040 $M^{-1}$ $s^{-1}$). This is attributed to the electron-withdrawing effects of the positively-charged metal centers. The results confirm that the coordination of the nitrone moiety to the complexes advantageously enhances its reactivity. Remarkably, the N-phenyl nitrone complex 5b reacted with BCN—OH at an exceptionally fast rate ($k_2$=3.060 $M^{-1}$ $s^{-1}$), which is at least 36-fold larger than those of the N-methyl nitrone complexes 1b, 2b, 3b and 4b. The accelerated reaction kinetics is assumed to originate from the presence of the more electron-withdrawing phenyl ring at the N-position of the nitrone moiety. Thus, the accelerated reaction kinetics render complexes 1a-5b highly advantageous bioorthogonal probes for biomolecules modified with a strained alkyne moiety.

More specifically, the SPANC reaction kinetics of complexes 1a 5b was studied by UV/Ms absorption spectroscopy. For the ligand bpy-nitrone-Me and the iridium(III) complexes 1a-3a, the $k_2$ values were measured under pseudo first order conditions with a 25- to 100-fold excess of BCN—OH in MeOH at 298 K. The reaction process was followed by monitoring the exponential decay of the absorbance at 306-342 nm upon addition of BCN—OH. The final concentrations of the nitrone compounds were 10 µM and those of BCN—OH ranged from 0.25 to 1.0 mM. For the ruthenium(II) complexes 1b-5b, the $k_2$ values were determined under pseudo first order conditions with a 50- to 200-fold excess of BCN—OH in MeOH at 298 K. The reaction process was monitored by following the exponential decay of the absorbance at 329 nm. The final concentrations of the complexes were 10 µM and those of BCN—OH ranged from 0.5 to 2.0 mM. The data were fitted to a single-exponential equation to give the observed rate constants ($k_{obs}$), which were plotted against the concentrations of BCN—OH to obtain the $k_2$ from the slope of the plots.

TABLE 3

Second-order rate constants ($k_2$) of complexes 1a, 2a and 3a upon reaction with BCN—OH in MeOH at 298 K.

| Complex | $k_2/M^{-1} s^{-1}$ |
|---|---|
| 1a | 0.116 ± 0.005 |
| 2a | 0.185 ± 0.002 |
| 3a | 0.238 ± 0.002 |

TABLE 4

Second-order rate constants ($k_2$) of complexes 1b, 2b, 3b, 4b and 5b upon reaction with BCN—OH in MeOH at 298 K.

| Complex | $k_2/M^{-1} s^{-1}$ |
|---|---|
| 1b | 0.084 ± 0.005 |
| 2b | 0.086 ± 0.005 |
| 3b | 0.080 ± 0.005 |
| 4b | 0.078 ± 0.001 |
| 5b | 3.060 ± 0.108 |

Example 1D

Emission Enhancement Factors ($I/I_0$) of the Luminogenic Transition Metal-Based Polypyridyl Complexes Prepared According to Example 1A Upon Cycloaddition with BCN—OH The strained alkyne BCN—OH has been selected as a model substrate. Upon the reaction with BCN—OH in MeOH at 298 K, the solutions containing the iridium(III) and ruthenium(II) pyridyl complexes showed substantial emission enhancement ($I/I_0$=24.2-30.9 and 3.9-10.2, respectively) (Tables 5 and 6) which is expected to result from the conversion of the quenching nitrone moiety to a non-quenching isoxazoline derivative, the formation of which has been confirmed by ESI-MS. These results confirm that the incorporation of the nitrone moiety into the complexes substantially quenches their emission, and allows them to exhibit significant emission enhancement upon reaction with strained alkyne derivatives. Namely, these findings confirm that complexes 1a-5b remained non-emissive or weakly emissive as long as the nitrone moiety is intact and resume their strongly emissive behavior upon cycloaddition reaction with strained alkynes.

TABLE 5

Emission enhancement factors ($I/I_o$) of complexes 1a, 2a and 3a upon reaction with BCN—OH.

| Complex | $I/I_o^{[a]}$ |
|---|---|
| 1a | 30.6 |
| 2a | 30.9 |
| 3a | 24.2 |

[a]$I_o$ and I are the emission intensities of the nitrone complexes (10 μM) in the absence and presence of BCN—OH (250 μM), respectively, in aerated MeOH at 298 K.

TABLE 6

Emission enhancement factors ($I/I_o$) of complexes 1b, 2b, 3b, 4b and 5b upon reaction with BCN—OH.

| Complex | $I/I_o^{[a]}$ |
|---|---|
| 1b | 9.5 |
| 2b | 7.1 |
| 3b | 10.2 |
| 4b | 5.8 |
| 5b | 3.9 |

[a]$I_o$ and I are the emission intensities of the nitrone complexes (10 μM) in the absence and presence of BCN—OH (1 mM), respectively, in aerated MeOH at 298 K.

Example 1E

Labeling of BCN-Modified Biomolecules by the Luminogenic Transition Metal-Based Polypyridyl Complexes Prepared According to Example 1A The applications of complexes 1a-5b as phosphorogenic labeling reagents for BCN-modified biomolecules were examined. The protein BSA was modified with BCN—NHS and the resultant conjugate BCN-BSA was incubated with complexes 1a-5b in aqueous buffer at 298 K for 18 h (complexes 1a, 2a and 3a) or 24 h (complexes 1 b, 2b, 3b, 4b and 5b). Unmodified BSA was used as a negative control.

More specifically, for the evaluation of the iridium(III) complexes 1a, 2a and 3a, BCN-BSA was prepared by adding BCN—NHS (1.0 mg, 3.43 μmol) in anhydrous DMSO (50 μL) to BSA (0.34 μmol) in carbonate buffer (50 mM, pH 10) (450 μL). The mixture was stirred in the dark at 298 K for 18 h, and then loaded onto a PD-10 size-exclusion column that had been equilibrated with potassium phosphate buffer (50 mM, pH 7.4). Volume fractions between 2.5 and 5.0 mL were collected, concentrated with an YM-50 centricon filter, and then stored at 4° C. The iridium(III) complexes 1a, 2a or 3a (12.5 nmol) in anhydrous DMSO (50 μL) were added to BCN-BSA or unmodified BSA (1.25 nmol) in potassium phosphate buffer (50 mM, pH 7.4) (450 μL). The mixture was stirred in the dark at 298 K for 18 h. An aliquot (10 μL) of the reaction mixture was analyzed by SDS-PAGE.

For the evaluation of the ruthenium(II) complexes 1b, 2b, 3b, 4b and 5b, BCN-BSA was prepared by adding BCN—NHS (0.88 mg, 3.03 μmol) in anhydrous DMSO (100 μL) to BSA (20 mg, 0.31 μmol) dissolved in carbonate buffer (50 mM, pH 10) (400 μL). The mixture was incubated in the dark at 298 K for 24 h. The solution was loaded onto a PD-10 size-exclusion column pre-equilibrated with potassium phosphate buffer (50 mM, pH 7.4). Volume fractions between 2.5 and 5.0 mL were collected, concentrated with a YM-50 microcon filter, and then stored at 4° C. The ruthenium(II) complexes 1 b, 2b, 3b, 4b or 5b (1 mM) in anhydrous DMSO (5 μL) were added to BCN-BSA or unmodified BSA (3.82 μM) potassium phosphate buffer (50 mM, pH 7.4) (495 μL). The mixture was stirred in the dark at 298 K for 24 h. An aliquot (10 μL) of the mixture was analyzed by SDS-PAGE.

Figure 1B:
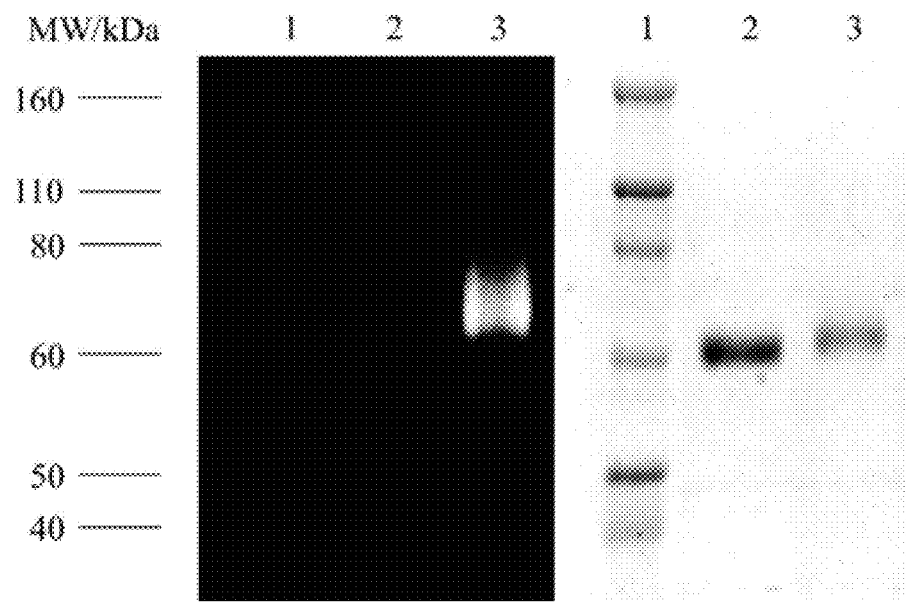
Figure 1C:
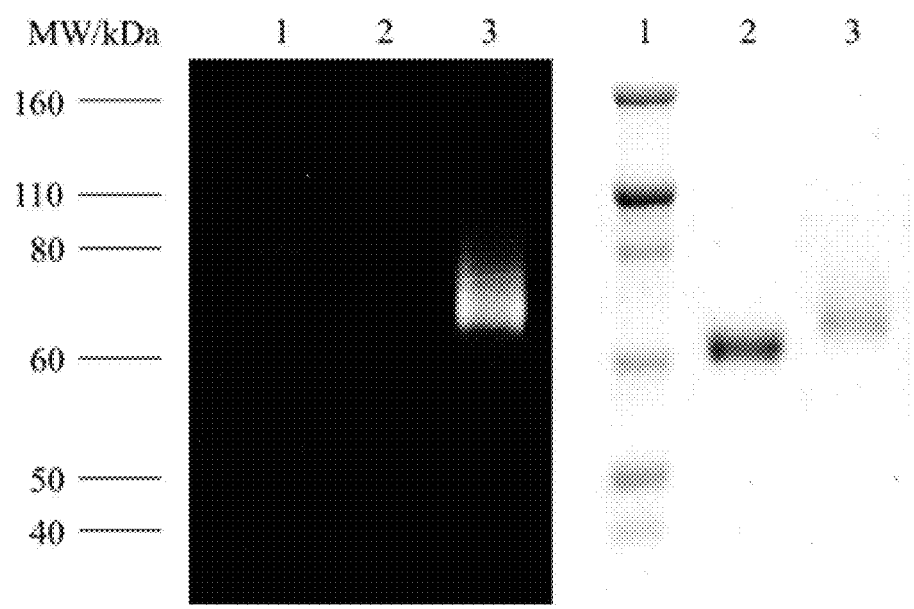
Figure 2:
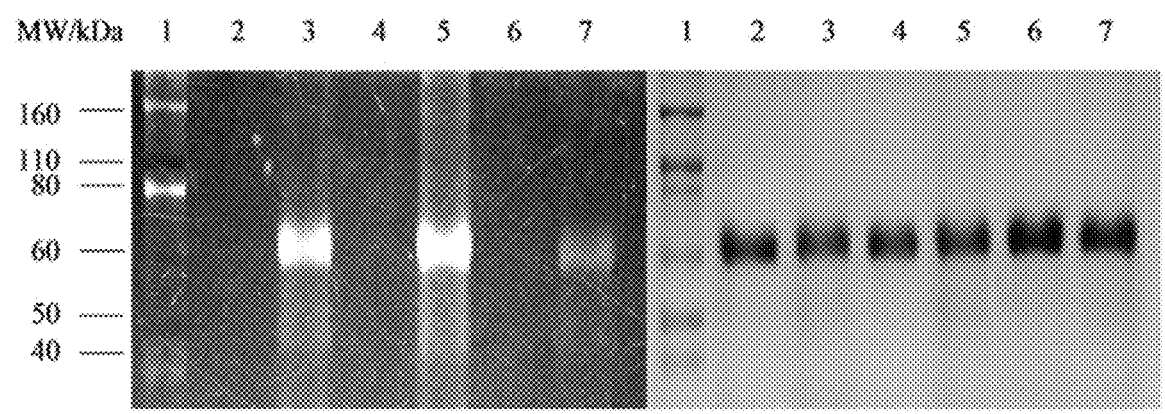
FIG. 2 shows SDS-PAGE patterns of unmodified BSA and BCN-BSA (3.78 µM) incubated with complexes 1 b, 2b, and 5b (10 µM) in potassium phosphate buffer (50 mM, pH 7.4)/DMSO (99:1, v/v) at 298 K. Left: UV transillumination; right: Coomassie Blue staining. Lane 1: protein ladder; lanes 2, 4 and 6: complexes 1 b, 2b, and 5b with unmodified BSA, respectively; lanes 3, 5, and 7: complexes 1 b, 2b, and 5b with BCN-BSA, respectively.
Figure 3:
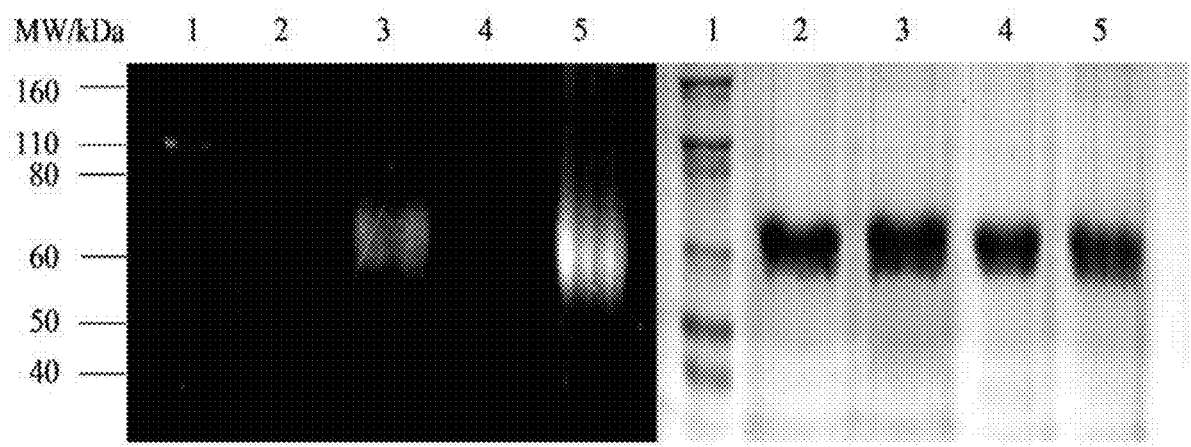
FIG. 3 shows SDS-PAGE patterns of unmodified BSA and BCN-BSA (3.78 µM) incubated with complexes 3b and 4b (10 µM) in potassium phosphate buffer (50 mM, pH 7.4)/DMSO (99:1, v/v) at 298 K. Left: UV transillumination; right: Coomassie Blue staining. Lane 1: protein ladder; lanes 2 and 4: complexes 3b and 4b with unmodified BSA, respectively; lanes 3 and 5: complexes 3b and 4b with BCN-BSA, respectively.

As revealed from the SDS-PAGE analyses (FIG. 1 to FIG. 3), the conjugate BCN-BSA samples were successfully labeled with complexes 1a-5b, resulting in distinct luminescent bands in the gel. The absence of similar bands in the unmodified BSA samples confirmed that the labeling originated from the specific reaction between the nitrone moiety of complexes 1a 5b and the BCN moiety of the conjugate.

Also, the reaction of the iridium(III) and ruthenium(II) pyridyl complexes with BCN-BSA gave rise to very significant emission enhancement (iii, =92.1-618.0 and 9.6-29.2, respectively) (Tables 7 and 8), which is more pronounced than the cases of BCN—OH ($I/I_o$=24.2-30.9 and 3.9-10.2, respectively) (Tables 5 and 6). These observations were ascribed to the increased hydrophobicity and rigidity of the local environment of the complexes upon their bioconjugation with BCN-BSA. These results show that the high environment sensitivity of the emission of luminescent complexes is an additional advantage in targeting BCN-modified biomolecules.

TABLE 7

Emission enhancement factors ($I/I_o$) of complexes 1a, 2a and 3a upon reaction with BCN-BSA and unmodified BSA.

| Complex | $I/I_o$[a] | |
| --- | --- | --- |
| | BCN-BSA | BSA |
| 1a | 292.8 | 1.9 |
| 2a | 92.1 | 1.1 |
| 3a | 618.0 | 5.9 |

[a]$I_o$ and I are the emission intensities of the nitrone complexes (10 μM) in the absence and presence of the proteins (2.50 μM), respectively, in aerated potassium phosphate buffer (50 mM, pH 7.4)/MeOH (9:1, v/v) at 298 K.

TABLE 8

Emission enhancement factors ($I/I_o$) of complexes 1b, 2b, 3b, 4b and 5b upon reaction with BCN-BSA and unmodified BSA.

| Complex | $I/I_o$[a] | |
| --- | --- | --- |
| | BCN-BSA | BSA |
| 1b | 10.7 | 1.1 |
| 2b | 16.9 | 1.1 |
| 3b | 13.9 | 1.0 |
| 4b | 29.2 | 1.6 |
| 5b | 9.6 | 1.1 |

[a]$I_o$ and I are the emission intensities of the nitrone complexes (10 μM) in the absence and presence of the proteins (3.78 μM), respectively, in aerated potassium phosphate buffer (50 mM, pH 7.4)/DMSO (99:1, v/v) at 298 K.

Example 1F

Cellular Uptake of the Luminogenic Transition Metal-Based Polypyridyl Complexes Prepared According to Example 1A The cellular uptake of complexes 1a-5b was examined by ICP-MS. The results showed that an average CHO-K1 cell contained 0.07 to 0.79 fmol of metal after incubation with the iridium(III) complexes at 37° C. for 1 h (Table 9). Interestingly, the cellular uptake efficiency of complex 3a was higher than those of complexes 1a and 2a. This finding should originate from intracellular esterases that convert the ester moieties of complex 3a into negatively charged carboxyl groups, enhancing its intracellular retention. Treatment of HeLa cells with the ruthenium(II) complexes at 37° C. for 12 h resulted in cellular accumulation of 0.31-5.67 fmol of ruthenium per cell (Table 10). Upon incubation of the untreated cells with the complexes, the amounts of ruthenium taken up by an average cell followed the order: 1 b<3b<5b<2b<4b, which seems to be in accordance with their lipophilic character. Further experimental data revealed that after BCN-C10 pretreatment, the cellular uptake efficiency of the complexes 1 b-5b became higher. Remarkably, the uptake of complexes 2b and 5b by BCN-C10-pretreated cells was found to be 8.89 and 2.48 fold, respectively, higher than that by the untreated cells. These findings indicate that the accumulation of the complexes 1 b-5b in BCN-C10-pretreated cells is not only associated with their lipophilicity, but also strongly affected by the bioorthogonal labeling of BCN-C10.

More specifically, for determining the cellular uptake of complexes 1a-3a, CHO-K1 cells were incubated in growth medium/DMSO (99:1, v/v) containing the iridium(III) complex (5 μM) in the dark at 37° C. under a 5% $CO_2$ atmosphere for 1 h. The medium was removed, and the cell layer was thoroughly washed with PBS (1 mL×3). The cells were trypsinized by trypsin-EDTA (500 μL) and harvested with PBS. The resultant solution (2 mL) was heated with 65% $HNO_3$ (2 mL) at 70° C. for 2 h, cooled to room temperature, and analyzed using an Elan 6100 DCR-ICP-MS (PerkinElmer SCIEX Instruments). For determining the cellular uptake of complexes 1 b 5b, HeLa cells with or without pretreatment of BCN-C10 were incubated in growth medium/DMSO (99:1, v/v) containing the ruthenium(II) complexes (40 μM) in the dark at 37° C. under a 5% $CO_2$ atmosphere. After incubation for 12 h, the medium was removed and the cells were thoroughly washed with PBS (1 mL×3). The cells were typsinized by trypsin-EDTA (500 μL) and harvested with PBS. The resultant solution (1.5 mL) was heated with 65% $HNO_3$ (1 mL) at 60° C. for 2 h, cooled to room temperature, and analyzed using an Elan 6100 DCR-ICP-MS.

TABLE 9

Cellular uptake of complexes 1a, 2a and 3a.

| Complex | Amount of iridium/fmol[a] |
| --- | --- |
| 1a | 0.09 ± 0.01 |
| 2a | 0.07 ± 0.01 |
| 3a | 0.79 ± 0.13 |

[a]Amount of iridium associated with an average CHO-K1 cell upon incubation with complexes 1a, 2a or 3a (5 μM) at 37° C. for 1 h, as determined by ICP-MS.

TABLE 10

Cellular uptake of complexes 1b, 2b, 3b, 4b and 5b

| Complex | Amount of ruthenium/fmol[a] |
| --- | --- |
| 1b | 0.31 ± 0.01 |
| 2b | 1.32 ± 0.08 |
| 3b | 0.33 ± 0.06 |
| 4b | 5.67 ± 0.07 |
| 5b | 1.09 ± 0.03 |

[a]Amount of ruthenium associated with an average HeLa cell upon incubation with complexes 1b, 2b, 3b, 4b or 5b (40 μM) at 37° C. for 12 h, as determined by ICP-MS.

Example 1G

Cytotoxicity of the Luminogenic Transition Metal-Based Polypyridyl Complexes Prepared According to Example 1A The MTT assay results revealed that complexes 1a-5b were non-cytotoxic; for example, the $IC_{50}$ values of the iridium(III) pyridyl complexes 1a, 2a and 3a were >50 μM toward live CHO-K1 cells (37° C., 1 h) (Table 11). In the case of the ruthenium(II) pyridylcomplexes, incubation of live HeLa cells with complexes 1b, 2b, 3b, 4b and 5b (40 μM) at 37° C. for 6 h indicated that the cellular viability was >91.37% (Table 12). These data confirm that complexes 1a 5b were essentially non-cytotoxic toward live cells. The results particularly highlight the potential of the luminogenic transition metal-based polypyridyl complexes of the present invention for bioorthogonal labeling. Interestingly, further experimental data revealed that with BCN-C10 pretreatment (200 μM, 1 h), whereas complexes 1 b, 2b, 3b and 5b maintained good biocompatibility, complex 4b caused a much more significant decrease in cell viability. Importantly, although the cellular uptake of complex 2b was substantially higher, it was much less cytotoxic than complex 4b toward the pretreated cells. As BCN-C10 pretreatment did not perturb the cellular uptake of complex 4b, the increased cytotoxicity of the complex toward the pretreated cells most probably resulted from its reaction product with BCN-C10 in the cytoplasm. It is reasonable that the modification of hydrophobic complex 4b with a highly nonpolar decyl chain led to the formation of a more lipophilic isoxazoline adduct, resulting in increased nonspecific interactions with intracellular species and hence extensive cell death. The results also highlight the potential therapeutic use of intracellular bioorthogonal coupling reactions in activating the cytotoxicity of metallo drugs.

More specifically, for determining the cytotoxicity of complexes 1a, 2a and 3a, CHO-K1 cells were seeded in a 96-well flat-bottomed microplate (about 10,000 cells well$^{-1}$) in growth medium (100 µL) and incubated at 37° C. under a 5% $CO_2$ atmosphere for 24 h. The iridium(III) complexes were then added, respectively, to the wells with concentrations ranging from $10^{-7}$ to $10^{-4}$ M in growth medium/DMSO (99:1, v/v). Wells containing untreated cells were used as blank control. The microplate was incubated at 37° C. under a 5% $CO_2$ atmosphere for 1 h. Then, MTT in PBS (10 µL, 5 mg mL$^{-1}$) was added to each well. The microplate was incubated at 37° C. under a 5% $CO_2$ atmosphere for another 4 h. The growth medium was then removed, and DMSO (200 µL) was added to each well. The microplate was further incubated for 15 min. The absorbance of the solutions at 570 nm was measured with a SPECTRAmax 340 microplate reader (Molecular Devices Corp., Sunnyvale, Calif.). The $IC_{50}$ values of the complexes were determined from dose dependence of surviving cells after exposure to the complexes.

For determining the cytotoxicity of complexes 1 b 5b, HeLa cells were seeded in a 96-well flat-bottomed microplate (about 10,000 cells well$^{-1}$) in growth medium (100 µL) and incubated at 37° C. under a 5% $CO_2$ atmosphere for 24 h. The cells were then incubated in either blank medium or growth medium/DMSO (99:1, v/v) (100 µL) containing BCN-C10 (200 µM) in the dark at 37° C. under a 5% $CO_2$ atmosphere for 1 h. The medium was then removed, the cell layer was washed with PBS, and further incubated in growth medium/DMSO (99:1, v/v) (100 µL) containing the ruthenium(II) complexes (40 µM) in the dark at 37° C. under a 5% $CO_2$ atmosphere for 6, 12, or 24 h. Wells containing untreated cells were used as blank control. The microplate was incubated at 37° C. under a 5% $CO_2$ atmosphere for another 4 h. The growth medium was then removed, and DMSO (200 µL) was added to each well. The microplate was further incubated for 15 min. The absorbance of the solutions at 570 nm was measured with a SPECTRAmax 340 microplate reader.

TABLE 11

Cytotoxicity ($IC_{50}$) of complexes 1a, 2a and 3a toward CHO-K1 cells upon incubation in the dark at 37° C. for 1 h, as determined by MTT assays.

| Complex | $IC_{50}$/µM |
|---|---|
| 1a | >100 |
| 2a | >50 |
| 3a | >50 |

TABLE 12

Viability of HeLa cells incubated with complexes 1b, 2b, 3b, 4b and 5b (40 µM) at 37° C. for 6 h.

| Complex | Percentage of survival/% |
|---|---|
| 1b | 91.37 ± 5.73 |
| 2b | 94.83 ± 16.20 |
| 3b | 100.52 ± 6.43 |
| 4b | 96.15 ± 7.64 |
| 5b | 92.78 ± 8.54 |

Example 1H

Bioorthogonal Labeling Properties of the Luminogenic Transition Metal-Based Polypyridyl Complexes Prepared According to Example 1A The bioorthogonal labeling properties of complexes 1a-5b were investigated using CHO-K1 or HeLa cells with or without pretreatment of an exogenous molecule BCN-010, i.e., a BCN-modified decane molecule. The intracellular distribution of BCN-C10 was then imaged using laser scanning confocal microscopy (LSCM).

Figure 4:
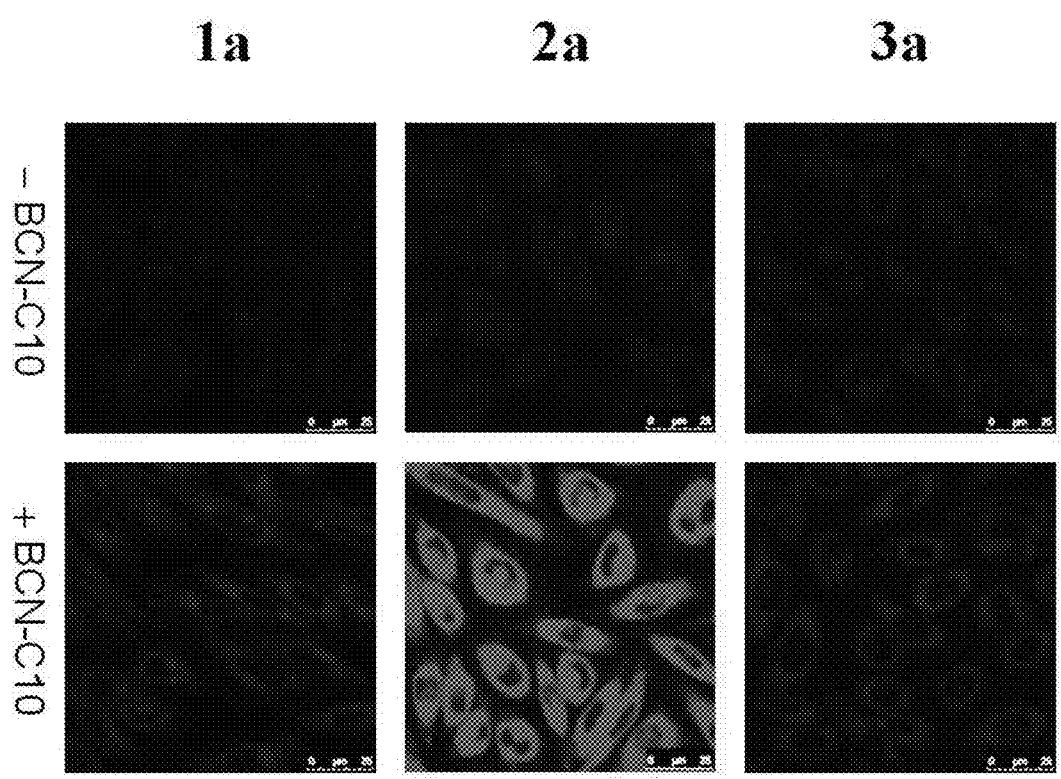
FIG. 4 shows LSCM images of N-((1R,8S,9s)-bicyclo[6.1.0]non-4-yn-9-ylmethyloxycarbonyl)-1-aminodecane (BCN-C10)-untreated and -pretreated CHO-K1 cells incubated with complexes 1a, 2a or 3a (5 µM) at 37° C. for 1 h ($\lambda_{ex}$=488 nm) ("1a", "2a", and "3a" indicate the complexes of the present invention; "—BCN-C10" means BCN-C10-untreated CHO-K1 cells; "+BCN-C10" means BCN-C10-pretreated CHO-K1 cells).

In the study of the iridium(III) nitrone complexes, live CHO-K1 cells were incubated with BCN-C10 (125 µM) for 30 min, thoroughly washed with PBS, further treated with complexes 1a-3a (5 µM) for 1 h, and finally imaged by LSCM. More specifically, CHO-K1 cells were incubated in either blank medium or growth medium/DMSO (99:1, v/v) containing BCN-C10 (125 µM) for 30 min in the dark at 37° C. under a 5% $CO_2$ atmosphere. The medium was then removed and the cells were washed thoroughly with PBS (1 mL×3). The cells were then incubated in growth medium/DMSO (99:1, v/v) containing the iridium(III) complexes (5 µM) for 1 h. The medium was then removed and the cells were washed with PBS (1 mL×3). The coverslip was mounted onto a sterilized glass slide and then imaging was performed using a Leica TCS SPE confocal microscope with an oil immersion 63× objective len and an excitation wavelength at 488 nm. LSCM showed that in the control experiments where BCN-C10 was not used, the cells did not show noticeable emission. On the contrary, the cytoplasmic region of the cells pretreated with BCN-C10 exhibited significant intracellular emission (FIG. 4 and FIG. 5), confirming that the observed emission is due to the specific labeling of BCN-C10 with the complexes inside the cells.

Figure 5:
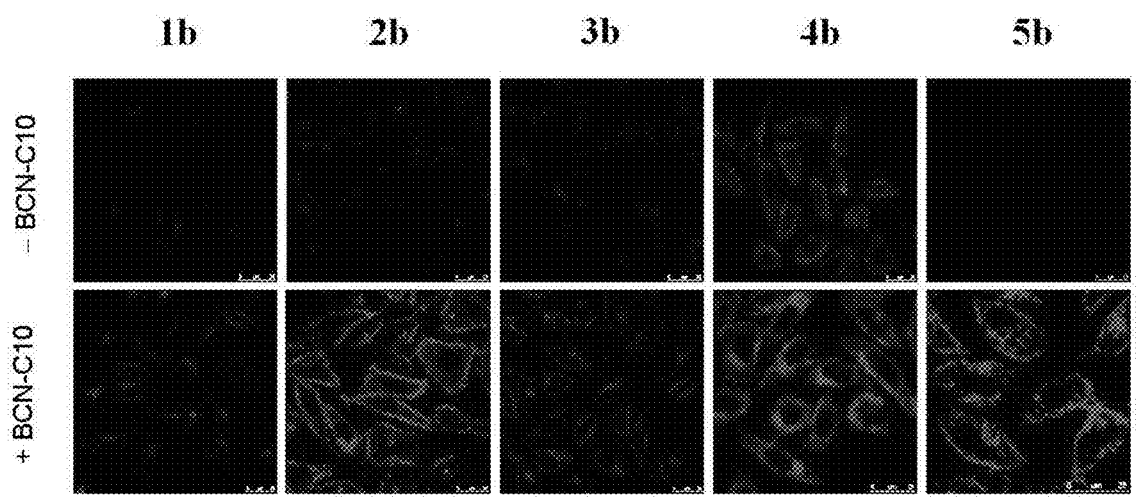
FIG. 5 shows LSCM images of BCN-C10-untreated and -pretreated HeLa cells incubated with complexes 1 b, 2b, 3b, 4b, or 5b (40 µM) at 37° C. for 12 h ($\lambda_{ex}$=488 nm). ("1 b", "2b", "3b", "4b", and "5b" indicate the complexes of the present invention; "—BCN-C10" means BCN-C10-untreated HeLa cells; "+BCN-C10" means BCN-C10-pretreated HeLa cells).
Figure 6:
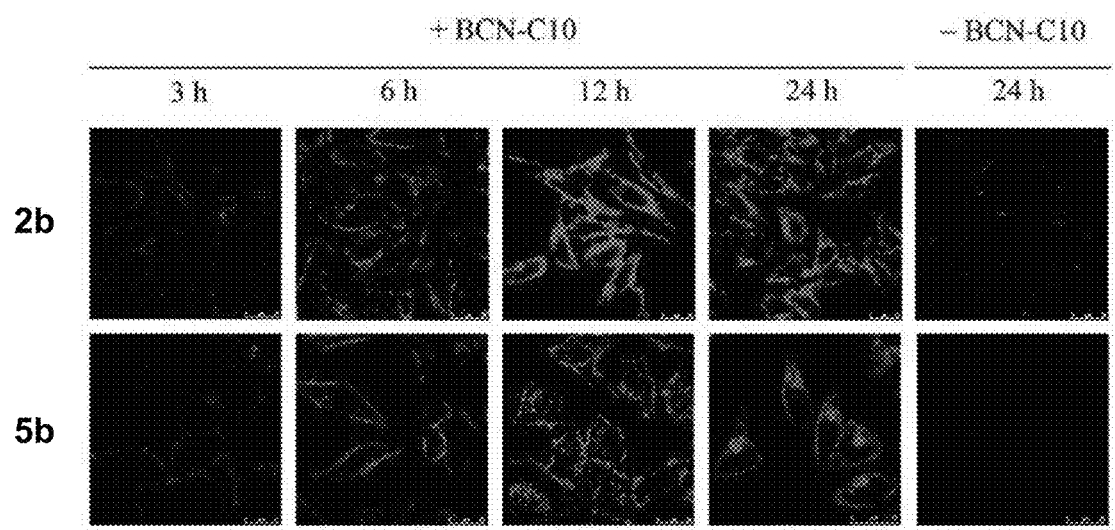
FIG. 6 shows LSCM images of BCN-C10-untreated and -pretreated HeLa cells incubated with complexes 2b or 5b (40 µM) at 37° C. for 3, 6, 12, or 24 h ($\lambda_{ex}$=488 nm). ("2b" and "5b" indicate the complexes of the present invention; "—BCN-C10" means BCN-C10-untreated HeLa cells; "+BCN-C10" means BCN-C10-pretreated HeLa cells).
Figure 7:
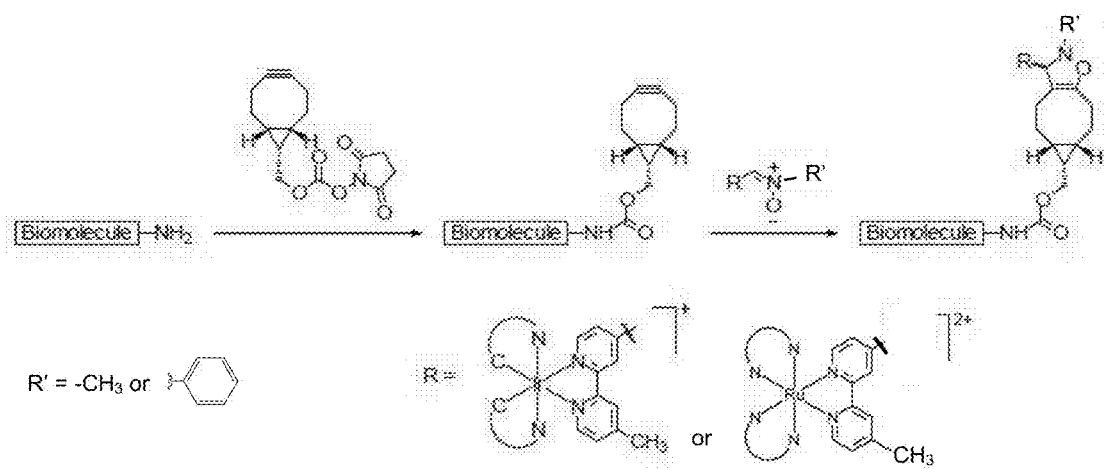
FIG. 7 is a schematic representation illustrating the bioorthogonal labeling of a biomolecule that is modified with and coupled to a strained alkyne moiety with a luminogenic transition metal-based pyridyl complex of the present invention.

In the study of the ruthenium(II) nitrone complexes, live HeLa cells were treated with BCN-C10 (200 µM) for 1 h, thoroughly washed with PBS, then incubated with complexes 1b-5b (40 µM) for 12 h, and finally imaged by LSCM. More specifically, HeLa cells were incubated in growth medium/DMSO (99:1, v/v) containing BCN-C10 (200 µM) in the dark at 37° C. under a 5% $CO_2$ atmosphere for 1 h. After treatment, the medium was removed, the cells were washed thoroughly with PBS (1 mL×3), and then incubated in growth medium/DMSO (99:1, v/v) containing the ruthenium(II) complex (40 µM) in the dark at 37° C. under a 5% $CO_2$ atmosphere. After incubation for 3, 6, 12, or 24 h, the culture medium was removed and the cell was were washed with PBS (1 mL×3). The coverslip was mounted onto a sterilized glass slide and then imaging was performed using a Leica TCS SPE confocal microscope with an oil immersion 63× objective len and an excitation wavelength at 488 nm. LSCM revealed that without BCN-C10 pretreatment, complexes 1b-3b and 5b showed negligible intracellular emission and complex 4b displayed very weak emission in the cytoplasm due to emission quenching by the nitrone moiety (FIG. 5). However, with BCN-C10 pretreatment, cells incubated with complexes 1b and 3b showed weak but enhanced emission while those loaded with complexes 2b, 4b, and 5b exhibited intense subcellular staining (FIG. 5), as a consequence of the intracellular labeling of BCN-C10. Additionally, BCN-C10-pretreated cells were incubated with complexes 2b and 5b for different time periods (3, 6, 12, and 24 h) (FIG. 6). The results indicated that the complexes selectively lighted up the cell surface after 6 h and showed intense cell membrane staining plus some sharp vesicles in the cytoplasmic regions adjacent to cell membrane after 12 h. However, the cell surface staining of the complexes became less distinguishable at a prolonged incubation time of 24 h and intense granular staining in the cytoplasm was observed. Further experimental data revealed that upon incubation of BCN-C10-pretreated HeLa cells with the complexes 1b-5b, different subcellular structures were stained: punctate cell surface staining with complexes 1b and 3b, cell membrane staining with complexes 2b and 5b, and cytosolic staining with complex 4b. The regioselective staining is assumed to be closely related to the subcellular distribution of BCN-C10, and the lipophilicity and reactivity of the complexes.

These experimental data confirm that the phosphorogenic properties and high reactivity of complexes 1a-5b of the present invention enable the bioorthogonal labeling and imaging of BCN-modified substrates in their native biological environments.

The invention claimed is:

1. A luminogenic transition metal-based pyridyl complex containing a nitrone moiety and a transition metal ion, the nitrone moiety acts as both a bioorthogonal functional group and an emission quencher to the complex when the nitrone moiety remains intact; the nitrone moiety comprising a structure of Formula (I)

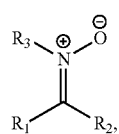

Formula (I)

wherein $R_1$ is a polypyridyl ligand having a structure of Formula (II):

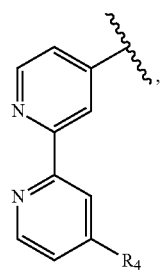

Formula (II)

with $R_4$ being an alkyl group, $R_2$ being a hydrogen atom, and $R_3$ being an alkyl or an aryl group; and wherein the nitrone moiety can undergo a cycloaddition reaction with a complementary bioorthogonal functional group containing a strained alkylne moiety coupled to a biomolecule, and resume emission of the complex after the cycloaddition reaction.

2. The luminogenic transition metal-pyridyl complex of claim 1, which is phosphorogenic with an emission wavelength between about 500 snm and about 700 nm.

3. The luminogenic transition metal-based pyridyl complex of claim 1, which comprises a transition metal ion, a polypyridyl ligand having a structure of Formula (III):

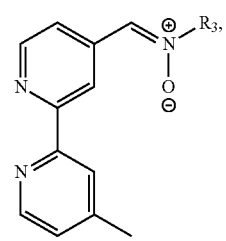

Formula (III)

wherein $R_3$ is a methyl or a phenyl group, and two identical pyridyl ligands selected from the structures of Formula (IV) to (X):

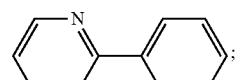

Formula (IV)

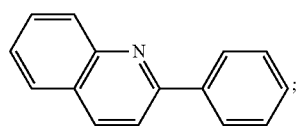

Formula (V)

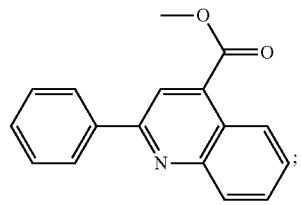

Formula (VI)

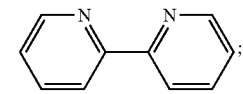

Formula (VII)

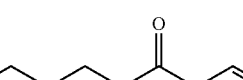

Formula (VIII)

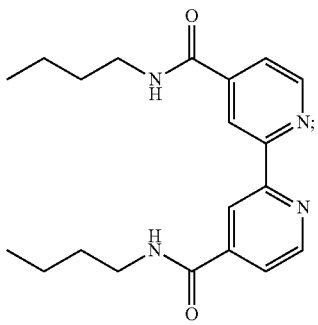

Formula (IX)

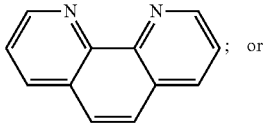

; or

Formula (X)

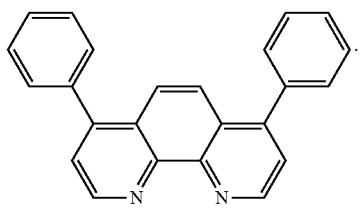

4. The luminogenic transition metal-based pyridyl complex of claim 1, which comprises a structure of Formula (XII) including any salts and solvates thereof:

Formula (XII)

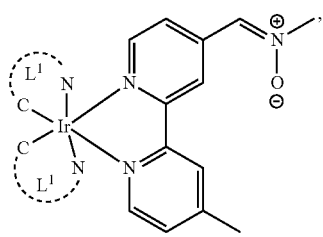

with $L^1$ being a pyridyl ligand selected from a structure of:

Formula (IV)

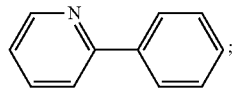;

Formula (V)

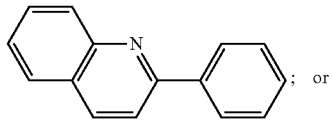; or

Formula (VI)

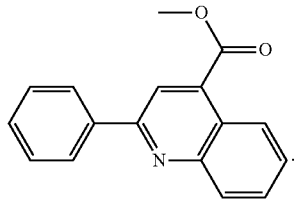.

5. The luminogenic transition metal-based pyridyl complex of claim 1, which comprises a structure of Formula (XIV) including any salts or solvates thereof:

Formula (XIV)

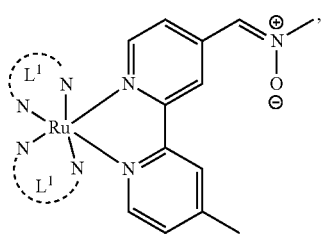

with $L^1$ being a pyridyl ligand selected from a structure of:

Formula (VII)

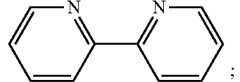;

Formula (VIII)

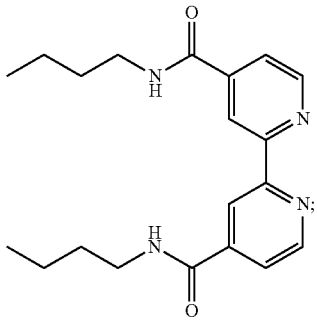

Formula (IX)

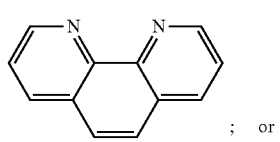; or

Formula (X)

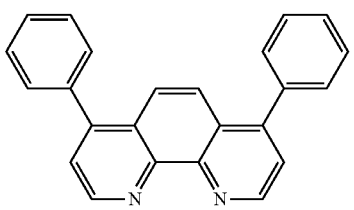.

6. The luminogenic transition metal-based pyridyl complex of claim 1, which comprises a structure of Formula (XV) including any salts or solvates thereof:

Formula (XV)

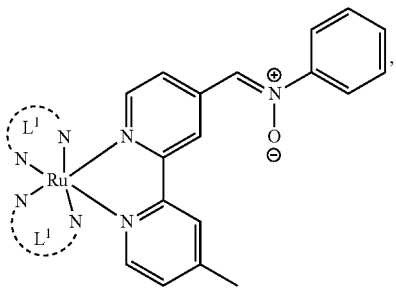

with $L^1$ being a pyridyl ligand having a structure of Formula (VII):

Formula (VII)

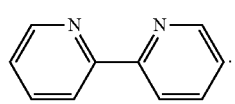.

7. The luminogenic transition metal-based pyridyl complex of claim 1, which comprises a structure selected from:

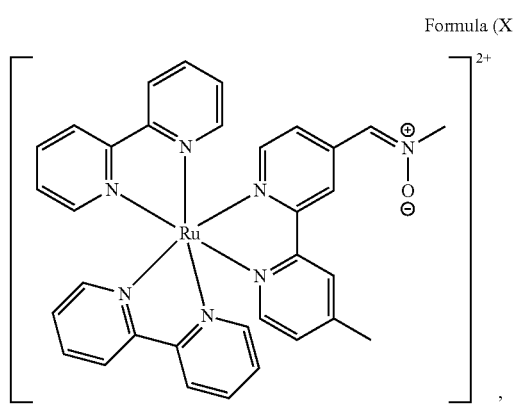
Formula (XIVa)
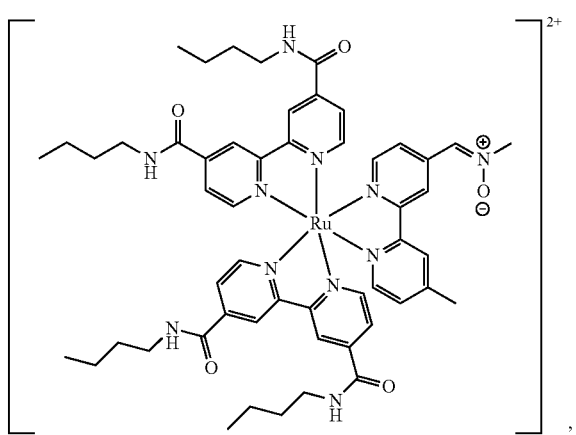
Formula (XIVb)
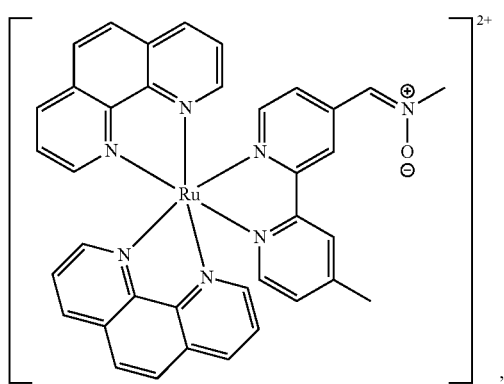
Formula (XIVc)
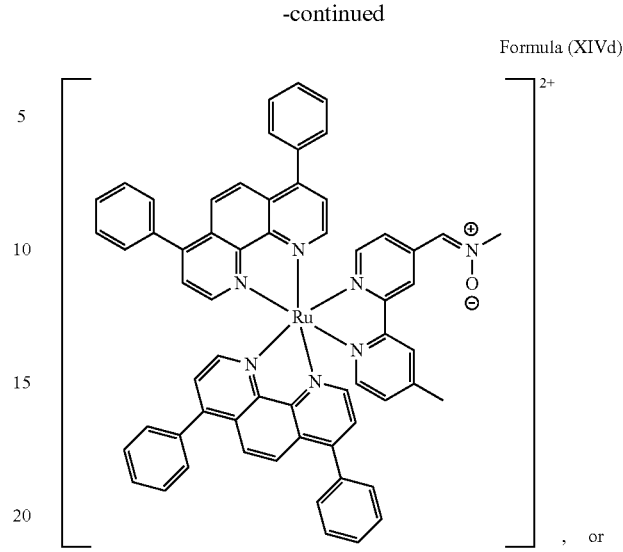
Formula (XIVd), or
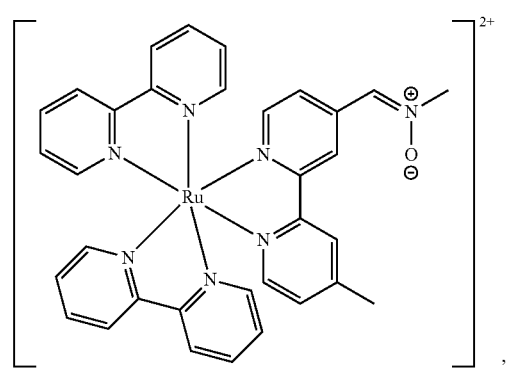
Formula (XVa);
including any salts or solvates thereof.
8. The luminogenic transition metal-based pyridyl complex of claim 1, which essentially consists of a structure selected from:
Formula (XIVa)

-continued

Formula (XIVb)

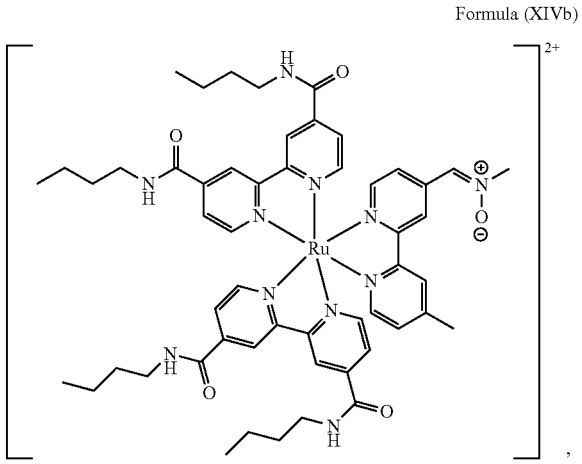

Formula (XIVc)

Formula (XIVd)

, or

-continued

Formula (XVa)

and a counterion.

9. A method for bioorthogonal labeling of a biomolecule with a luminogenic transition metal-based pyridyl complex of claim 1 comprising:

(i) introducing a biomolecule with a complementary bioorthogonal functional group coupled to said biomolecule into a living system; and (ii) introducing the luminogenic transition metal-based pyridyl complex of claim 1 into the living system such that a bioorthogonal reaction occurs between the nitrone moiety of the transition metal-based pyridyl complex and the complementary bioorthogonal functional group coupled to the biomolecule.

10. The method for bioorthogonal labeling of claim 9, wherein the living system is selected from an organism, a cell, or a cell population and wherein the biomolecule is a targeting biomolecule.

11. The method for bioorthogonal labeling of claim 9, wherein the complementary bioorthogonal functional group coupled to the biomolecule used in step (i) contains a strained alkyne moiety.

12. The method for bioorthogonal labeling of claim 9, wherein the complementary bioorthogonal functional group coupled to the biomolecule comprises a structure of Formula (XVII):

(XVII)

13. The method for bioorthogonal labeling of claim 9, wherein the transition metal-based ovridvl complex comprises a structure selected from:

Formula (XIIa)
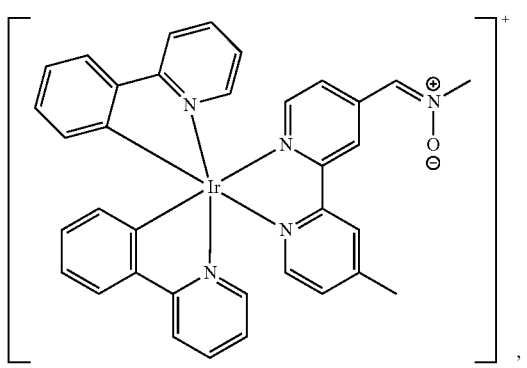
Formula (XIIb)
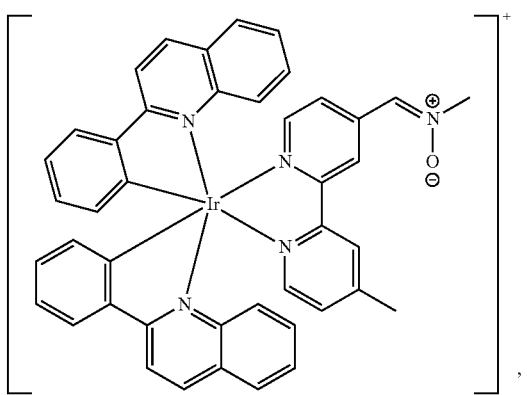
Formula (XIIc)
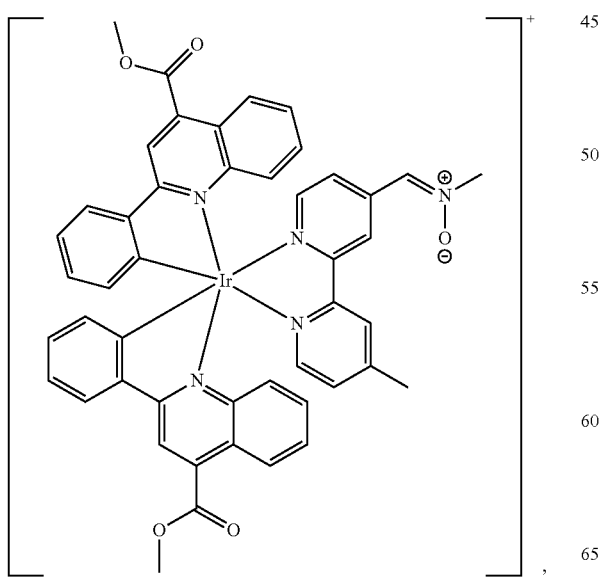
-continued
Formula (XIVa)
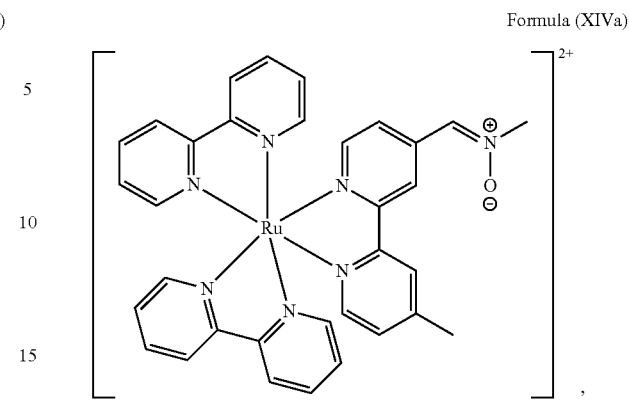
Formula (XIVb)
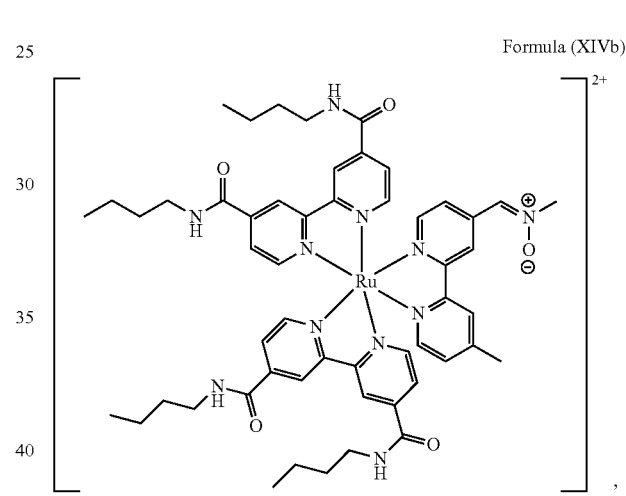
Formula (XIVc)
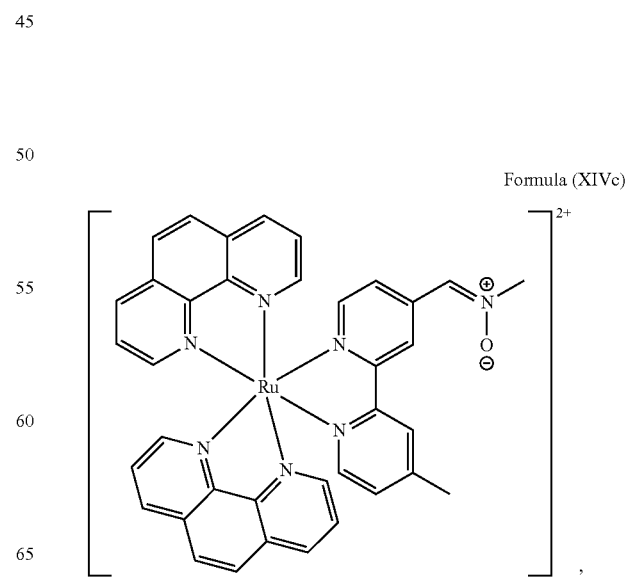

-continued

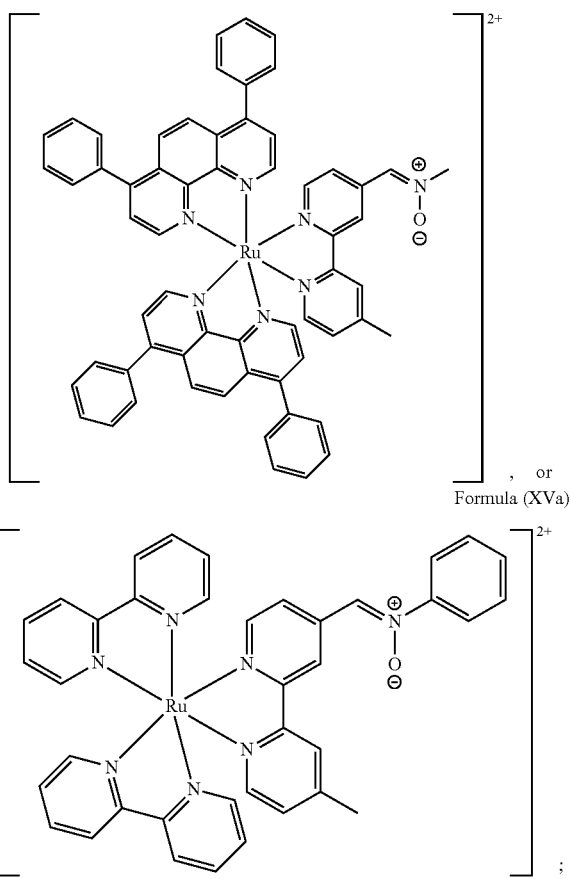

including any salts or solvates thereof.

14. A method for staining of a cell structure comprising:

(i) introducing N-[(1R,8S,9s)-bicyclo[6.1.0]non-4-yn-9-ylmethyloxycarbonyl]-1-aminodecane of Formula (XIX) into a cell population:

Formula (XIX)

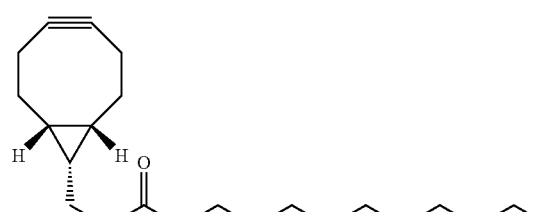

and (ii) introducing the luminogenic transition metal-based pyridyl complex of claim 1 into the cell population such that a bioorthogonal reaction occurs between the nitrone moiety of the transition metal-based pyridyl complex and the strained alkyne moiety of compound of Formula (XIX);

wherein the cell structure is the cell membrane and the transition metal-based pyridyl complex comprises a structure selected from:

Formula (XIVb)

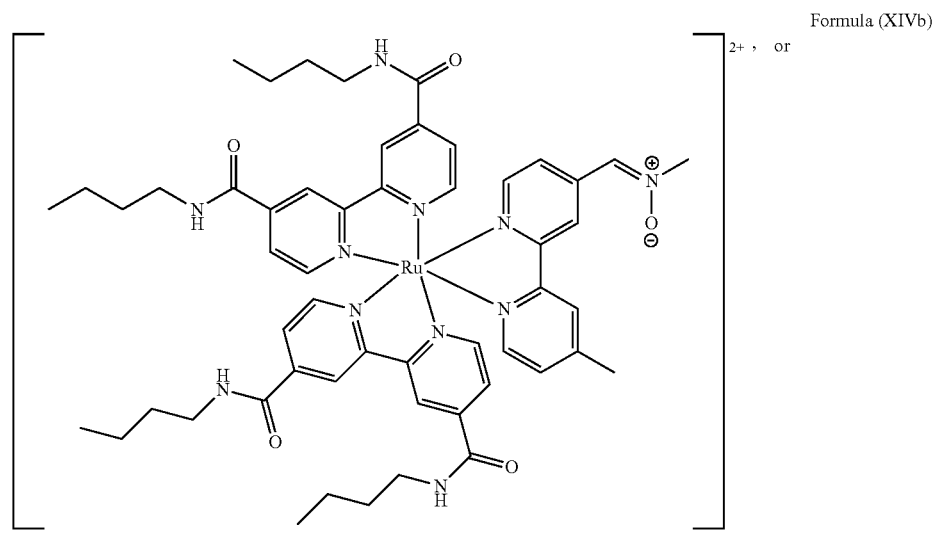

-continued

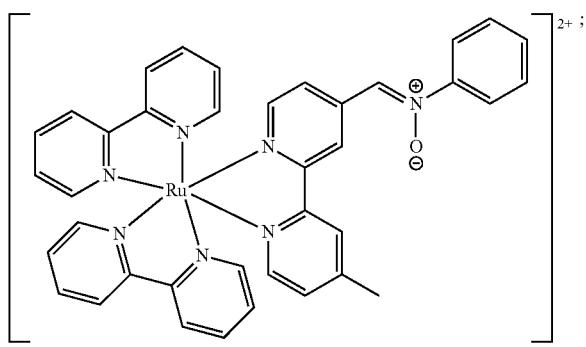

including any salts and solvates thereof.

15. A method for in vivo imaging of an organism comprising:
    (i) administering an effective amount of a biomolecule with a complementary bioorthogonal functional group coupled to the biomolecule to said organism;
    (ii) administering an effective amount of a luminogenic transition metal-based pyridyl complex of claim 1 to said organism such that a bioorthogonal reaction occurs between the nitrone moiety of the transition metal-based pyridyl complex and the complementary bioorthogonal functional group coupled to the biomolecule; and
    (iii) imaging the organism, wherein a signal indicates the presence of a labeled biomolecule.

16. The method for in vivo imaging of claim 15, wherein the biomolecule in step (i) is a targeting biomolecule and the complementary bioorthogonal functional group coupled to the biomolecule used in step (i) comprises a structure of Formula (XVII):

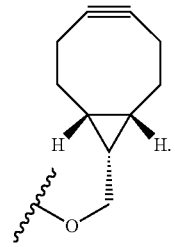

(XVII)

17. The method for in vivo imaging of claim 15, wherein the transition metal-based pyridyl complex comprises a structure selected from:

Formula (XIIa)

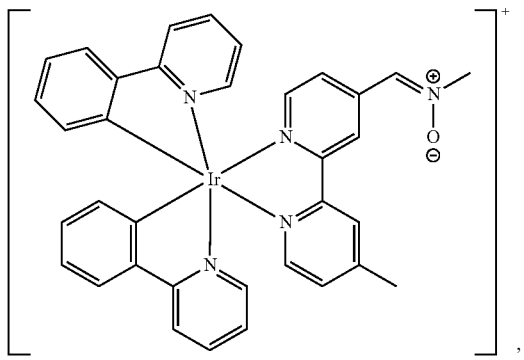

Formula (XVa)

-continued

Formula (XIIb)

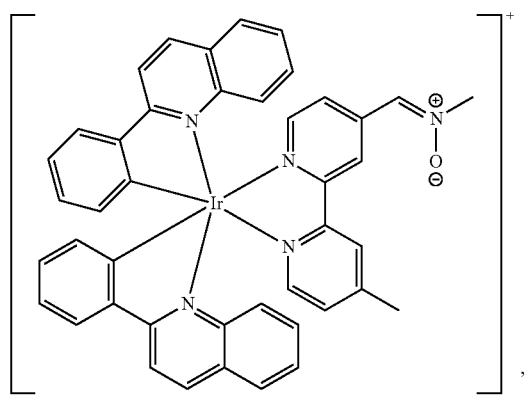

Formula (XIIc)

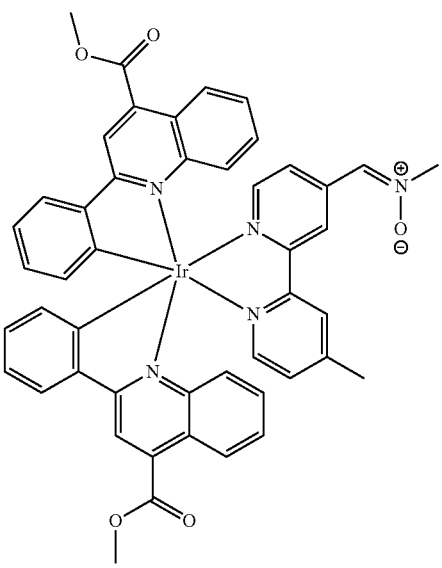

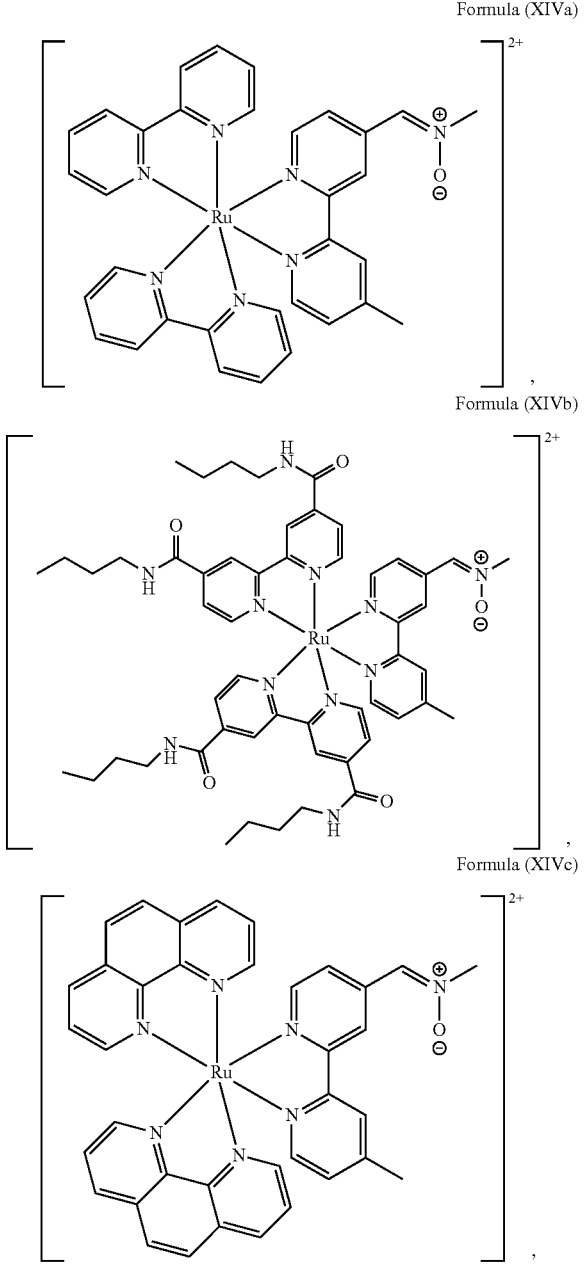
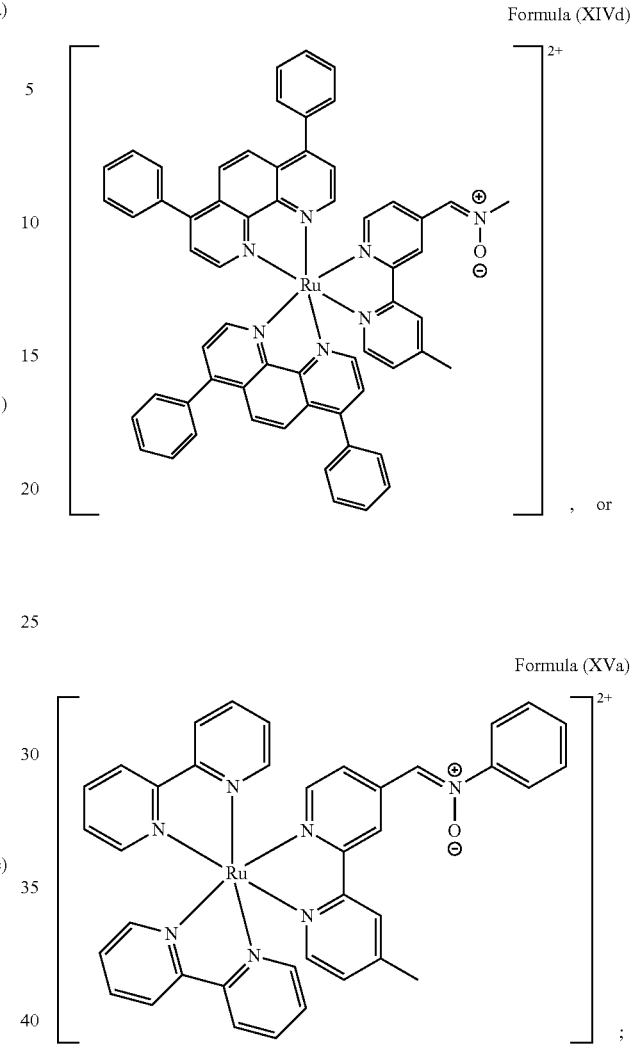
including any salts or solvates thereof.
18. The method for in vivo imaging of claim 15, wherein step (iii) comprises phosphorescence detection with confocal microscopy.
* * * * *